(12) United States Patent
Sahin et al.

(10) Patent No.: US 10,301,368 B2
(45) Date of Patent: May 28, 2019

(54) CYTOKINE FUSION PROTEINS

(71) Applicants: BioNTech RNA Pharmaceuticals GmbH, Mainz (DE); Universität Stuttgart, Stuttgart (DE); TRON-Translationale Onkologie an der Universitätsmedizin der Johannes Gutenberg-Universität Mainz GGmbH, Mainz (DE)

(72) Inventors: Ugur Sahin, Mainz (DE); Friederike Gieseke, Mainz (DE); Ronald Backer, Mommenheim (DE); Sebastian Kreiter, Mainz (DE); Roland Kontermann, Nürtingen (DE); Klaus Pfizenmaier, Tiefenbronn (DE); Sina Fellermaier, Stuttgart (DE); Dafne Müller, Stuttgart (DE)

(73) Assignees: BIOTECH RNA PHARMACEUTICALS GMBH, Mainz (DE); TRON-TRANSLATIONALE ONKOLOGIE AN DER UNIVERSITÄTSMEDIZIN DER JOHANNES GUTENBERG-UNIVERSITÄT MAINZ GMBH, Mainz (DE); UNIVERSITÄT STUTTGART, Stuttgart (DE)

(*) Notice: Subject to any disclaimer, the term of this patent is extended or adjusted under 35 U.S.C. 154(b) by 0 days.

(21) Appl. No.: 15/543,566

(22) PCT Filed: Jan. 15, 2016

(86) PCT No.: PCT/EP2016/050773
§ 371 (c)(1),
(2) Date: Jul. 13, 2017

(87) PCT Pub. No.: WO2016/113395
PCT Pub. Date: Jul. 21, 2016

(65) Prior Publication Data
US 2018/0002392 A1   Jan. 4, 2018

(30) Foreign Application Priority Data
Jan. 15, 2015 (WO) ............... PCT/EP2015/050682

(51) Int. Cl.
*C07K 14/52* (2006.01)
*C07K 14/525* (2006.01)
*A61K 38/17* (2006.01)

(52) U.S. Cl.
CPC ........ *C07K 14/525* (2013.01); *A61K 38/1793* (2013.01); *C07K 14/52* (2013.01); *C07K 2319/70* (2013.01)

(58) Field of Classification Search
CPC .. C07K 14/52; C07K 14/525; C07K 2319/70; A61K 38/1793
See application file for complete search history.

(56) References Cited

U.S. PATENT DOCUMENTS

2010/0303811 A1   12/2010   Ochi

FOREIGN PATENT DOCUMENTS

| WO | WO 2001/49866 | 7/2001 |
| WO | WO 2005/103077 | 11/2005 |
| WO | 10/010051 A1 | 1/2010 |
| WO | 14/145355 A1 | 9/2014 |

OTHER PUBLICATIONS

Berg D, et al. (2007) Cell Death and Differentiation. 14:2021-2034. Available online at—doi:10.1038/sj.cdd.4402213; published online Aug. 17, 2007.*
International Preliminary Report on Patentability dated Jul. 27, 2017 for PCT/EP2016/050773 filed Jan. 15, 2016, 8 pages.
Kontermann; R.E, "Antibody-cytokine fusion proteins", Archives of Biochemistry and Biophysics, 2012, 526(2), 194-205.
Kornbluth; R.S., "Multimeric forms of CD40 ligand (CD40L), 4-1BB ligand (4-1BBL), OX40 ligand (OX40L), CD27L/DC70, and other TNFSFs for cancer immunotherapy", 2013, retrieved from the internet, XP055202450, 1 page.
Krippner-Heidenreich et al., "Single-Chain TNF, a TNF Derivative with Enhanced Stability and Antitumoral Activity", The Journal of Immunology, 2008, 180(12), 8176-8183.
Wyzgol et al., "Timer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand", The Journal of Immunology, 2009, 183(3), 1851-1861.
Bremer; E., "Targeting of the Tumor Necrosis Factor Receptor Superfamily for Cancer Immunotherapy", ISRN Oncology, 2013, 176(2), 25 pages.

(Continued)

*Primary Examiner* — Robert S Landsman
(74) *Attorney, Agent, or Firm* — McDonnell Boehnen Hulbert & Berghoff LLP

(57) ABSTRACT

The present invention relates to cytokine fusion proteins and to nucleic acid molecules encoding such cytokine fusion proteins. The present invention further relates to cells, non-human organisms. pharmaceutical compositions and kits comprising the cytokine fusion proteins or the nucleic acid molecules encoding them, as well as to their use as medicaments.

22 Claims, 54 Drawing Sheets
Specification includes a Sequence Listing.

(56) References Cited

OTHER PUBLICATIONS

Chang et al., "Dual biological functions of an interleukin-1 receptor antagonist-interleukin-10 fusion protein and its suppressive effects on joint inflammation", Immunology, 2004, 112(4), 643-650.

Sina Fellermeier-Kopf et al., "Duokines: a novel class of dual-acting co-stimulatory molecules arising in cis or trans", Oncoimmunology, vol. 7, No. 9, Aug. 1, 2018, p. e1471442.

\* cited by examiner

HT1080-CD40
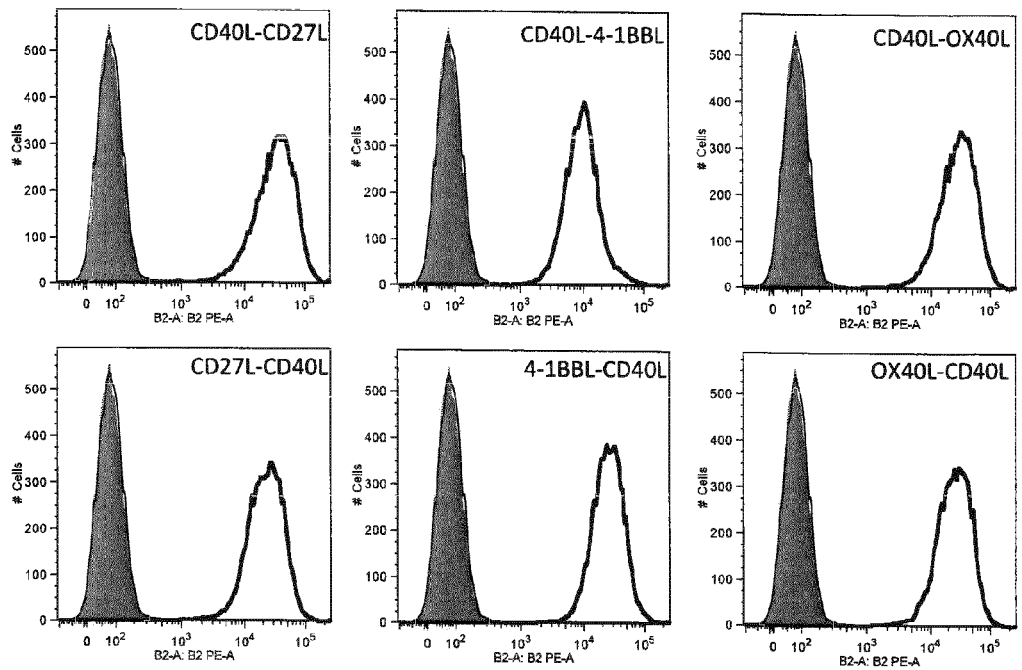
HT1080-CD27
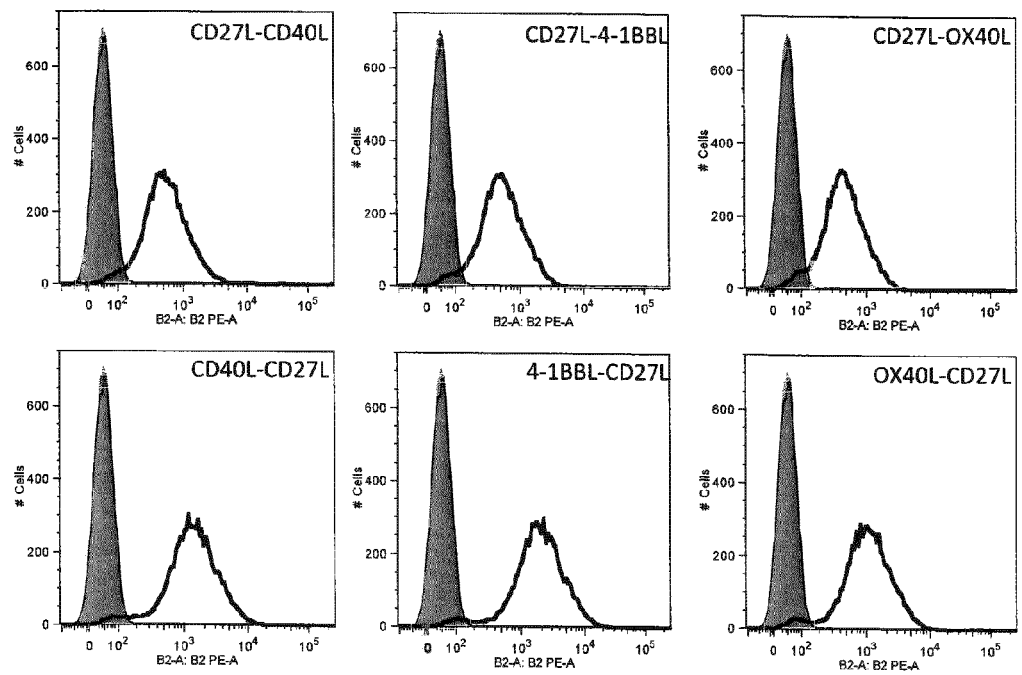
FIG. 6A

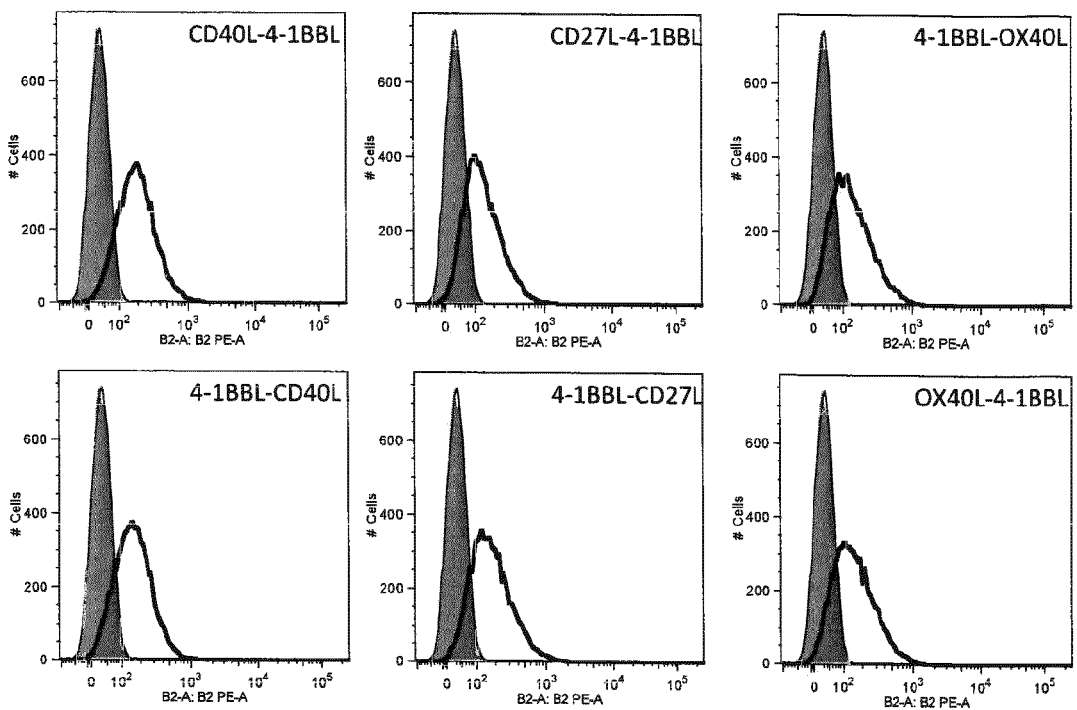
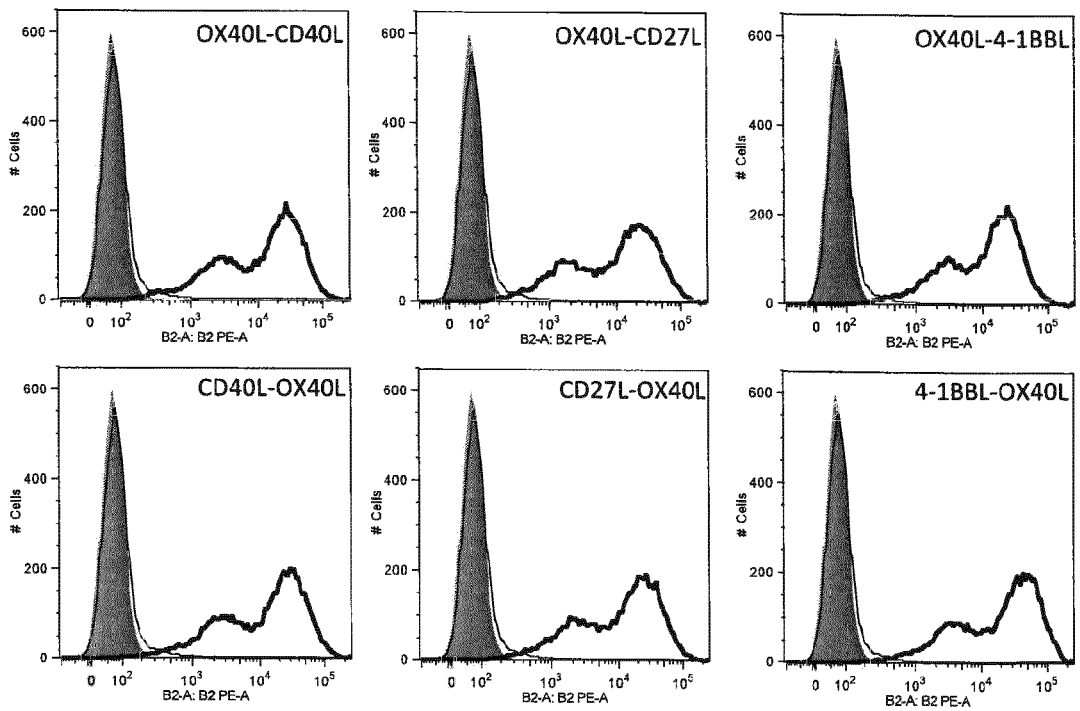
FIG. 6B

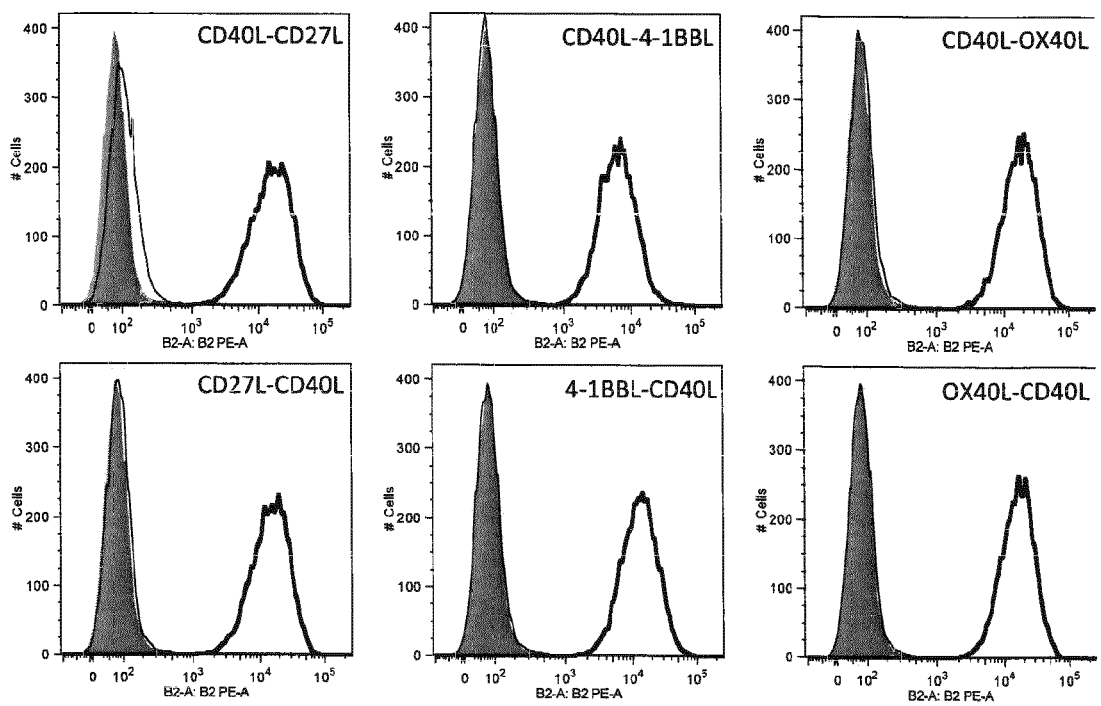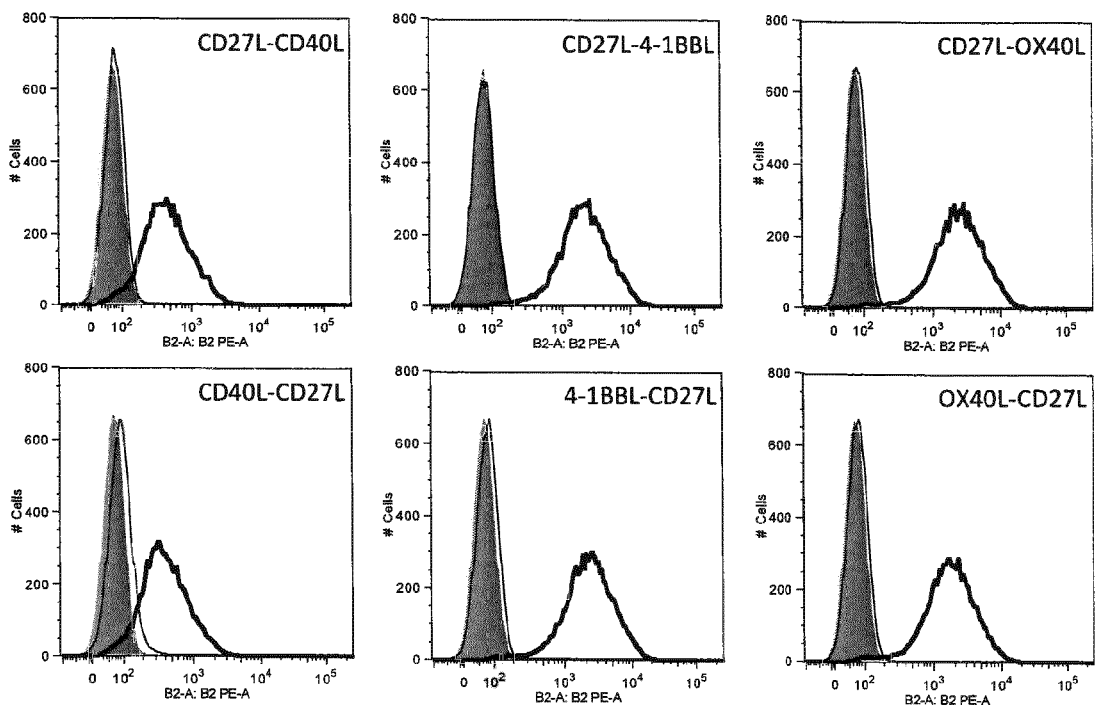
FIG. 7A

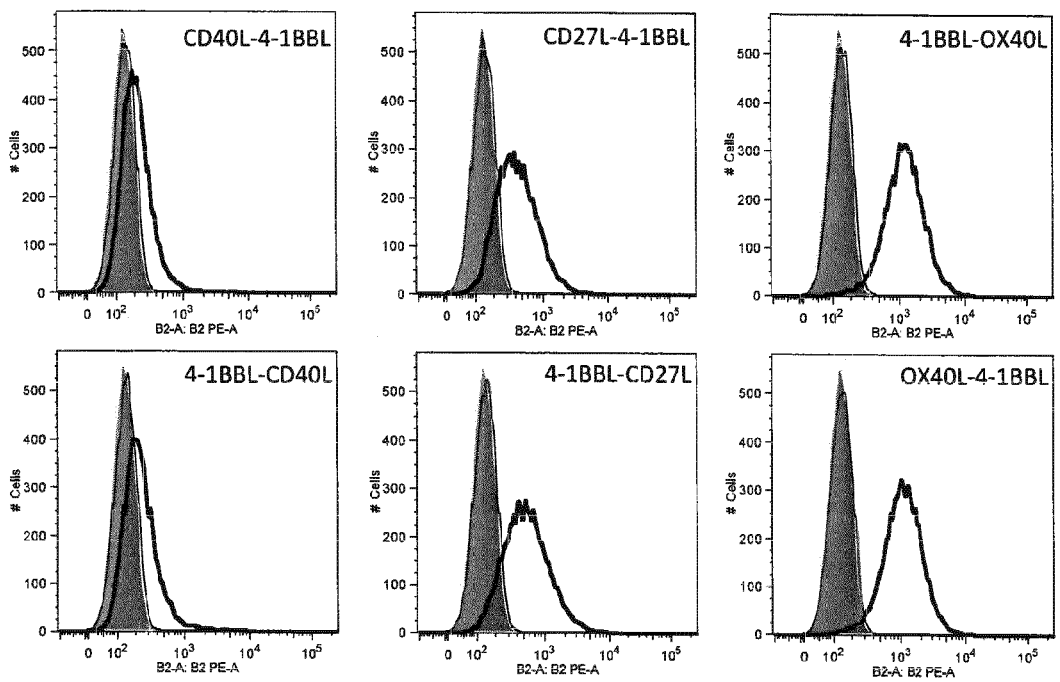
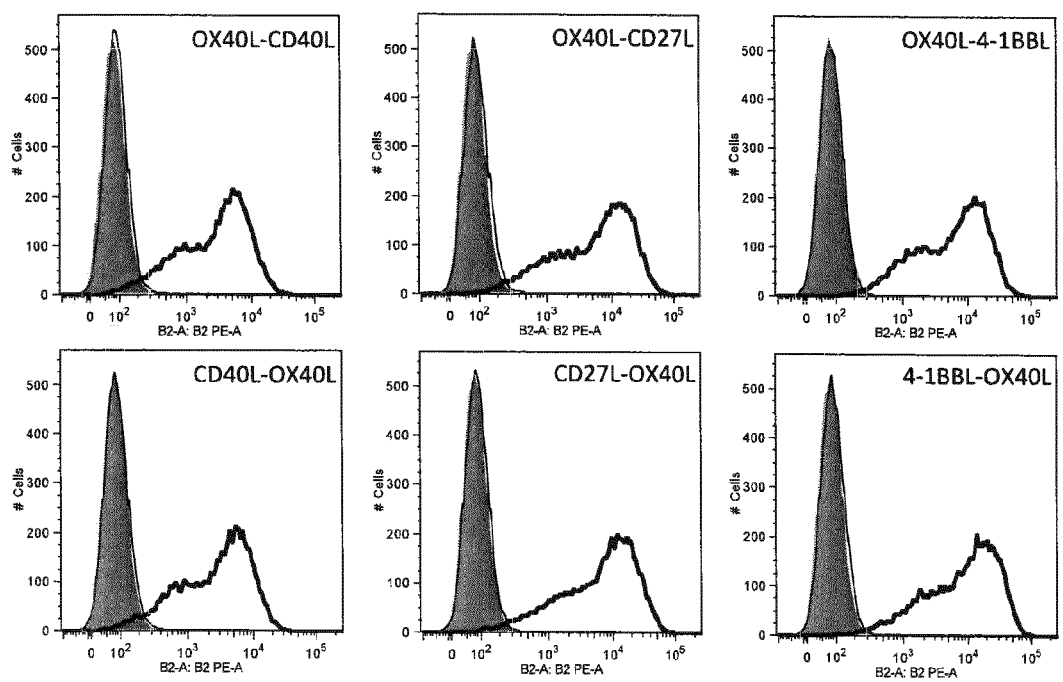
FIG. 7B

HT1080-CD40
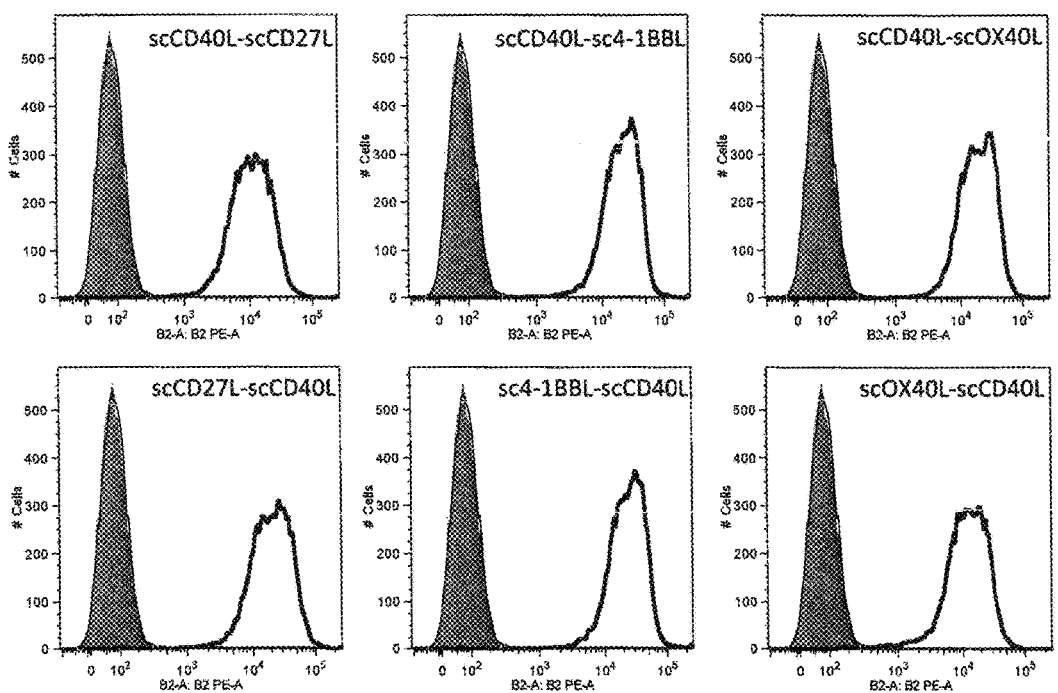
HT1080-CD27
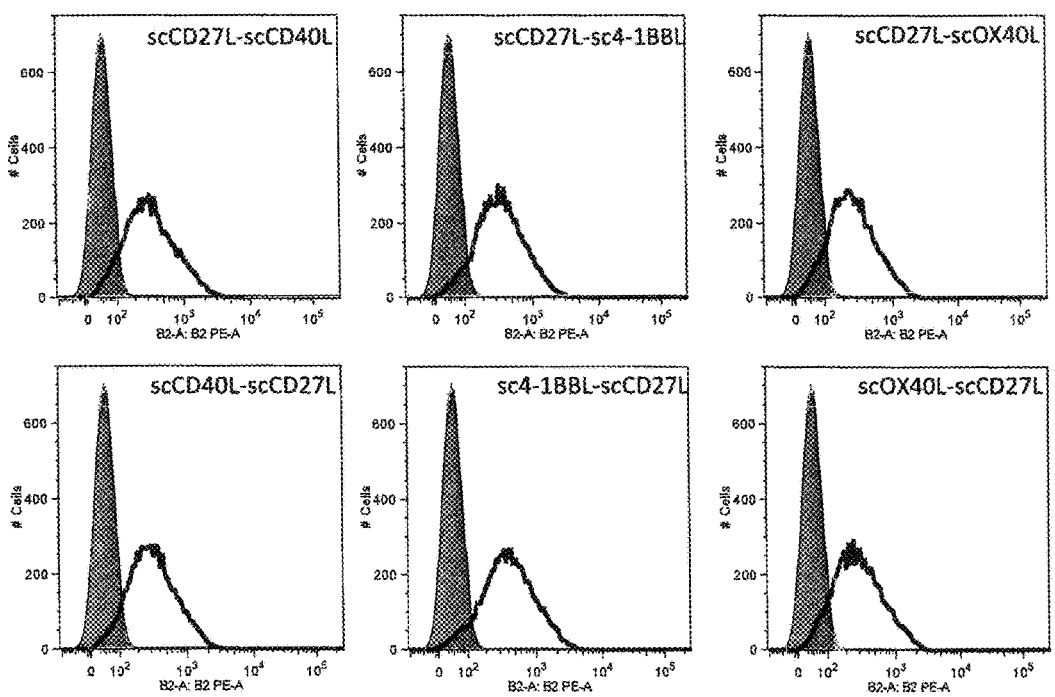
FIG. 12A

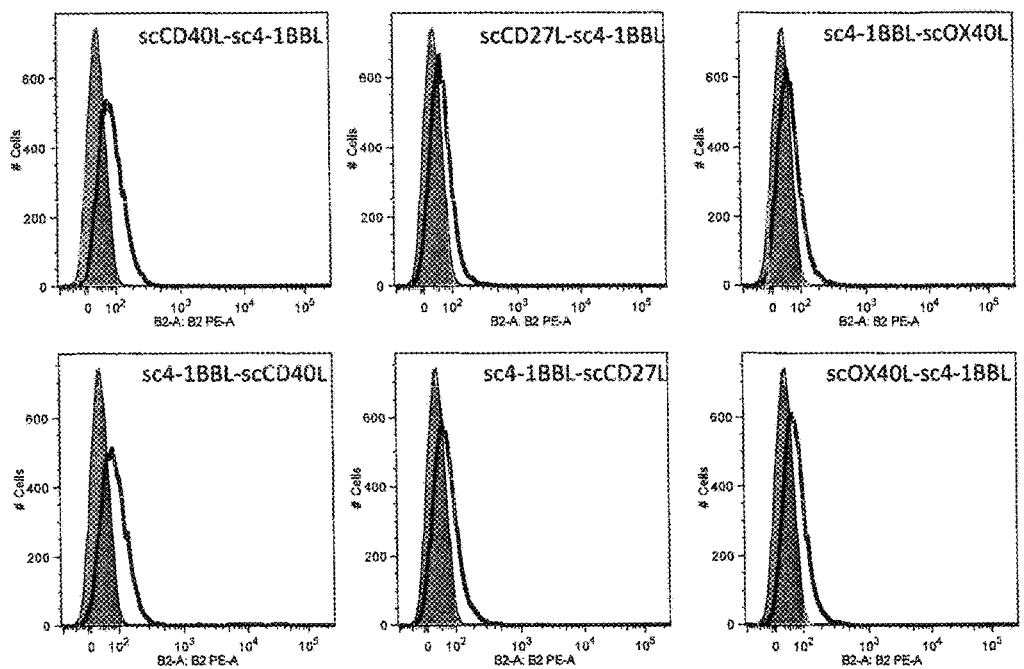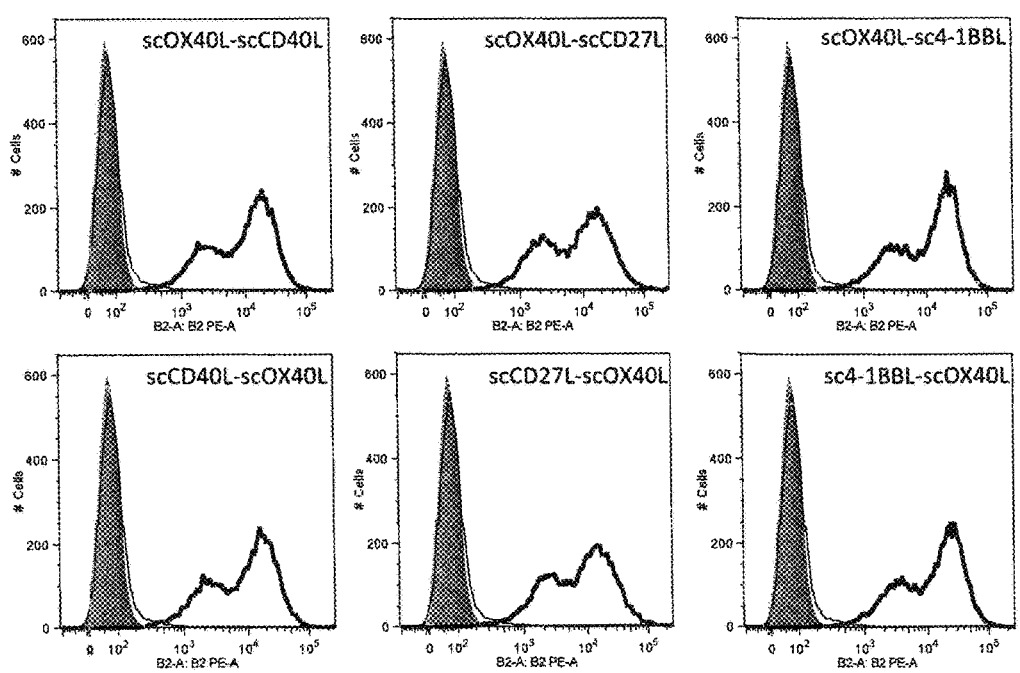
FIG. 12B

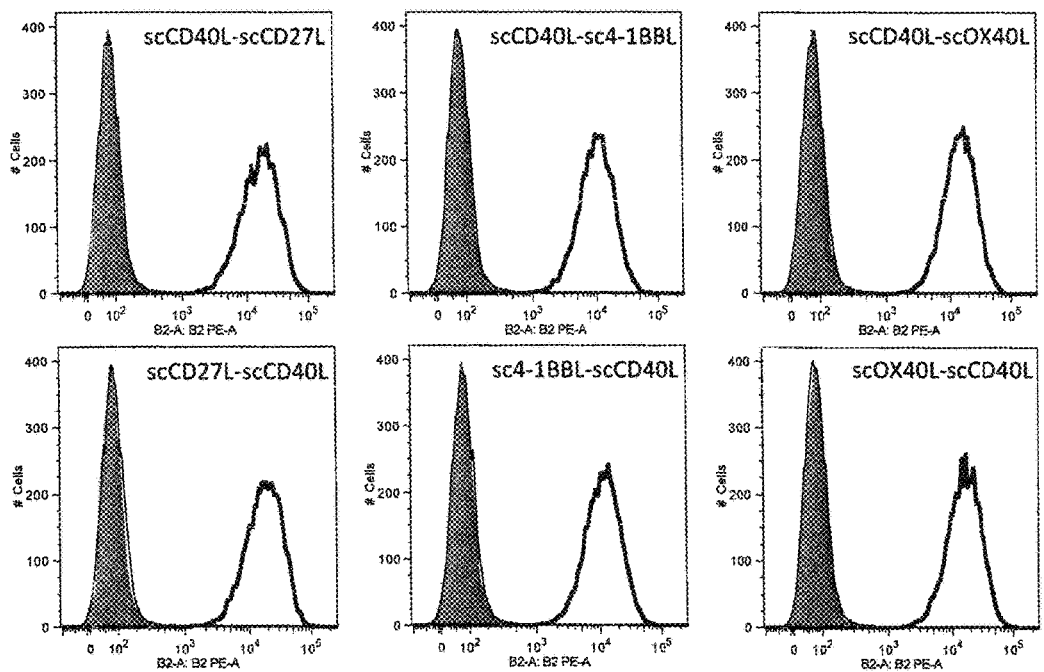
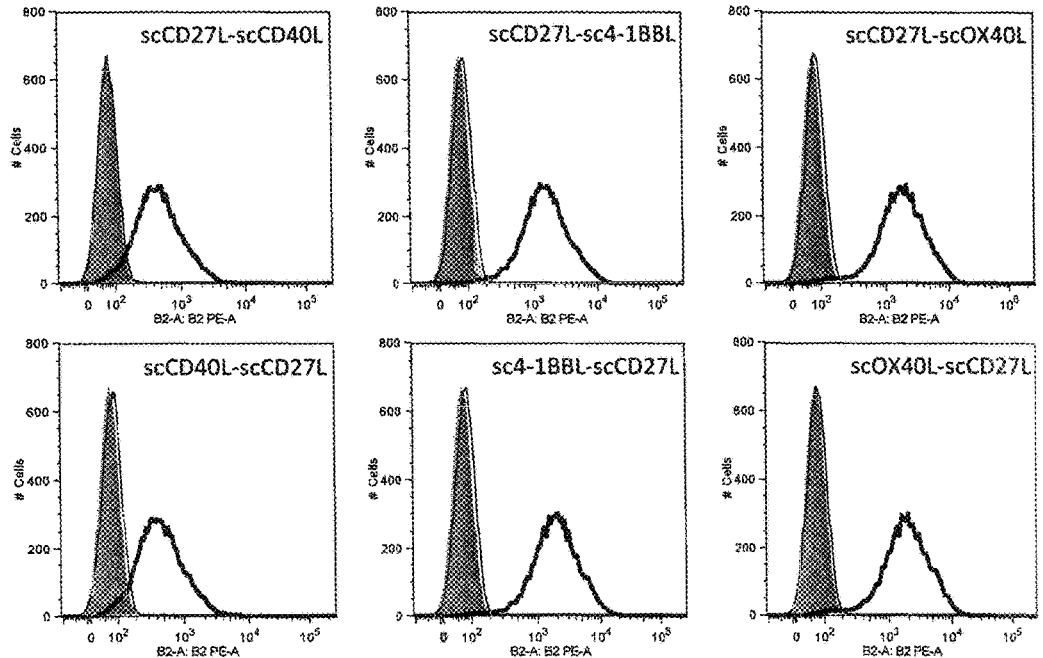
FIG. 13A

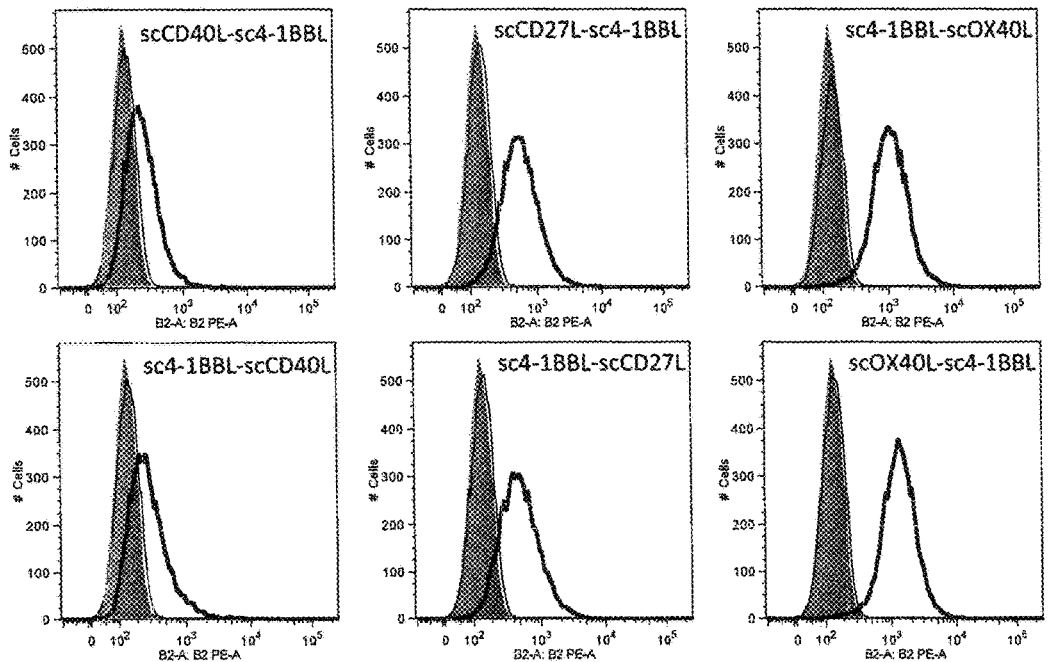
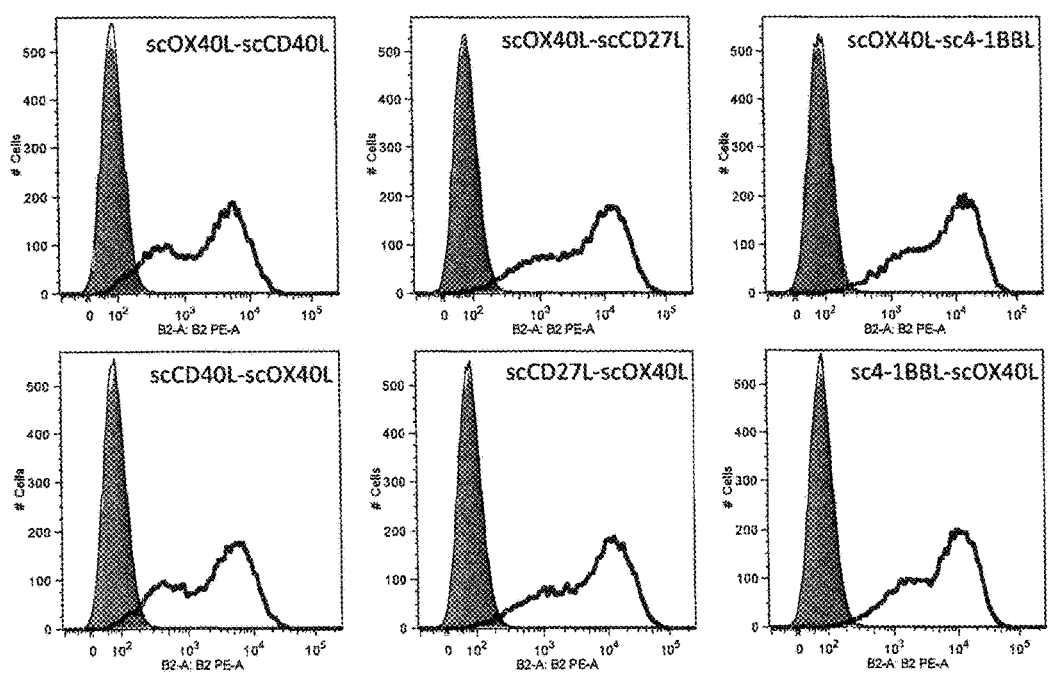
FIG. 13B

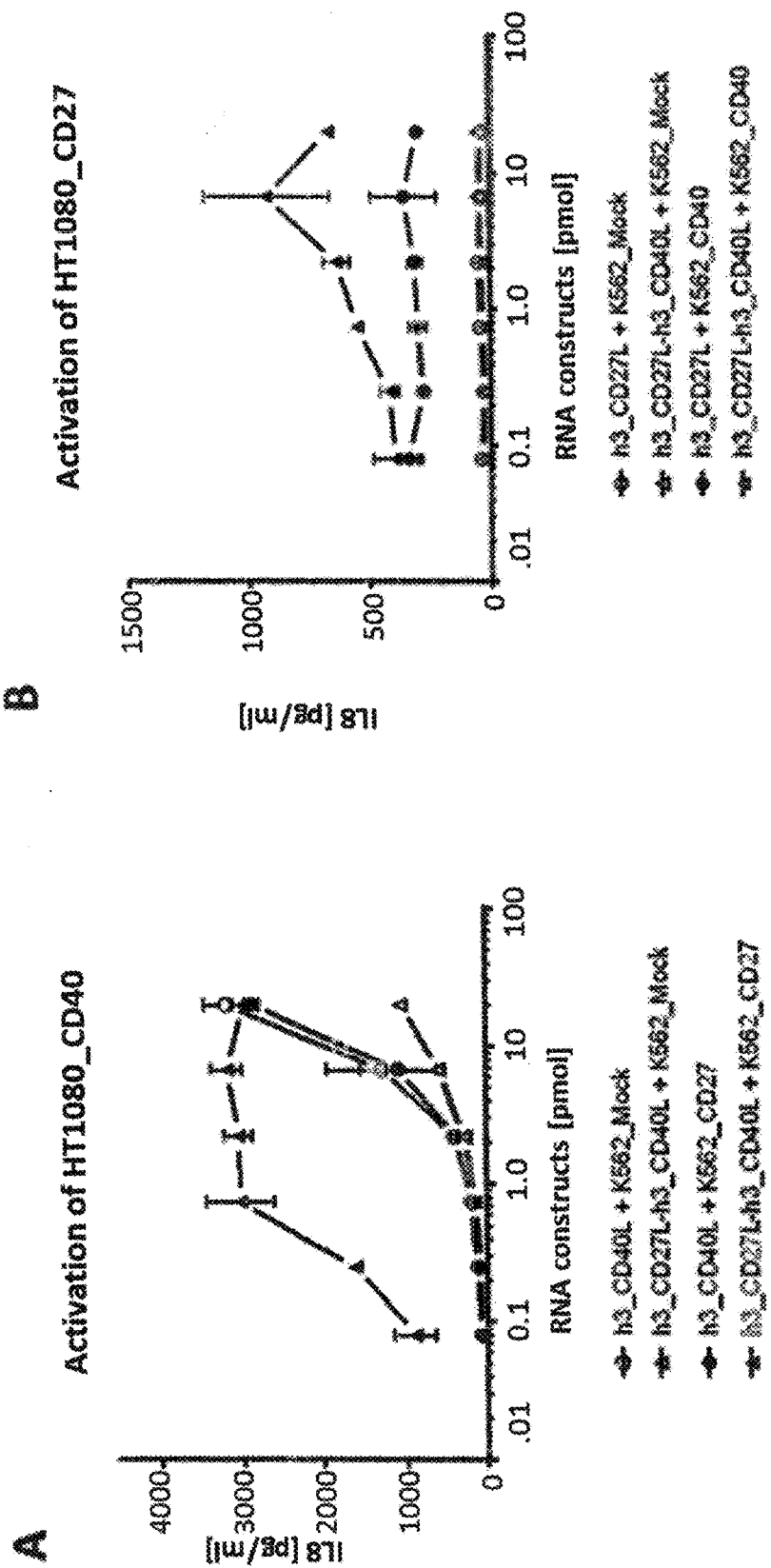
FIG. 25(A,B)

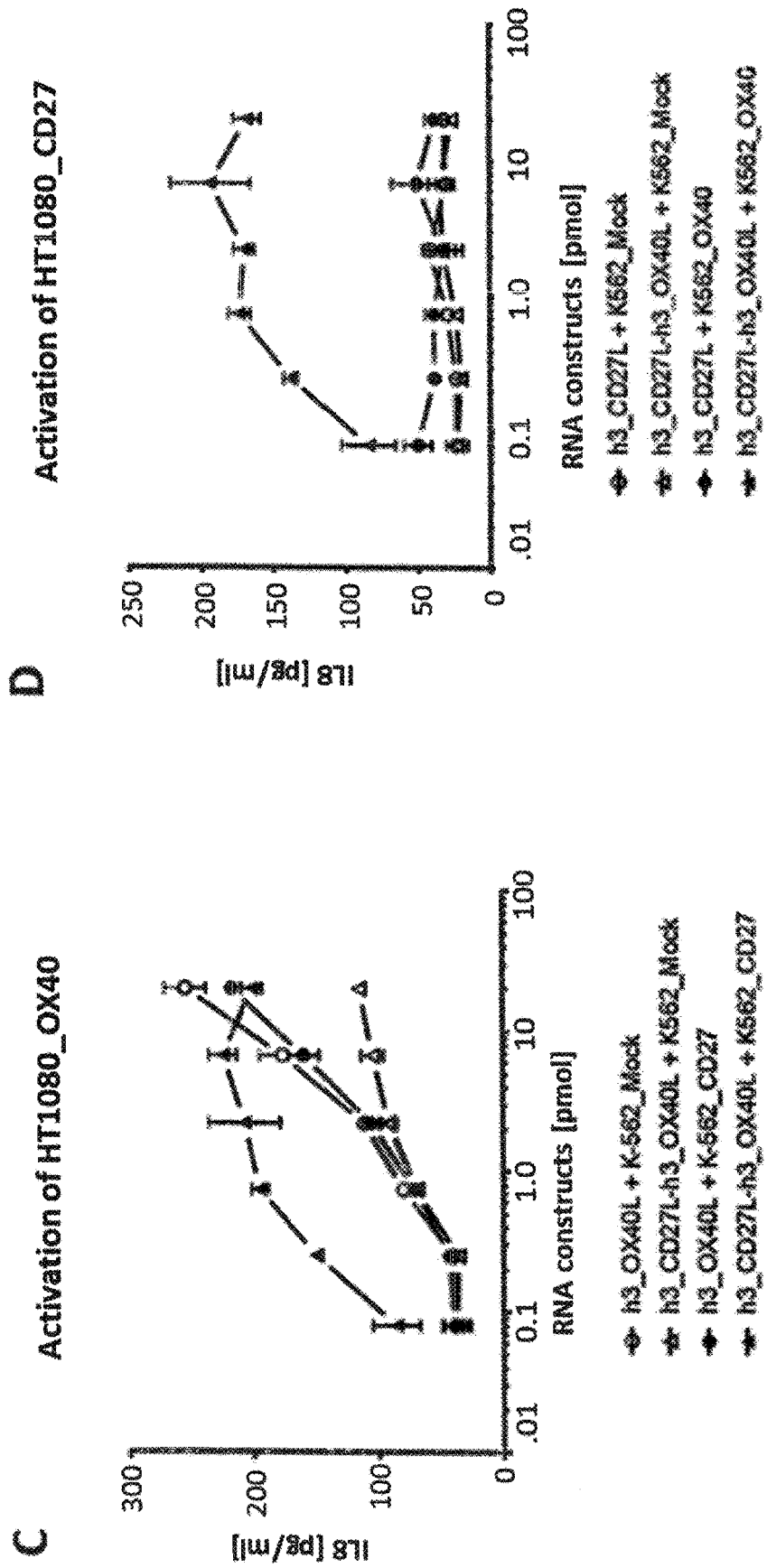
FIG. 25(C,D)

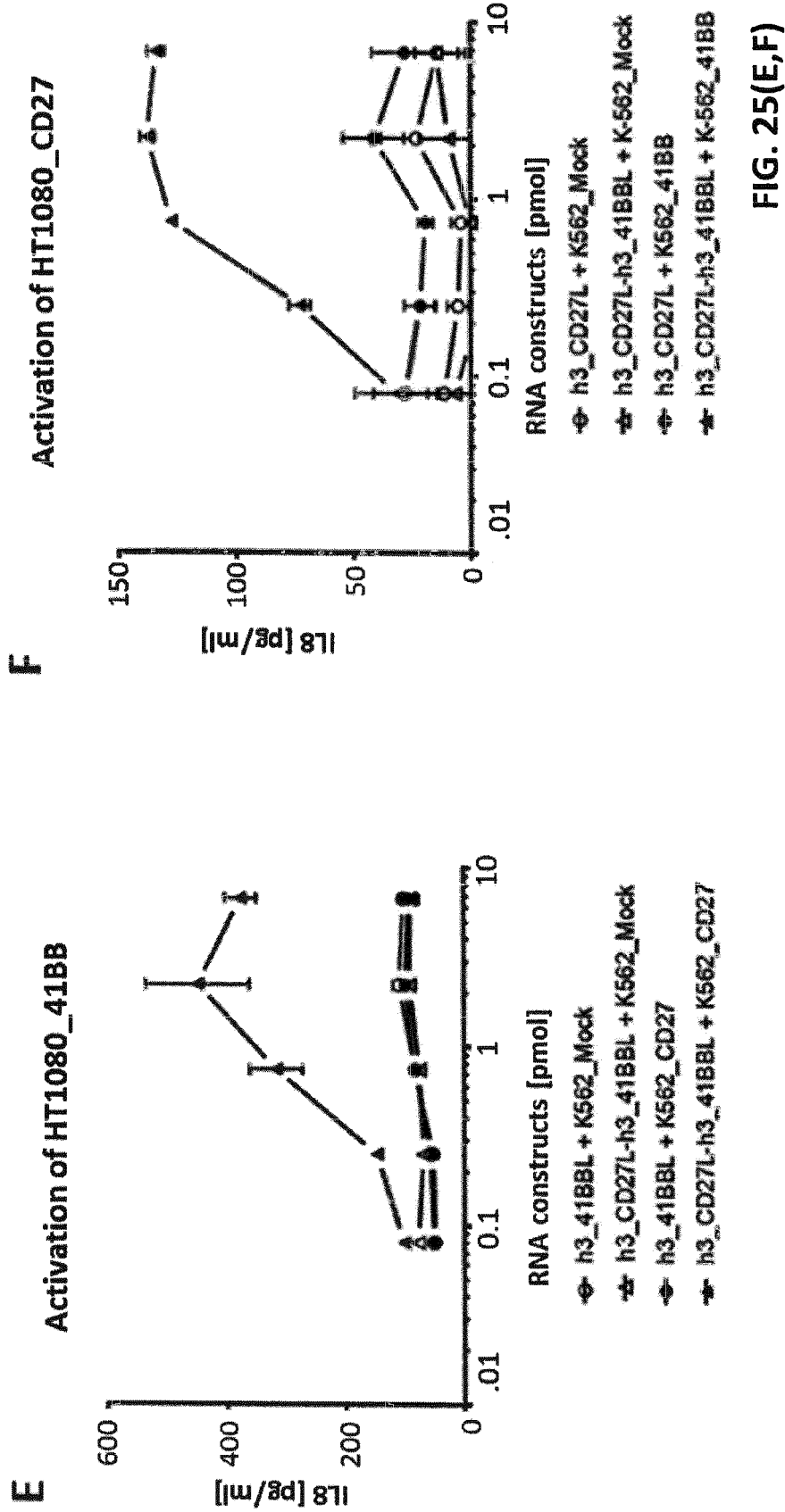
FIG. 25(E,F)

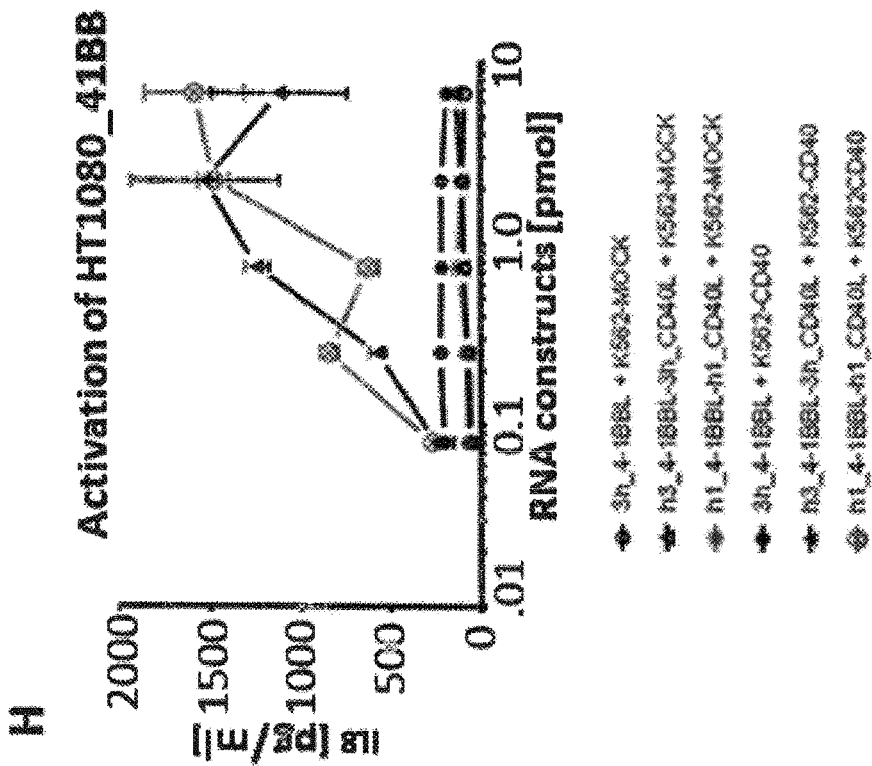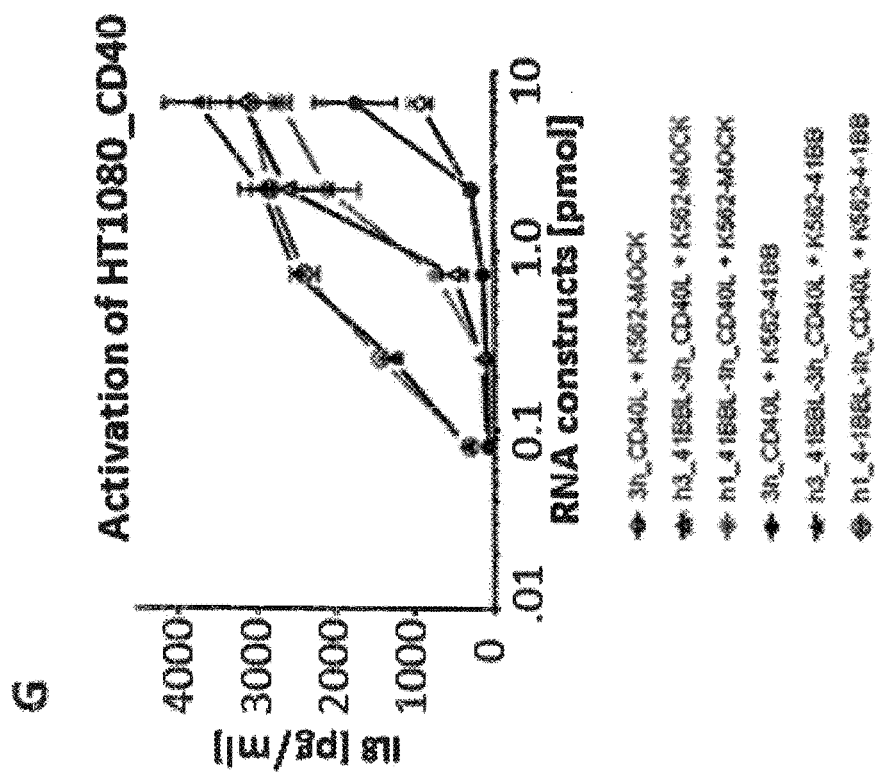
FIG. 25 (G,H)

FIG. 30A
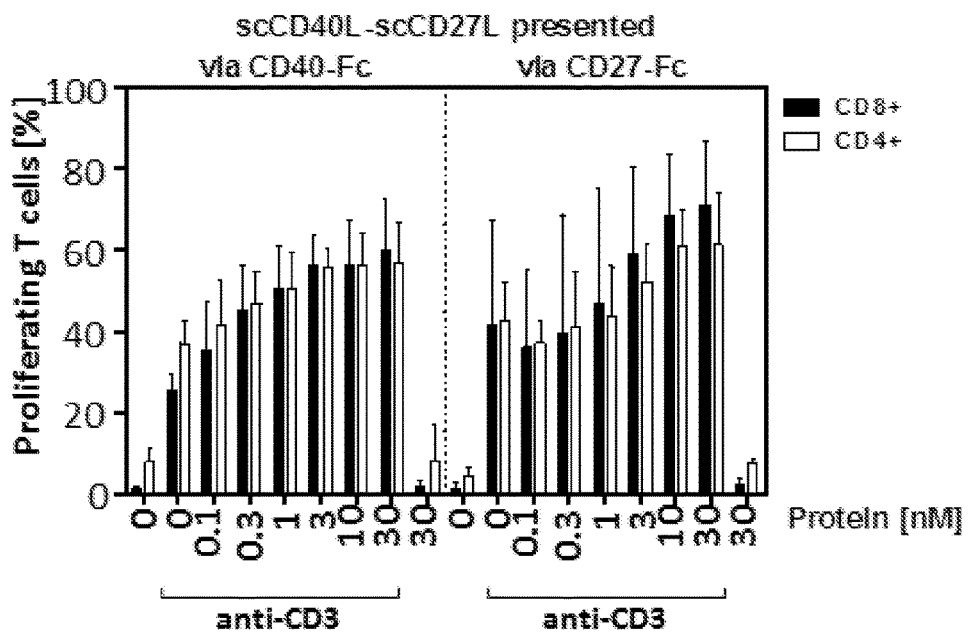
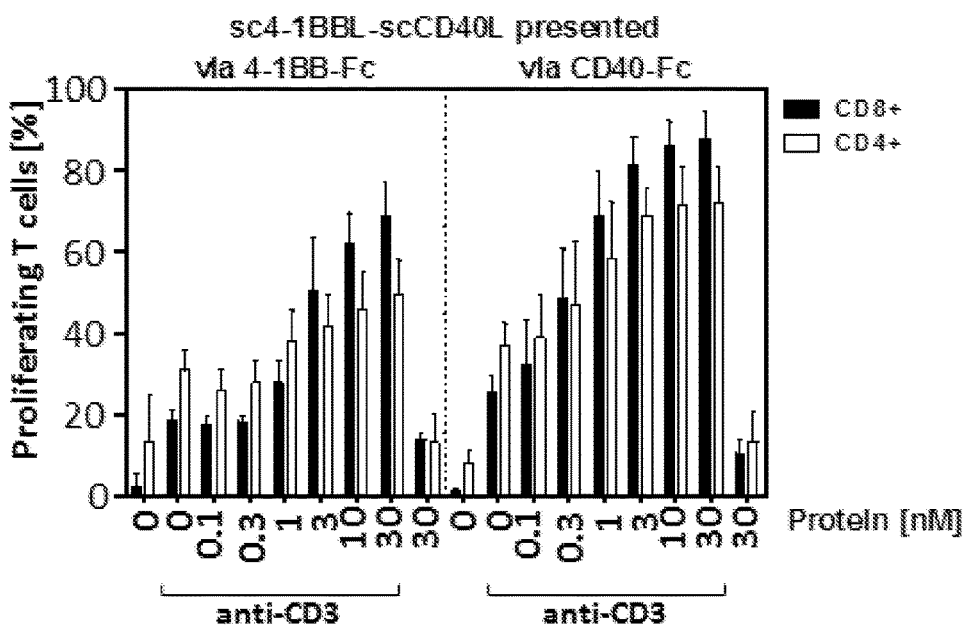
FIG. 30B

FIG. 30C
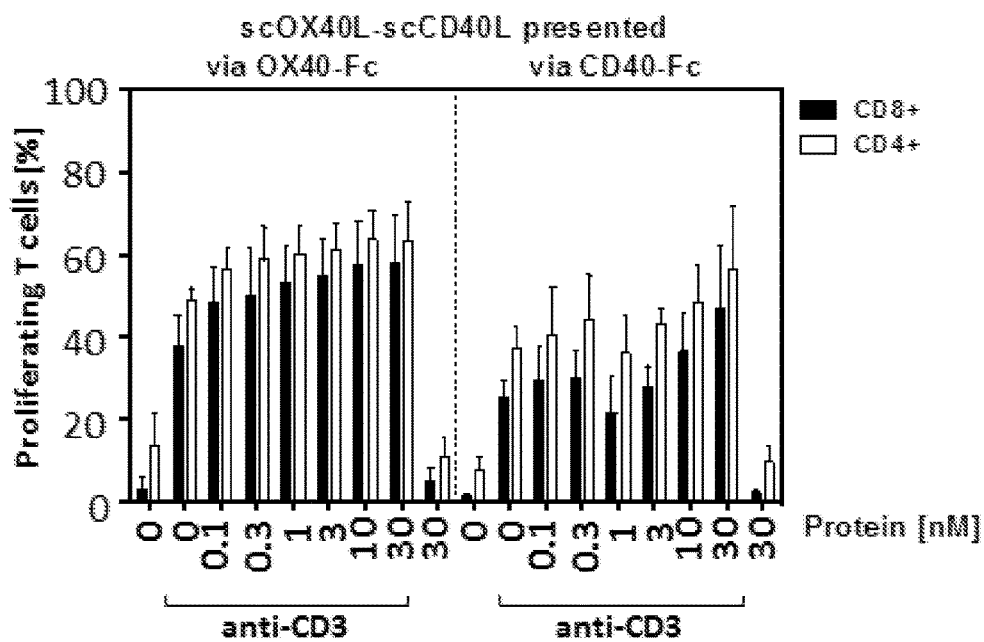
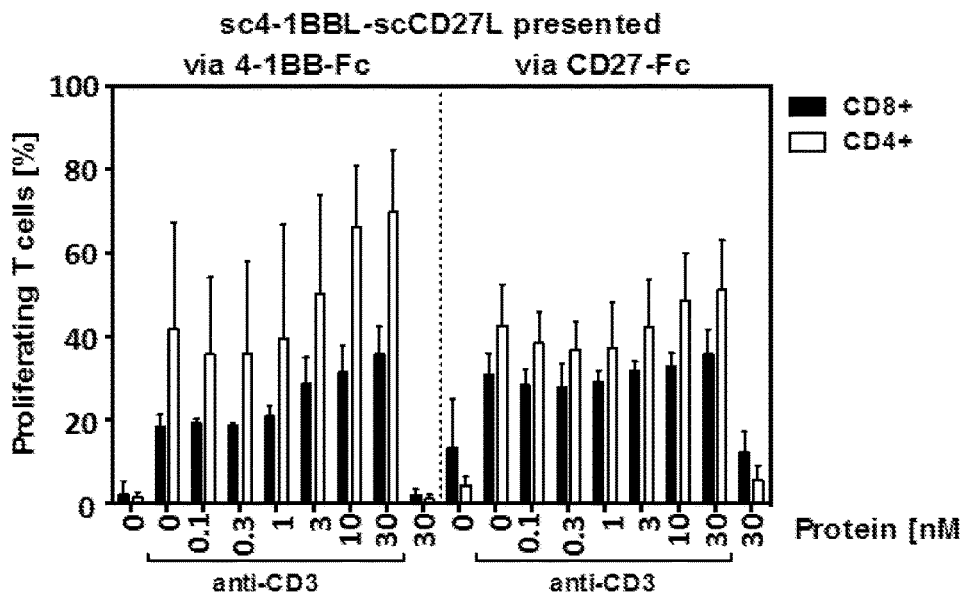
FIG. 30D

CYTOKINE FUSION PROTEINS

This is the US national phase under 35 U.S.C. § 371 of international application PCT/EP2016/050773, filed Jan. 15, 2016, which claims priority to international application PCT/EP2015/050682, filed Jan. 15, 2015.

TECHNICAL FIELD OF THE INVENTION

The present invention relates to cytokine fusion proteins and to nucleic acid molecules encoding such cytokine fusion proteins. The present invention further relates to cells, non-human organisms, pharmaceutical compositions and kits comprising the cytokine fusion proteins or the nucleic acid molecules encoding them, as well as to their use as medicaments.

BACKGROUND OF THE INVENTION

Ligands of the tumor necrosis factor (TNF) superfamily have important roles in normal development processes including apoptosis, regulation of immune cell functions and other cell type-specific responses. They also play a significant role in various acquired and genetic diseases, including cancer and autoimmune diseases.

The TNF ligand family is characterized by a conserved extracellular C-terminal domain referred to as TNF homology domain (THD) (Bodmer, J. L. et al. (2002), TRENDS in Biochemical Sciences, 27(1):19-26). The THDs, which share a virtually identical tertiary fold and exhibit a sequence identity between family members of approx. 20 to 30%, are responsible for receptor binding and non-covalently interact to form (homo-)trimeric complexes which are then recognized by their specific receptors. Although most ligands are synthesized as membrane-bound proteins, more specifically type II (i.e., intracellular N-terminus and extracellular C-terminus) transmembrane proteins, soluble cytokines can be generated by proteolytic cleavage of the extracellular domains comprising the THD (Bodmer, J. L. et al. (2002), TRENDS in Biochemical Sciences, 27(1):19-26).

It was an object of the present invention to provide multifunctional, in particular bifunctional or dual-acting, cytokine fusion proteins comprising at least two different cytokines. It was a further object of the present invention to provide nucleic acid molecules, in particular RNA molecules, encoding such cytokine fusion proteins.

SUMMARY OF THE INVENTION

In one aspect, the present invention relates to a cytokine fusion protein comprising (i) three extracellular domains or fragments or variants thereof of a first ligand of the tumor necrosis factor (TNF) superfamily forming a first homotrimer capable of binding to a receptor of the first ligand and (ii) three extracellular domains or fragments or variants thereof of a second ligand of the TNF superfamily forming a second homotrimer capable of binding to a receptor of the second ligand, wherein the first ligand and the second ligand are different, and wherein the first homotrimer and the second homotrimer are covalently linked, preferably via one or more peptide linkers.

In one embodiment, the three extracellular domains or fragments or variants thereof of the first ligand and/or the three extracellular domains or fragments or variants thereof of the second ligand are covalently linked.

In one embodiment, the cytokine fusion protein comprises a molecule/structure having the general formula $$\text{N'-A-}L_A\text{-A-}L_A\text{-A-L-B-}L_B\text{B-}L_B\text{-B-C'} \qquad \text{(Formula I)},$$

wherein A comprises the extracellular domain or a fragment or a variant thereof of the first ligand, and B comprises the extracellular domain or a fragment or variant thereof of the second ligand, and wherein L comprises a peptide linker, and $L_A$ and $L_B$ are, at each occurrence, independently selected from a covalent bond and a peptide linker.

In one embodiment, L further comprises a multimerization domain, preferably a dimerization domain, allowing the multimerization, preferably dimerization, of the cytokine fusion protein.

In one embodiment, the dimerization domain is selected from the group consisting of an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an Fc domain, an uteroglobin dimerization domain and functional variants of any one of the foregoing. In one embodiment, the cytokine fusion protein is present as a multimeric, preferably dimeric, complex.

In another embodiment, the cytokine fusion protein comprises at least one, preferably three, subunits with the general formula:

$$\text{N'-A-L-B-C'} \qquad \text{(Formula II)},$$

wherein A comprises the extracellular domain or a fragment or variant thereof of the first ligand, and B comprises the extracellular domain or a fragment or variant thereof of the second ligand, wherein L comprises a peptide linker, and wherein, preferably, the three subunits form the cytokine fusion protein.

In another aspect, the present invention relates to a cytokine fusion protein comprising a first block comprising three extracellular domains or fragments or variants thereof of a first ligand of the tumor necrosis factor (TNF) superfamily which are covalently linked and a second block comprising three extracellular domains or fragments or variants thereof of a second ligand of the TNF superfamily which are covalently linked, wherein the first ligand and the second ligand are different, and wherein the first block and the second block are covalently linked.

In one embodiment, the three extracellular domains or fragments or variants thereof of the first ligand form a first homotrimer capable of binding to a receptor of the first ligand, and the three extracellular domains or fragments or variants thereof of the second ligand form a second homotrimer capable of binding to a receptor of the second ligand.

In one embodiment, the three extracellular domains of the first ligand and/or the three extracellular domains of the second ligand and/or the first block and the second block are covalently linked via peptide linkers.

In one embodiment, the cytokine fusion protein comprises a molecule/structure having the general formula $$\text{N'-A-}L_A\text{-A-}L_A\text{-A-L-B-}L_B\text{B-}L_B\text{-B-C'} \qquad \text{(Formula I)},$$

wherein A comprises the extracellular domain or a fragment or variant thereof of the first ligand, and B comprises the extracellular domain or a fragment or variant thereof of the second ligand, and wherein L comprises a peptide linker, and $L_A$ and $L_B$ are, at each occurrence, independently selected from a covalent bond and a peptide linker.

In one embodiment, L further comprises a multimerization domain, preferably a dimerization domain, allowing the multimerization, preferably dimerization, of the cytokine fusion protein.

In one embodiment, the dimerization domain is selected from the group consisting of an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an Fc domain, an uteroglobin dimerization domain and functional variants of any one of the foregoing.

In one embodiment, the cytokine fusion protein is present as a multimeric, preferably dimeric, complex.

In another aspect, the present invention relates to a cytokine fusion protein comprising the extracellular domain or a fragment or variant thereof of a first ligand of the tumor necrosis factor (TNF) superfamily and the extracellular domain or a fragment or variant thereof of a second ligand of the TNF superfamily, wherein the first ligand and the second ligand are different, and wherein the extracellular domains or fragments or variants thereof are covalently linked.

In one embodiment, the extracellular domains are covalently linked via a peptide linker.

In one embodiment, the cytokine fusion protein comprises a molecule/structure having the general formula:

$$N'\text{-}A\text{-}L\text{-}B\text{-}C' \qquad \text{(Formula II)},$$

wherein A comprises the extracellular domain or a fragment or variant thereof of the first ligand, and B comprises the extracellular domain or a fragment or variant thereof of the second ligand, and wherein L comprises a peptide linker.

In one embodiment, the cytokine fusion protein is present as a trimeric complex, wherein three extracellular domains or fragments or variants thereof of the first ligand form a first homotrimer capable of binding to a receptor of the first ligand, and three extracellular domains or fragments or variants thereof of the second ligand form a second homotrimer capable of binding to a receptor of the second ligand.

According to the present invention, the first ligand and the second ligand referred to herein are preferably selected from the group consisting of CD40L, CD27L, 4-1BBL, OX40L, APRIL, CD30L, EDA-A1, EDA-A2, FasL, GITRL, LIGHT, LT-alpha, TL1A, TNF-alpha, TRAIL, RANKL, and TWEAK, more preferably from the group consisting of CD40L, CD27L, 4-1BBL, and OX40L.

In one embodiment,
the first ligand is CD40L, and the second ligand is CD27L;
the first ligand is CD27L, and the second ligand is CD40L;
the first ligand is CD40L, and the second ligand is 4-1BBL;
the first ligand is 4-1BBL, and the second ligand is CD40L;
the first ligand is CD27L, and the second ligand is 4-1BBL;
the first ligand is 4-1BBL, and the second ligand is CD27L;
the first ligand is CD40L, and the second ligand is OX40L;
the first ligand is OX40L, and the second ligand is CD40L;
the first ligand is CD27L, and the second ligand is OX40L;
the first ligand is OX40L, and the second ligand is CD27L;
the first ligand is OX40L, and the second ligand is 4-1BBL; or
the first ligand is 4-1BBL, and the second ligand is OX40L.

In one embodiment, the extracellular domain of CD40L comprises or consists of amino acid residues 51 to 261 or 116 to 261 of SEQ ID NO: 1, the extracellular domain of CD27L comprises or consists of amino acid residues 52 to 193 of SEQ ID NO: 2, the extracellular domain of 4-1BBL comprises or consists of amino acid residues 71 to 254 of SEQ ID NO: 3, and/or the extracellular domain of OX40L comprises or consists of amino acid residues 51 to 183 of SEQ ID NO: 4.

In one embodiment, the cytokine fusion protein further comprises at least one label or tag allowing the detection and/or isolation of the cytokine fusion protein.

In one embodiment, the cytokine fusion protein further comprises one or more modifications increasing the stability of the cytokine fusion protein.

In another aspect, the present relates to a nucleic acid molecule encoding a cytokine fusion protein as defined above or a subunit thereof.

In one embodiment, the nucleic acid molecule is operatively linked to an expression control sequence.

In one embodiment, the nucleic acid molecule is contained in a vector.

In one embodiment, the nucleic acid molecule is an RNA molecule, preferably an in vitro-transcribed (IVT) RNA molecule.

In another aspect, the present relates to a cell transformed or transfected with a nucleic acid molecule as defined above.

In one embodiment, the cell is a prokaryotic cell.

In one embodiment, the cell is a eukaryotic cell, preferably a mammalian cell, more preferably a human cell.

In another aspect, the present relates to a non-human organism transformed or transfected with a nucleic acid molecule as defined above.

In another aspect, the present relates to a pharmaceutical composition comprising, as an active agent, a cytokine fusion protein as defined above, a nucleic acid molecule as defined above, or a cell as defined above.

In one embodiment, the pharmaceutical composition further comprises a pharmaceutically acceptable carrier and/or excipient.

In another aspect, the present relates to a kit comprising a cytokine fusion protein as defined above, a nucleic acid molecule as defined above, a cell as defined above or a pharmaceutical composition as defined above.

In another aspect, the present relates to a cytokine fusion protein as defined above, a nucleic acid molecule as defined above, a cell as defined above, or a pharmaceutical composition as defined above for use as a medicament.

In another aspect, the present relates to a cytokine fusion protein as defined above, a nucleic acid molecule as defined above, a cell as defined above, or a pharmaceutical composition as defined above for use in the treatment of a disease selected from the group consisting of cancer, infectious diseases, inflammatory diseases, metabolic diseases, autoimmune disorders, degenerative diseases, apoptosis-associated diseases and transplant rejections.

In another aspect, the present relates to the use of a cytokine fusion protein as defined above, a nucleic acid molecule as defined above, a cell as defined above, or a pharmaceutical composition in the manufacture of a medicament for the treatment of a disease selected from the group consisting of cancer, infectious diseases, inflammatory diseases, metabolic diseases, autoimmune disorders, degenerative diseases, apoptosis-associated diseases and transplant rejections.

In another aspect, the present relates to a method of treatment of a disease selected from the group consisting of cancer, infectious diseases, inflammatory diseases, metabolic diseases, autoimmune disorders, degenerative diseases, apoptosis-associated diseases and transplant rejections, said method comprising administering an effective amount of a cytokine fusion protein as defined above, a nucleic acid molecule as defined above, a cell as defined above, or a pharmaceutical composition as defined above to a subject in need thereof.

DESCRIPTION OF THE FIGURES

FIGS. 6 A and B. Binding of Duokines (100 nM) to CD40-, CD27-, 4-1BB- and OX40-expressing HT1080 cells analyzed by flow cytometry. Bound Duokines were detected with a PE-labeled anti-FLAG antibody (grey, cells alone; thin line cells incubated with PE-labeled anti-FLAG antibody; bold line, cells incubated with Duokines).

FIGS. 7 A and B. Bispecificity of Duokines was analyzed by flow cytometry. After binding of Duokines (100 nM) to CD40-, CD27-, 4-1BB- and OX40-expressing HT1080 cells, the Duokines were detected using the corresponding receptor-Fc fusion proteins (10 nM) and a PE-labeled anti-human Fc antibody. TNFR1-Fc was included as negative control (grey, cells incubated with PE-labeled anti-human Fc antibody; thin line, cells incubated with Duokines and TNFR1-Fc; bold line, cells incubated with CD40-, CD27-, 4-1BB- or OX40-Fc).

FIGS. 12 A and B. Binding of single-chain Duokines (100 nM) to CD40-, CD27-, 4-1BB- and OX40-expressing HT1080 cells analyzed by flow cytometry. Bound single-chain Duokines were detected with a PE-labeled anti-FLAG antibody (grey, cells alone; thin line cells incubated with PE-labeled anti-FLAG antibody; bold line, cells incubated with single-chain Duokines).

FIGS. 13 A and B. Bispecificity of single-chain Duokines was analyzed by flow cytometry. After binding of single-chain Duokines (100 nM) to CD40-, CD27-, 4-1BB- and OX40-expressing HT1080 cells, the single-chain Duokines were detected using the corresponding receptor-Fc fusion proteins (10 nM) and a PE-labeled anti-human Fc antibody. TNFR1-Fc was included as negative control (grey, cells incubated with PE-labeled anti-human Fc antibody; thin line, cells incubated with single-chain Duokines and TNFR1-Fc; bold line, cells incubated with single-chain Duokines and CD40-, CD27-, 4-1BB- or OX40-Fc).

FIGS. 25 A-H. Enhanced TNF-receptor activation by TNFL(1)-TNFL(2)-fusion constructs under trans-presentation settings. K562 cells were electroporated in a multi-well electroporation plate (96-well) with different amounts of IVT-RNA encoding extracellular domains of TNFR ligands or fusion proteins thereof. RNA-amounts are indicated as pmol of RNA with reference to the corresponding encoded protein. After overnight incubation, supernatants were transferred to confluent cell layers of the two corresponding stable TNF-receptor transfectants of the HT1080 cell line (see FIG. 24A). K562 cells, either MOCK-electroporated (as control) or electroporated with the corresponding TNF-receptor-plasmids on the one day before, were added to confluent cell layers of HT1080-TNFR-transfectants and supernatants in order to generate trans-presentation settings (cell to cell transactivation) for fusion proteins. After 8 hours of co-incubation, cell-free supernatants were collected, and concentrations of IL-8 were measured, which is released by HT1080 cells upon TNF-receptor dependent NF-kappaB activation. (A) shows IL-8 release due to activation of HT1080_CD40 upon incubation with supernatants from K562 cells electroporated with IVT-RNA encoding h3_CD27L-h3_CD40L. h3_CD40L single constructs and the fusion construct h3_CD27L-h3_CD40L without trans-presentation (+K562_MOCK) resulted in IL-8-secretion upon electroporation of at least 1 pmol RNA with reference to the encoded proteins. Under trans-presentation conditions mediated by K562_CD27 the fusion construct h3_CD27L-h3_CD40L induced CD40 activation to the same extent with about 100-fold less amount of IVT-RNA with reference to the encoded protein. (B) CD27-activation upon electroporation of IVT-RNAs encoding h3_CD27L or h3_CD27L-h3_CD40L without trans-presentation conditions was not detected by measuring IL-8 secretion. With trans-presentation by K562_CD40, CD27-activation was detected upon K562-electroporation of h3_CD27L-h3_CD40L fusion construct. (C) shows IL-8 release due to activation of HT1080_OX40 upon incubation with supernatants of IVT-RNA encoding h3_CD27L-h3_OX40L. h3_OX40L single constructs and the fusion construct h3_CD27L-h3_OX40L without trans-presentation (+K562_MOCK) resulted in IL-8-secretion upon electroporation of about 1 pmol RNA and more with reference to the encoded proteins. Under trans-presentation conditions mediated by K562_CD27, the fusion construct h3_CD27L-h3_OX40L induced CD40 activation to the same extent with about 10-fold less amount of IVT-RNA with reference to the encoded protein. (D) CD27-activation upon electroporation of IVT-RNAs encoding h3_CD27L or h3_CD27L-h3_OX40L without trans-presentation conditions was not detected by measuring IL-8 secretion. With trans-presentation by K562_OX40 CD27-activation was detected upon K562-electroporation of h3_CD27L-h3_CD40L RNA constructs. (E) shows IL-8 concentration due to activation of HT1080_CD27 upon incubation with supernatants of IVT-RNA encoding h3_CD27L-h3_4-1BBL. h3_CD27L single constructs and the fusion construct h3_CD27L-h3_4-1BBL without trans-presentation (+K562_MOCK) did not induce IL-8-secretion. Under trans-presentation conditions mediated by K562_4-1BB the fusion construct h3_CD27L-h3_4-1BBL induced activation of CD27. (F) h3_4-1BBL single constructs and the fusion construct h3_CD27L-h3_4-1BBL without trans-presentation (+K562_MOCK) did not induce IL-8-secretion. Under trans-presentation conditions mediated by K562_CD27 the fusion construct h3_CD27L-h3_4-1BBL induced activation of 4-1BB. (G) shows IL-8 release due to activation of HT1080_CD40 upon incubation with supernatants from K562 electroporated with IVT-RNA encoding h3_41BBL-h3_CD40L and h1_41BBL-h1_CD40L. h3_CD40L single constructs and both fusion construct without trans presentation (+K562_MOCK) resulted in IL-8-secretion upon electroporation of at least 1 pmol RNA with reference to the encoded proteins. Under trans-presentation conditions mediated by K56241BB both fusion constructs, h3_41BBL-h3_CD40L and h1_41BBL-h1_CD40L, induced CD40 activation to the same extent with about 10-fold less amount of IVT-RNA (with reference to the encoded protein). (H) h3_4-1BBL single constructs and both fusion constructs, h3_41BBL-h3_CD40L and h1_41BBL-h1_CD40L, without trans-presentation (+K562_MOCK) did not induce IL-8-secretion. Under trans-presentation conditions mediated by K562_CD40 both fusion constructs induced activation of 4-1BB to the same extent.

FIGS. 30A-E. Simultaneous binding of single-chain duokines to immobilized receptor and PBMCs leading to activation and proliferation of T cells. 200 ng/well receptor-Fc were immobilized on microtiter plates overnight at 4° C. Residual binding sites were blocked with RPMI 1640+10% FCS for 1 h. Serial dilutions of scDuokines were incubated with the immobilized receptors for 1 h, and subsequently unbound proteins were washed away. 1.5×10$^5$ CFSE-stained human PBMCs (bulk population) were added to the microtiter plate in presence (or absence) of cross-linked anti-human CD3 antibody as primary suboptimal stimulus. After 6 days, proliferation of CD4 and CD8 T cells was assessed in flow cytometry by CFSE dilution.

DETAILED DESCRIPTION OF THE INVENTION

Figure 1:
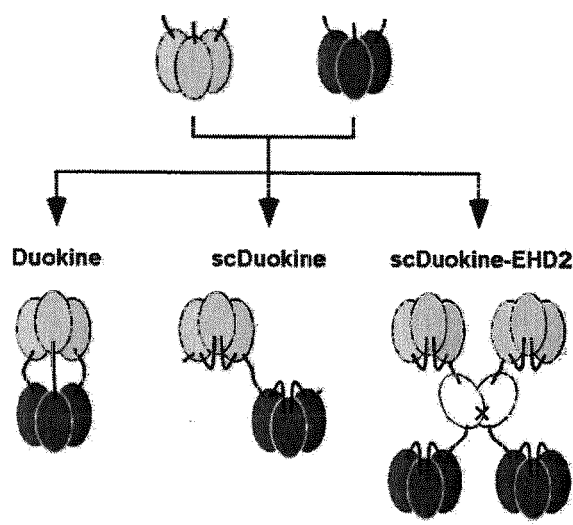
FIG. 1. Schematic assembly of Duokines, scDuokines and EHD2-scDuokines.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "cytokine" generally refers to proteins that are important in cell signaling and act through receptors. In the context of the present invention, the term particularly refers to ligands of the TNF superfamily, more particularly the extracellular domain of these ligands which forms soluble active homotrimers.

The term "ligand of the TNF superfamily", as used herein, also includes variants of a given ligand of the TNF superfamily provided these variants are functional, more particularly have an extracellular domain which is able to form a homotrimer capable of binding to a receptor of the ligand.

The term "variant of a ligand of the TNF superfamily" according to the invention, refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant of a ligand of the TNF superfamily" shall encompass any posttranslationally modified variants and conformation variants.

According to the present invention, the first ligand and the second ligand of the TNF superfamily are preferably selected from the group consisting of CD40L, CD27L, 4-1BBL, OX40L, APRIL, CD30L, EDA-A1, EDA-A2, FasL, GITRL, LIGHT, LT-alpha, TL1A, TNF-alpha, TRAIL, RANKL, and TWEAK, more preferably from the group consisting of CD40L, CD27L, 4-1BBL, and OX40L.

CD40 ligand (CD40L) is also known as CD154, TNFSF5, TRAP or gp39 and is a type II transmembrane glycoprotein belonging to the TNF superfamily. In one embodiment, the term CD40L, as used herein, refers to human CD40L. The UniProt accession number of human CD40L is P29965. In one embodiment, CD40L has the amino acid sequence of SEQ ID NO: 1.

CD27 ligand (CD27L) is also known as CD70 or TNFSF7 and is a type II transmembrane glycoprotein belonging to the TNF superfamily. In one embodiment, the term CD27L, as used herein, refers to human CD27L. The UniProt accession number of human CD27L is P32970. In one embodiment, CD27L has the amino acid sequence of SEQ ID NO: 2.

4-1BB ligand (4-1BBL) is a type II transmembrane glycoprotein belonging to the TNF superfamily and is also referred to as TNFSF9. In one embodiment, the term 4-1BBL, as used herein, refers to human 4-1BBL. The UniProt accession number of human 4-1BBL is P41273. In one embodiment, 4-1BBL has the amino acid sequence of SEQ ID NO: 3.

OX40 ligand (OX40L), also known as gp34 or TNFSF4, is a type II transmembrane glycoprotein belonging to the TNF superfamily. In one embodiment, the term OX40L, as used herein, refers to human OX40L. The UniProt accession number of human OX40L is P23510. In one embodiment, OX40L has the amino acid sequence of SEQ ID NO: 4.

A proliferation-inducing ligand (APRIL), also known as TALL-2, TRDL-1 or TNFSF13, is a type II transmembrane protein that is a member of the TNF superfamily. In one embodiment, the term APRIL, as used herein, refers to human APRIL. The UniProt accession number of human APRIL is O75888.

CD30 ligand (CD30L), also known as TNFSF8, is a type II membrane protein belonging to the TNF superfamily. In one embodiment, the term CD30L, as used herein, refers to human CD30L. The UniProt accession number of human CD30L is P32971.

Ectodysplasin-A1 (EDA-A1) is a type II transmembrane protein belonging to the TNF superfamily. It is a splice variant of Ectodysplasin-A (EDA). In one embodiment, the term EDA-A1, as used herein, refers to human EDA-A1. The UniProt accession number of human EDA-A1 is Q92838-1.

Ectodysplasin-A2 (EDA-A2) is a type II transmembrane protein belonging to the TNF superfamily. It is a splice variant of Ectodysplasin-A (EDA). In one embodiment, the term EDA-A2, as used herein, refers to human EDA-A2. The UniProt accession number of human EDA-A2 is Q92838-3.

Fas ligand (FasL) is also known as CD95L or TNFSF6 and is a type II transmembrane protein belonging to the TNF superfamily. In one embodiment, the term FasL, as used herein, refers to human FasL. The UniProt accession number of human FasL is P48023.

GITR ligand (GITRL) is a type II transmembrane protein belonging to the TNF superfamily and has been designated TNFSF18. In one embodiment, the term GITRL, as used herein, refers to human GITRL. The UniProt accession number of human GITRL is Q9UNG2.

LIGHT is also known as HVEML or TNFSF14 and is a type II transmembrane protein belonging to the TNF superfamily. In one embodiment, the term LIGHT, as used herein, refers to human LIGHT. The UniProt accession number of human LIGHT is O43557.

Lymphotoxin-alpha (LT-alpha) is also known as TNF-beta or TNFSF1 and is a member of the TNF superfamily. In one embodiment, the term LT-alpha, as used herein, refers to human LT-alpha. The UniProt accession number of human LT-alpha is P01374.

TL1A is a type II transmembrane protein belonging to the TNF superfamily and has been designated TNF superfamily member 15 (TNFSF15). In one embodiment, the term TL1A, as used herein, refers to human TL1A. The UniProt accession number of human TL1A is O95150-1.

Tumor necrosis factor alpha (TNF-alpha), also known as cachectin or TNFSF2, is a type II transmembrane protein belonging to the TNF superfamily. In one embodiment, the term TNF-alpha, as used herein, refers to human TNF-alpha. The UniProt accession number of human TNF-alpha is P01375.

TNF-related apoptosis-inducing ligand (TRAIL), also known as Apo-2 ligand or TNFSF10, is a type II transmembrane protein belonging to the TNF superfamily. In one embodiment, the term TRAIL, as used herein, refers to human TRAIL. The UniProt accession number of human TRAIL is P50591.

Receptor activator of NF-kB (RANK) ligand (RANKL), also referred to as TRANCE, ODF, OPGL or TNFSF11, is a type II transmembrane protein belonging to the TNF superfamily. In one embodiment, the term RANKL, as used herein, refers to human RANKL. The UniProt accession number of human RANKL is O14788.

TWEAK is a type II transmembrane protein belonging to the TNF superfamily and is also referred to as APO3 ligand or TNFSF12. In one embodiment, the term TWEAK, as used herein, refers to human TWEAK. The UniProt accession number of human TWEAK is O43508.

In one embodiment, the receptor of the first ligand and the receptor of the second ligand are located on the same cell ("cis"), wherein, preferably, the first ligand and the second ligand are selected from the group consisting of CD27L, 4-1BBL and OX40L. In one embodiment, said cell is a T cell, preferably a CD4[30] and/or CD8+ T cell. In one embodiment, said T cell is an activated T cell.

In another embodiment, the receptor of the first ligand and the receptor of the second ligand are located on different cells ("trans"). Said different cells may be of the same type or of different types. In one embodiment, said different cells are an antigen-presenting cell (APC), such as a dendritic cell, and a T cell. In another embodiment, said different cells are a B cell and a T cell. In one embodiment, the first ligand or the second ligand is CD40L and the respective other ligand is selected from the group consisting of CD27L, 4-1BBL and OX40L. In one embodiment, said T cell is a CD4+ and/or CD8+ T cell. In one embodiment, said T cell is an activated T cell.

In one embodiment, the cytokine fusion protein activates the receptor of the first ligand and/or the receptor of the second ligand. In one embodiment, the cytokine fusion protein is a cis-activating cytokine fusion protein, simultaneously activating the receptor of the first ligand and the receptor of the second ligand located on the same cell. In another embodiment, the cytokine fusion protein is a trans-activating cytokine fusion protein, simultaneously activating the receptor of the first ligand and the receptor of the second ligand located on different cells. In one embodiment, the cytokine fusion protein activates the NF-kappaB pathway in and/or induces IL-8 release from the cell(s) expressing the receptor(s) of the first ligand and/or second ligand.

In one embodiment, the cytokine fusion protein activates T cells and/or induces proliferation of T cells. In one embodiment, the cytokine fusion protein induces antigen-specific proliferation of T cells. In one embodiment, said T cells are CD4+ and/or CD8+ T cells. In one embodiment, said T cells are activated T cells.

The term "extracellular domain", as used herein, refers to the extracellular C-terminal part of a ligand of the TNF superfamily comprising the TNF homology domain (THD). The extracellular domain is characterized by its ability to form a (homo-)trimer capable of binding to a receptor of the ligand, and may also be referred to as "receptor-binding domain".

A "fragment or variant" of the extracellular domain which can be used in accordance with the present invention is a functional fragment or variant of the extracellular domain which has the ability to form a (homo-)trimer capable of binding to a receptor of the ligand. Thus, a suitable fragment or variant comprises at least a functional TNF homology domain (THD).

The terms "part" or "fragment" are used interchangeably herein and refer to a continuous element. For example, a part of a structure, such as an amino acid sequence or protein, refers to a continuous element of said structure. A part or fragment of a protein sequence preferably comprises a sequence of at least 6, in particular at least 8, at least 12, at least 15, at least 20, at least 30, at least 50, at least 100, at least 150 or at least 200 consecutive amino acids of the protein sequence.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to modifications being in positions in the amino acid sequence which are not conserved between homologous proteins or peptides and/or to replacing amino acids with other ones having similar properties. Preferably, amino acid substitutions in protein variants are conservative amino acid substitutions. A conservative amino acid substitution involves substitution of an amino acid with another one of the same family of amino acids, i.e., amino acids which are related in their side chains (e.g., in terms of the electrical charge and/or size). Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "fusion protein" generally refers to proteins created by joining two or more distinct (poly-)peptides or proteins, preferably head-to-tail (i.e., N-terminus to C-terminus or vice versa), resulting in a single protein with functional properties derived from each of the original proteins. According to the present invention, the term "cytokine fusion protein" also encompasses multimeric, e.g., dimeric or trimeric, complexes of distinct fusion proteins, which are referred to herein as "subunits". Preferably, the subunits non-covalently or covalently (e.g., via disulfide bonds) associate to form the cytokine fusion protein.

A preferred subunit in accordance with the present invention has the general formula

N'-A-L-B-C'     (Formula II)

as defined herein, wherein, preferably, three of these subunits non-covalently associate via the extracellular domains or fragments or variants thereof of the first ligand and the extracellular domains or fragments or variants thereof of the second ligand to form the cytokine fusion protein.

Another preferred subunit in accordance with the present invention has the general formula

N'-A-L$_A$-A-L$_A$-A-L-B-L$_B$-B-L$_B$-B-C'     (Formula I)

as defined herein, wherein L further comprises a multimerization domain, preferably a dimerization domain, allowing the formation of a multimeric, preferably dimeric, cytokine fusion protein.

The term "block", as used herein, refers to a molecular unit/entity comprising three covalently linked extracellular domains or fragments or variants thereof of a ligand of the TNF superfamily. In one embodiment, the block has the general formula A-L$_A$-A-L$_A$-A or B-L$_B$-B-L$_B$-B, wherein A, B, L$_A$ and L$_B$ are as defined herein. In one embodiment, the block comprises or consists of an amino acid sequence in accordance with one of SEQ ID NOs: 9 to 12.

The term "covalently linked", as used herein, refers to linkage via a covalent bond or via a covalent linker molecule, such as a peptide linker.

The term "peptide linker", as used herein, refers to a peptide adapted to connect/link protein moieties, e.g., extracellular domains of ligands of the TNF superfamily, or blocks thereof, or homotrimers formed by these extracellular domains. A peptide linker in accordance with the present invention may have any length, i.e., comprise any number of amino acid residues. However, it is preferably long enough to provide an adequate degree of flexibility to prevent the connected/linked moieties from interfering with each other's activity—e.g., the ability of the extracellular domains of a ligand of the TNF superfamily to form a homotrimer capable of binding to a receptor of the ligand, and/or the ability of two different homotrimers to bind to two different receptors on the same cell ("cis") or on different cells ("trans")—for example, by steric hindrance, and to allow for proper protein folding; yet it is preferably short enough to provide stability (e.g., proteolytic stability) in the cell.

In preferred embodiments, the peptide linkers have a length of 1 to 30 amino acids. Thus, according to the present invention, a peptide linker may be composed of a single amino acid residue. Preferably, a long peptide linker connects the extracellular domain(s) or fragment(s) or variant(s) thereof of the first ligand with the extracellular domain(s) or fragment(s) or variant(s) thereof of the second ligand, e.g., the first homotrimer with the second homotrimer or the first block with the second block, whereas, generally, a short peptide linker is used for connecting two extracellular domains or fragments or variants thereof of the first or second ligand, respectively, i.e. two extracellular domains or fragments or variants thereof of the same ligand. In the case of the ligand 4-1BBL, preferably a long peptide linker is used for connecting two of its extracellular domains or fragments or variants thereof. Short peptide linkers may consist of 12 or less such as 11, 10, 9, 8, 7, 6, 5, 4, 3, 2 or 1 amino acids, and, preferably, 1 to 7 amino acids. Long peptide linkers may consist of 12 or more, such as 12 to 30 or 12 to 25 or 12 to 20 amino acids.

The amino acids of the peptide linker may be selected from all naturally or non-naturally occurring amino acids, wherein the amino acids glycine (Gly, G), serine (Ser, S) and threonine (Thr, T) are preferred. In one embodiment, the peptide linker is a glycine-serine-threonine-rich linker or glycine-serine-rich linker, wherein at least 50%, preferably at least 60%, more preferably at least 70%, more preferably at least 80%, even more preferably at least 90% of the amino acids are a glycine or serine or threonine residue or a glycine or serine residue, respectively. In another embodiment, the amino acids are selected from glycine, serine and threonine, i.e., the peptide linker is exclusively composed of glycine, serine and threonine residues (referred to as a glycine-serine-threonine linker). In yet another embodiment, the peptide linker is exclusively composed of glycine and serine residues (referred to as a glycine-serine linker).

Preferred peptide linkers in accordance with the present invention have the general formula $(GGGGX)_n$, wherein X is, at each occurrence, independently selected from S and T, and n is an integer selected from 1 to 6, preferably 1 to 5; or a general formula selected from the group consisting of GXG, GGXGG and GGGXGGG, wherein X is S or T.

Preferred short peptide linkers have a general formula selected from the group consisting of GXG, GGXGG, GGGXGGG and GGGGXGGGG, wherein X is S or T, preferably S. A particularly preferred short peptide linker is GGGXGGG, wherein X is S or T, preferably S.

Preferred long peptide linkers have the general formula $(GGGGX)_n$, wherein X is, at each occurrence, independently selected from S an T, and n is an integer selected from 3 to 6, preferably 3 to 5, more preferably 3 and 4. Particularly preferred long peptide linkers are selected from the group consisting of $(GGGGS)_3$ (SEQ ID NO: 19), GGGGSGGGTGGGS (SEQ ID NO: 20) and $(GGGGS)_4$ (SEQ ID NO: 21).

Preferably, in case the cytokine fusion protein comprises a molecule/structure having the general formula of Formula I as defined herein, L comprises a long peptide linker as defined herein and/or $L_A$ and $L_B$ are, at each occurrence, independently selected from a covalent bond (e.g., a peptide bond), a short peptide linker as defined herein and a long peptide linker as defined herein.

Preferably, in case A or B comprises the extracellular domain or a fragment or variant thereof of 4-1BBL, $L_A$ or $L_B$ is, at each occurrence, independently selected from long peptide linkers as defined herein. Preferably, in case neither A nor B comprises the extracellular domain or a fragment or variant thereof of 4-1BBL, $L_A$ and $L_B$ are, at each occurrence, independently selected from a covalent bond (e.g., a peptide bond) and a short peptide linker as defined herein.

According to the present invention, $L_A$ and $L_B$ may be the same or different.

According to the present invention, in case the cytokine fusion protein comprises a molecule/structure having the general formula of Formula I as defined herein, L may further comprise a multimerization domain allowing the multimerization of the cytokine fusion protein.

In such cases, L may comprise a peptide linker as defined herein, in which the multimerization domain has been inserted. In an alternative embodiment, L may comprise two peptide linkers as defined herein sandwiching the multimerization domain, wherein the two peptide linkers may be the same or different. In one embodiment, the two peptide linkers are selected from short peptide linkers as defined herein. In yet another embodiment, the multimerization domain represents the peptide linker comprised by L.

Multimerization may occur by non-covalent interaction and/or covalent interaction, in particular via one or more disulfide bonds, between multiple (e.g., 2, 3 or 4, preferably 2 or 3, more preferably 2) multimerization domains.

Suitable multimerization domains are known to a person skilled in the art and include, for example, trimerization domains, such as a tenascin trimerization motif, a collectin trimerization domain and streptavidin, and dimerization domains, such as an IgE heavy-chain domain 2 (EHD2), an IgM heavy-chain domain 2 (MID2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MID4), an Fc domain, and an uteroglobin dimerization domain. In one embodiment, the dimerization domain is an EHD2 domain or an MHD2 domain, e.g., as described in WO 2013/156148 A1. In one embodiment, the dimerization domain is a human EHD2 domain, which, preferably, comprises or consists of the amino acid sequence of SEQ ID NO: 23. Also included are functional variants of any one of the foregoing domains, e.g., domains that have been modified so as to extend their half-life and/or increase their efficiency. Suitable modifications are known to a person skilled in the art and include, but are not limited to, modifications of the Fc domain which increase its affinity for FcRn, as described, for example, in Zalevsky, J. et al. (2010), Nature Biotechnology, 28(2):157-9 (e.g., N434S, V259I/V308F, M252Y/S254T/T256E, M428L/N434S, and V259I/V308F/M428L).

In case the cytokine fusion protein comprises a molecule/structure (or at least one, preferably three, subunits) having the general formula of Formula II as defined herein, L preferably comprises a long peptide linker as defined herein.

The peptide linkers as described herein may be replaced with non-peptidic molecules, e.g., non-peptidic oligomers and polymers of suitable lengths. Such equivalent embodiments are explicitly included in the present invention.

Preferably, in the cytokine fusion protein according to the present invention, the first ligand is CD40L, and the second ligand is CD27L;

the first ligand is CD27L, and the second ligand is CD40L;

the first ligand is CD40L, and the second ligand is 4-1BBL;

the first ligand is 4-1BBL, and the second ligand is CD40L;

the first ligand is CD27L, and the second ligand is 4-1BBL;

the first ligand is 4-1BBL, and the second ligand is CD27L;

the first ligand is CD40L, and the second ligand is OX40L;

the first ligand is OX40L, and the second ligand is CD40L;

the first ligand is CD27L, and the second ligand is OX40L;

the first ligand is OX40L, and the second ligand is CD27L;

the first ligand is OX40L, and the second ligand is 4-1BBL; or the first ligand is 4-1BBL, and the second ligand is OX40L.

In one embodiment, the cytokine fusion protein comprises a molecule/structure (or at least one, preferably three, subunits) having the general formula of Formula II as defined herein, wherein the second ligand, i.e., the C-terminal ligand, is CD40L.

A "label or tag allowing the detection and/or isolation of the cytokine fusion protein" is meant to include any labels/tags known in the art for these purposes. Particularly preferred are affinity tags, such as chitin binding protein (CBP), maltose binding protein (MBP), glutathione-S-transferase (GST) and poly(His) (e.g., His$_6$); solubilization tags, such as thioredoxin (TRX) and poly(NANP); chromatography tags, such as a FLAG-tag; epitope tags, such as V5-tag, myc-tag and HA-tag; and fluorescent or luminescent labels or tags, such as fluorescent proteins (e.g., GFP, YFP, RFP etc.), fluorescent dyes and luciferase. In one embodiment, the label/tag is a FLAG-tag.

The amino acid sequence of a (poly)peptide label or tag may be introduced at any position within the amino acid sequence of the cytokine fusion protein, and may, for example, take the shape of a loop within the encoded protein structure (e.g., within any of the peptide linkers described herein or even within the extracellular domains of the first and second ligand as long as the label/tag does not interfere with their function), or it may be N-terminally or C-terminally fused. The label or tag may further contain a cleavage site that allows a removal of the label or tag from the cytokine fusion protein. Similarly, non-peptidic labels or tags, e.g., fluorescent dyes, may be conjugated to the cytokine fusion protein at any suitable site.

Cytokine fusion proteins according to the invention may also comprise an amino acid sequence for facilitating secretion of the molecule, such as an N-terminal secretion signal. Preferably, the secretion signal is a signal sequence that allows a sufficient passage through the secretory pathway and/or secretion into the extracellular environment. Preferably, the secretion signal sequence is cleavable and is removed from the mature cytokine fusion protein. The secretion signal sequence is preferably chosen with respect to the cell or organism which the cytokine fusion protein is produced in. In one embodiment, the secretion signal sequence comprises or consists of the amino acid sequence of SEQ ID NO: 15 or SEQ ID NO: 22.

The cytokine fusion protein of the invention may further comprise a binding domain which serves, e.g., to enhance selectivity for a specific cell type. This can be achieved, e.g., by providing a binding domain that binds to a specific antigen expressed on the surface of said cell type.

The cytokine fusion protein according to the present invention may further comprise one or more modifications increasing the stability of the cytokine fusion protein. The term "stability" of the cytokine fusion protein relates to the "half-life" of the cytokine fusion protein, e.g., in vivo. "Half-life" relates to the period of time which is needed to eliminate half of the activity, amount, or number of molecules.

The cytokine fusion protein may, for example, be conjugated to a half-life extension module. Such modules are known to a person skilled in the art and include, for example, albumin, an albumin-binding domain, an immunoglobulin-binding domain, an FcRn-binding motif, and, in particular, a polymer. Particularly preferred polymers include polyethylene glycol (PEG), hydroxyethyl starch (HES), polysialic acid and PEG-mimetic peptide sequences.

The term "binding" according to the invention preferably relates to a specific binding. A binding agent, such as a cytokine fusion protein in accordance with the present invention, is specific for a predetermined target if it is capable of binding to said predetermined target while it is not capable of binding to other targets.

A "nucleic acid molecule" is according to the invention preferably deoxyribonucleic acid (DNA) or ribonucleic acid (RNA), more preferably RNA (e.g., mRNA), most preferably in vitro transcribed RNA (IVT RNA) or synthetic RNA. A nucleic acid molecule may according to the invention be in the form of a molecule which is single-stranded or double-stranded and linear or covalently closed to form a circle.

In the context of the present invention, the term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a 3-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally-occurring DNA.

In the context of the present invention, the term "RNA" relates to a molecule which comprises ribonucleotide residues and preferably is entirely or substantially composed of ribonucleotide residues. "Ribonucleotide" relates to a nucleotide with a hydroxyl group at the 2'-position of a 1-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA. According to the invention, "RNA" refers to single-stranded RNA or double stranded RNA.

According to the present invention, the term "messenger RNA (mRNA)" relates to a "transcript" which may be generated by using a DNA template and may encode a peptide or protein. Typically, an mRNA comprises a 5'-untranslated region, a protein coding region, and a 3'-untranslated region. In the context of the present invention, mRNA may be generated by in vitro transcription from a DNA template. The in vitro transcription methodology is known to the skilled person. For example, there is a variety of in vitro transcription kits commercially available.

According to the invention, the RNA may be modified. For example, RNA may be stabilized by one or more modifications having stabilizing effects on RNA.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or non-naturally occurring (synthetic) ribonucleotides in order to increase its stability and/or decrease cytotoxicity and/or modulate its immunostimulating potential. For example, in one embodiment, in the RNA used according to the invention uridine is substituted partially or completely, preferably completely, by pseudouridine.

In one embodiment, the term "modification" relates to providing a RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell. Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be generated post-transcriptionally using capping enzymes, for example, capping enzymes of vaccinia virus.

The RNA may comprise further modifications. For example, a modification of mRNA used in the present invention may be an extension or truncation of the naturally occurring poly(A) tail.

The term "stability" of RNA relates to the "half-life" of RNA. "Half-life" relates to the period of time which is needed to eliminate half of the activity, amount, or number of molecules. In the context of the present invention, the half-life of a RNA is indicative for the stability of said RNA.

If, according to the present invention, it is desired to decrease stability of RNA, it is also possible to modify RNA so as to interfere with the function of elements as described above increasing the stability of RNA.

According to the present invention, RNA may be obtained by chemical synthesis or by in vitro transcription of an appropriate DNA template. In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription. The cDNA may be obtained by reverse transcription of RNA. Preferably, cloning vectors are used for producing transcripts which generally are designated transcription vectors.

The term "translation" according to the invention relates to the process in the ribosomes of a cell by which a strand of messenger RNA directs the assembly of a sequence of amino acids to make a peptide or protein.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The term "expression control sequence", as used herein, is meant to refer to a nucleic acid sequence allowing the expression of the operatively linked nucleic acid molecule in a desired host cell or in an in vitro setting. Suitable expression control sequences are known to a person skilled in the art and include promoters, e.g. RNA promoters, such as a T7, T3 or SP6 promoter.

The nucleic acid molecule according to the present invention may be contained/comprised in a vector. The term "vector", as used herein, includes any vectors known to the skilled person, including plasmid vectors, cosmid vectors, phage vectors, such as lambda phage, viral vectors, such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably, said term relates according to the invention to any cell which can be transfected or transformed with an exogenous nucleic acid. Preferably, the cell when transfected or transformed with an exogenous nucleic acid and transferred to a recipient can express the nucleic acid in the recipient. The term "cell" includes prokaryotic cells, such as bacterial cells, and eukaryotic cells, such as yeast cells, fungal cells or mammalian cells. Suitable bacterial cells include cells from gram-negative bacterial strains, such as strains of *Escherichia coli*, *Proteus*, and *Pseudomonas*, and gram-positive bacterial strains, such as strains of *Bacillus*, *Streptomyces*, *Staphylococcus*, and *Lactococcus*. Suitable fungal cells include cells from the species of *Trichoderma*, *Neurospora*, and *Aspergillus*. Suitable yeast cells include cells from the species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanolica*), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells (APCs), such as dendritic cells, B cells and T cells, stem cells, such as hematopoietic stem cells and mesenchymal stem cells, and other cell types. An antigen-presenting cell is a cell that displays antigen in the context of major histocompatibility complex on its surface. T cells may recognize this complex using their T cell receptor (TCR).

The term "non-human organism", as used herein, is meant to include non-human primates or other animals, in particular mammals, such as cows, horses, pigs, sheep, goats, dogs, cats, rabbits, guinea pigs, hamsters or rodents, such as mice and rats.

The pharmaceutical compositions of the invention are preferably sterile and contain an effective amount of the cytokine fusion proteins, nucleic acid molecules or cells described herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may further comprise one or more carriers and/or excipients, all of which are preferably pharmaceutically acceptable. The term "pharmaceutically acceptable", as used herein, refers to the non-toxicity of a material which, preferably, does not interact with the action of the active agent of the pharmaceutical composition.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a subject.

Possible carrier substances for parenteral administration are, e.g., sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient", as used herein, is intended to include all substances which may be present in a pharmaceutical composition and which are not active ingredients, such as salts, binders, lubricants, thickeners, surface active agents, preservatives, emulsifiers, buffer substances, flavouring agents, or colorants.

Salts, which are not pharmaceutically acceptable, may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable preservatives for use in a pharmaceutical composition include benzalkonium chloride, chlorobutanol, paraben and thimerosal.

Suitable buffer substances for use in a pharmaceutical composition include acetic acid in a salt, citric acid in a salt, boric acid in a salt and phosphoric acid in a salt.

The agents and compositions described herein may be administered via any conventional route, such as by parenteral administration including by injection or infusion. Administration is preferably parenterally, e.g., intravenously, intraarterially, subcutaneously, intradermally or intramuscularly.

Pharmaceutical compositions suitable for parenteral administration usually comprise a sterile aqueous or non-aqueous preparation of the active compound, which is preferably isotonic to the blood of the recipient. Examples of compatible carriers/solvents/diluents are Ringer solution and isotonic sodium chloride solution. In addition, usually sterile, fixed oils are used as solution or suspension medium.

The agents and compositions described herein are administered in effective amounts. An "effective amount" refers to the amount, which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of an agent or composition described herein will depend on the condition to be treated, the severeness of the disease, the individual parameters of the subject, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a subject is insufficient with an initial dose, higher doses (or effectively higher doses achieved by a different, more localized route of administration) may be used.

As used herein, the term "kit of parts (in short: kit)" refers to an article of manufacture comprising one or more containers and, optionally, a data carrier. Said one or more containers may be filled with one or more of the above mentioned means or reagents. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the cytokine fusion protein, nucleic acid molecule, cell and/or pharmaceutical composition of the present invention.

The agents and compositions described herein can be administered to a subject, e.g., in vivo, to treat or prevent a variety of disorders, such as those described herein.

According to the invention, the term "disease" refers to any pathological state, in particular cancer, infectious diseases, inflammatory diseases, metabolic diseases, autoimmune disorders, degenerative diseases, apoptosis-associated diseases and transplant rejections.

As used herein, the term "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above.

The term "cancer" according to the invention also comprises cancer metastases. By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The term "infectious disease" refers to any disease which can be transmitted from individual to individual or from organism to organism, and is caused by a microbial agent (e.g. common cold). Examples of infectious diseases include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire's disease (*Legionella*), sexually transmitted diseases (e.g. chlamydia or gonorrhea), gastric ulcer (*Helicobacter*), cholera (*Vibrio*), tuberculosis, diphtheria, infections by *E. coli, Staphylococci, Salmonella* or *Streptococci* (tetanus); infections by protozoan pathogens such as malaria, sleeping sickness, leishmaniasis; toxoplasmosis, i.e. infections by Plasmodium, Trypanosoma, Leishmania and Toxoplasma; or fungal infections, which are caused, e.g., by *Cryptococcus neoformans, Histoplasma capsulatum, Coccidioides immitis, Blastomyces dermatitidis* or *Candida albicans*.

The term "inflammatory disease" refers to any disease, which is characterized by or associated with high levels of inflammation in tissues, in particular connective tissues, or degeneration of these tissues. A chronic inflammatory disease is a medical condition which is characterized by persistent inflammation. Examples of (chronic) inflammatory diseases include celiac disease, vasculitis, lupus, chronic obstructive pulmonary disease (COPD), irritable bowel disease, atherosclerosis, arthritis, ankylosing spondylitis, Crohn's disease, colitis, chronic active hepatitis, dermatitis and psoriasis.

The term "metabolic disease" refers to any disease or disorder that disrupts normal metabolism. Examples include cystinosis, diabetes, dyslipidemia, hyperthyroidism, hypothyroidism, hyperlipidemia, hypolipidemia, galactosemia, Gaucher's disease, obesity and phenylketonuria.

The term "autoimmune disorder" refers to any disease/disorder in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

The term "degenerative disease" refers to any disease in which the function or structure of the affected tissues or organs will increasingly deteriorate over time. Examples include Alzheimer's disease, Parkinson's disease, amyotrophic lateral sclerosis (ALS), Huntington's disease, macular degeneration, multiple sclerosis, muscular dystrophy, Niemann Pick disease, osteoporosis and rheumatoid arthritis.

The term "apoptosis-associated diseases" refers to any disease in which alterations of apoptosis are involved. Examples include cancer, neurological disorders, such as Alzheimer's disease, Parkinson's disease, Huntington's disease, amyotrophic lateral sclerosis (ALS) and stroke, heart diseases, such as ischemia reperfusion and chronic heart failure, infectious diseases and autoimmune diseases.

The term "transplant rejection" refers to the rejection of a transplanted tissue or organ by the recipient's immune system, which may, ultimately, destroy the transplanted tissue or organ.

The term "medicament", as used herein, refers to a substance/composition used in therapy, i.e., in the treatment of a disease.

By "treat" is meant to administer a compound or composition or a combination of compounds or compositions to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

The term "subject" means according to the invention a subject for treatment, in particular a diseased subject (also referred to as "patient"), including human beings, non-human primates or other animals, in particular mammals, such as cows, horses, pigs, sheep, goats, dogs, cats, rabbits, guinea pigs, hamsters or rodents, such as mice and rats. In a particularly preferred embodiment, the subject/patient is a human being.

EXAMPLES

Example 1: Cloning, Production and Purification of Duokines

DNA encoding the extracellular part of human CD40L (aa 116-261), human CD27L (aa 52-193), human 4-1BBL (aa 71-254) and human OX40L (aa 51-183) was codon-optimized for expression in human cells and synthesized by GENEART® (Life Technologies, Carlsbad, USA) adding appropriate cloning sites. Duokines were generated by fusing single subunits of two of these different cytokines via a 15 amino acid (in case of Duokines lacking 4-1BBL) or 20 amino acid (in case of Duokines containing 4-1BBL) glycine-serine rich linker and cloning into the expression plasmid pIRESpuro3 (Clontech, Mountain View, USA). N-terminally, the Duokines were provided with a VH leader sequence for secretion and a FLAG tag for purification and detection. The following Duokines were produced: CD40L-CD27L, CD27L-CD40L, CD40L-4-1BBL, 4-1BBL-CD40L, CD27L-4-1BBL, 4-1BBL-CD27L, CD40L-OX40L, OX40L-CD40L, CD27L-OX40L, OX40L-CD27L, 4-1BBL-OX40L and OX40L-4-1BBL (Tab. 1). All Duokines were produced from stably transfected HEK293 cells and purified from the cell culture supernatant by one-step FLAG affinity chromatography (Sigma-Aldrich, St. Louis, USA) resulting in yields of 0.3 to 1.9 mg/L supernatant.

Figure 2:
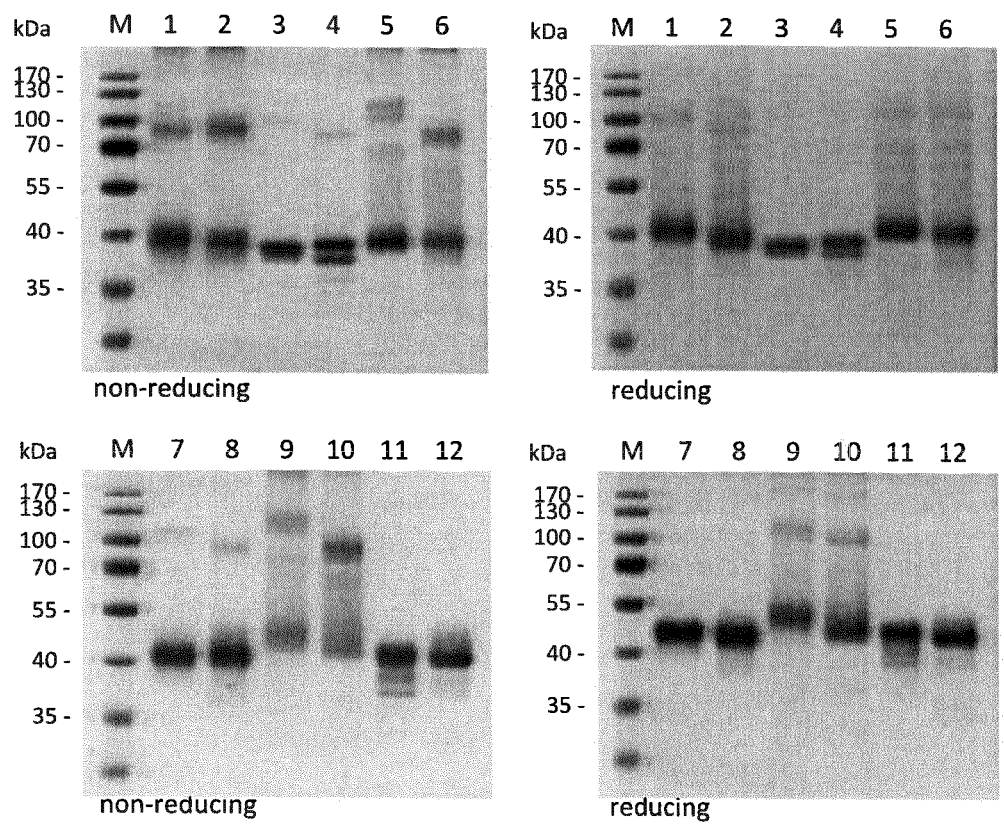
FIG. 2. SDS-PAGE analysis of the purified Duokines under reducing and non-reducing conditions using a 12% polyacrylamide gel (1, CD40L-CD27L; 2, CD27L-CD40L; 3, CD40L-4-1BBL; 4, 4-1BBL-CD40L; 5, CD27L-4-1BBL; 6, 4-1BBL-CD27L; 7, CD40L-OX40L; 8, OX40L-CD40L; 9, CD27L-OX40L; 10, OX40L-CD27L; 11, 4-1BBL-OX40L; 12, OX40L-4-1BBL). Proteins were visualized by staining with Coomassie Brilliant Blue G250.
Figure 3A:
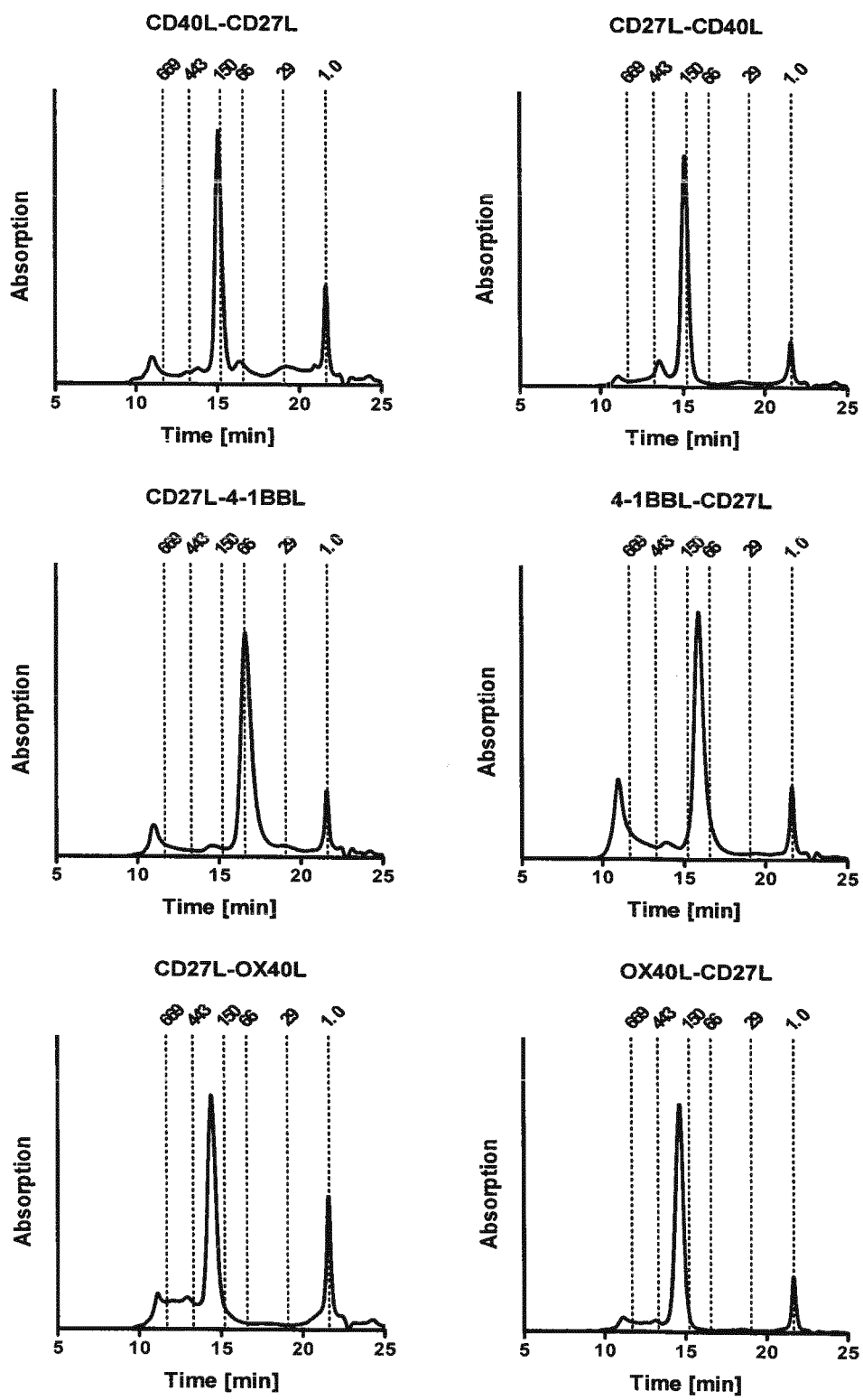
FIGS. 3 A and B. Size exclusion chromatography (SEC) analysis of the Duokines demonstrating the integrity of the fusion proteins. High-performance liquid chromatography (HPLC) was performed with a Yarra SEC-2000 (Phenomenex) at a flow rate of 0.5 mL/min. Thyroglobulin, alcohol dehydrogenase, bovine serum albumin, carbonic anhydrase and FLAG peptide were used as standard proteins.
Figure 3B:
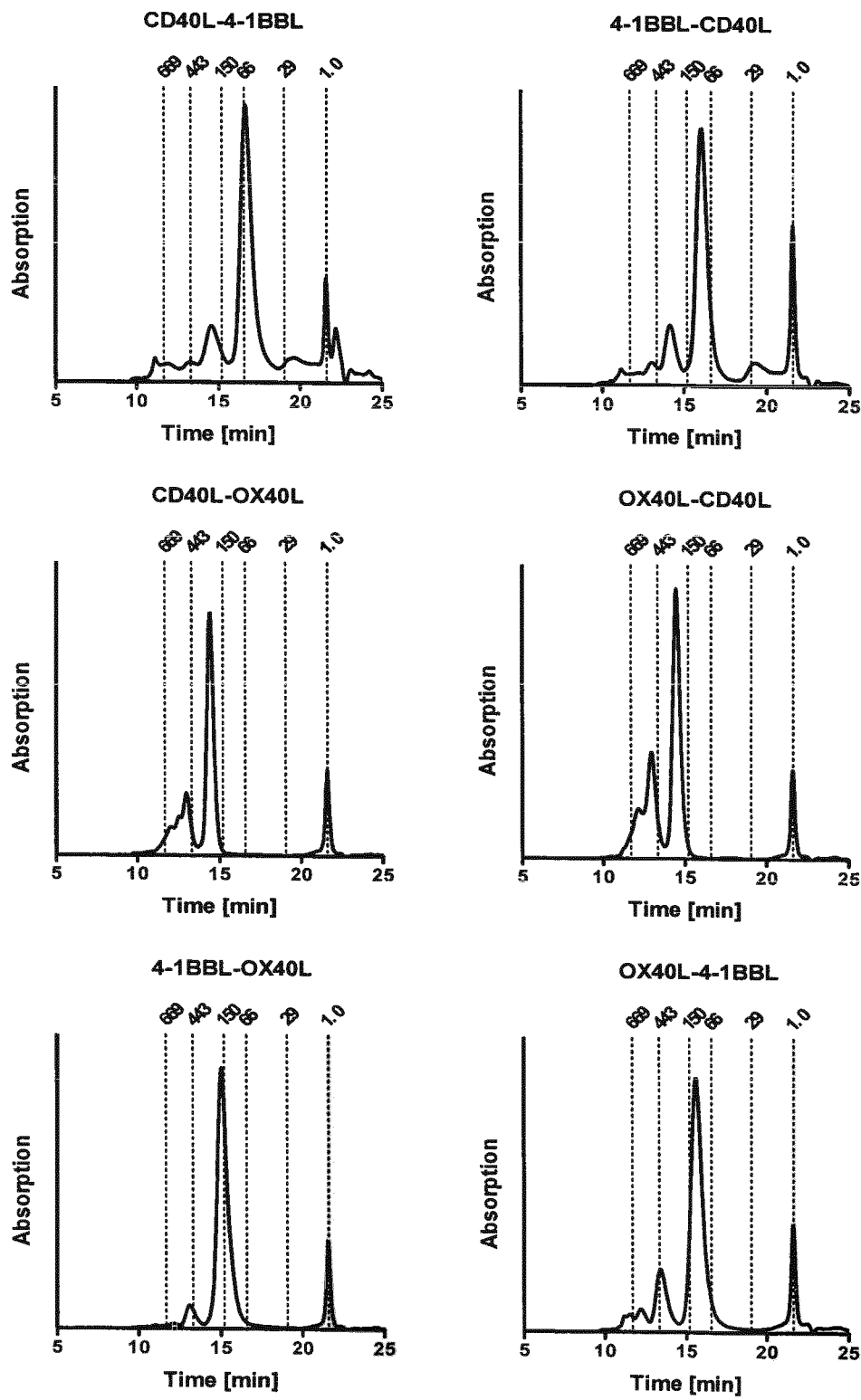

Duokines were analyzed in SDS-PAGE under reducing and non-reducing conditions using a 12% polyacrylamide gel and visualized by staining with Coomassie Brilliant Blue G250. SDS-PAGE analysis revealed the expected molecular masses of the monomeric polypeptide chains (approximately 33 kDa for Duokines lacking 4-1BBL and 37 kDa for Duokines containing 4-1BBL) taking into account the presence of potential N-glycosylation sites in CD40L (1 site; aa 240), CD27L (2 sites; aa 63 and 170) and OX40L (4 sites; aa 90, 114, 152, and 157) (FIG. 2, Tab. 1). Additionally, under non-reducing conditions all proteins showed a second minor band corresponding to the molecular masses of a dimer. Size exclusion chromatography using high performance liquid chromatography on a Yarra SEC-2000 (Phenomenex) with a flow rate of 0.5 mL/min confirmed the homotrimeric assembly of the Duokines. The Duokines CD40L-4-1BBL, 4-1BBL-CD40L, CD27L-4-1BBL and 4-1BBL-CD27L eluted as a major peak with an apparent molecular mass in the range between 80 and 100 kDa, therefore being somewhat smaller than the calculated molecular mass of 112 kDa, presumably due to a more compact structure of Duokines containing 4-1BBL. All other Duokines eluted as major peak with an apparent molecular mass between 130 and 160 kDa, which correlated to a 30-50% larger molecular mass than calculated, presumably due to N-glycosylation. Additionally, the Duokines 4-1BBL-CD27L, 4-1BBL-CD40L, CD40L-OX40L, OX40L-CD40L and OX40L-4-1BBL showed minor peaks corresponding most likely to higher molecular weight complexes (FIG. 3 AB).

TABLE 1

Duokines and their biochemical properties

| Duokine | N-terminal Cytokine | C-Terminal Cytokine | Linker | # N-glyc. sites per polypeptide chain | Binding ELISA ($EC_{50}$, nM) | Receptor activation ($EC_{50}$, nM) |
|---|---|---|---|---|---|---|
| CD40L-CD27L | CD40L | CD27L | (GGGGS)$_3$ (SEQ ID NO: 19) | 3 | 8.06 (CD40-Fc) 3.15 (CD27-Fc) | 2.36 (CD40) |
| CD27L-CD40L | CD27L | CD40L | (GGGGS)$_3$ (SEQ ID NO: 19) | 3 | 3.31 (CD40-Fc) 5.90 (CD27-Fc) | 2.99 (CD40) |
| CD40L-4-1BBL | CD40L | 4-1BBL | (GGGGS)$_4$ (SEQ ID NO: 21) | 1 | 10.13 (CD40-Fc) 2.11 (4-16B-Fc) | 3.01 (CD40) 0.45 (4-1BB) |
| 4-1BBL-CD40L | 4-1BBL | CD40L | (GGGGS)$_4$ (SEQ ID NO: 21) | 1 | 1.61 (CD40-Fc) 1.78 (4-1BB-Fc) | 2.95 (CD40) 0.18 (4-1BB) |
| CD27L-4-1BBL | CD27L | 4-1BBL | (GGGGS)$_4$ (SEQ ID NO: 21) | 2 | 6.34 (CD27-Fc) 1.41 (4-1BB-Fc) | 1.44 (4-16B) |
| 4-1BBL-CD27L | 4-1BBL | CD27L | (GGGGS)$_4$ (SEQ ID NO: 21) | 2 | 1.41 (4-1BB-Fc) 1.48 (CD27-Fc) | 1.22 (4-1BB) |
| CD40L-OX40L | CD40L | OX40L | (GGGGS)$_3$ (SEQ ID NO: 19) | 5 | 2.18 (CD40-Fc) 0.51 (OX40-Fc) | 16.6 (CD40) 0.70 (OX40) |
| OX40L-CD40L | OX40L | CD40L | (GGGGS)$_3$ (SEQ ID NO: 19) | 5 | 1.45 (CD40-Fc) 1.01 (OX40-Fc) | 3.86 (CD40) 0.73 (OX40) |
| CD27L-OX40L | CD27L | OX40L | (GGGGS)$_3$ (SEQ ID NO: 19) | 6 | 6.74 (CD27-Fc) 3.16 (OX40-Fc) | 10.2 (OX40) |
| OX40L-CD27L | OX40L | CD27L | (GGGGS)$_3$ (SEQ ID NO: 19) | 6 | 1.70 (CD27-Fc) n.d. (OX40-Fc) | 6.58 (OX40) |

TABLE 1-continued

Duokines and their biochemical properties

| Duokine | N-terminal Cytokine | C-Terminal Cytokine | Linker | # N-glyc. sites per polypeptide chain | Binding ELISA ($EC_{50}$, nM) | Receptor activation ($EC_{50}$, nM) |
|---|---|---|---|---|---|---|
| 4-1BBL-OX40L | 4-1BBL | OX40L | (GGGGS)$_4$ (SEQ ID NO: 21) | 4 | 1.13 (4-1BB-Fc) 0.45 (OX40-Fc) | 1.16 (4-1BB) 1.35 (OX40) |
| OX40L-4-1BBL | OX40L | 4-1BBL | (GGGGS)$_4$ (SEQ ID NO: 21) | 4 | 1.26 (4-1BB-Fc) 7.17 (OX40-Fc) | 2.75 (4-1BB) 0.85 (OX40) |

Example 2: Receptor Binding Properties of Duokines

Figure 4:
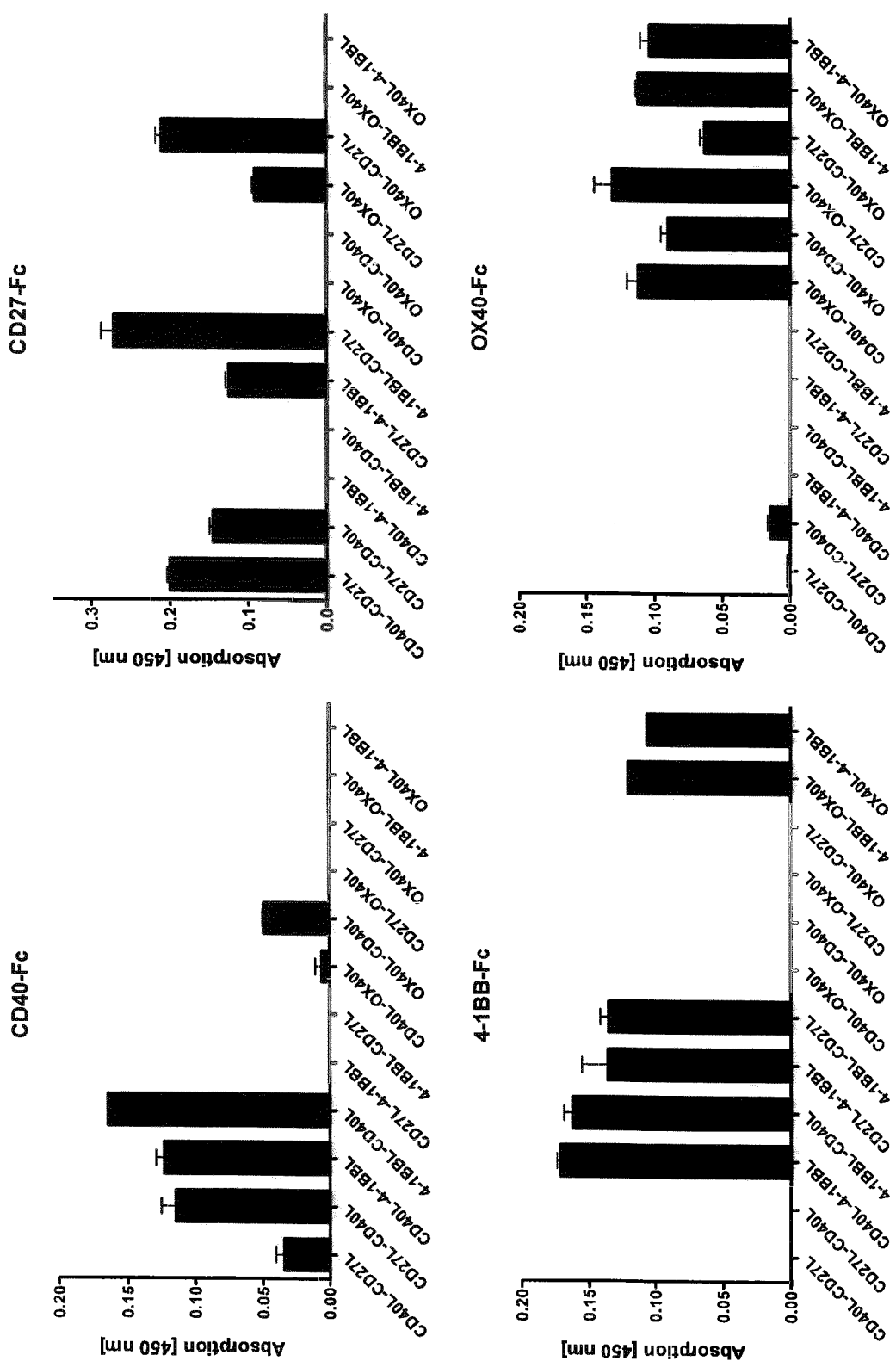
FIG. 4. Binding of Duokines (100 nM) to immobilized CD40-, CD27-, 4-1BB- and OX40-Fc fusion proteins in ELISA. All Duokines bound to the respective receptor-Fc fusion proteins, and no cross-reactivity was detected.
Figure 5A:
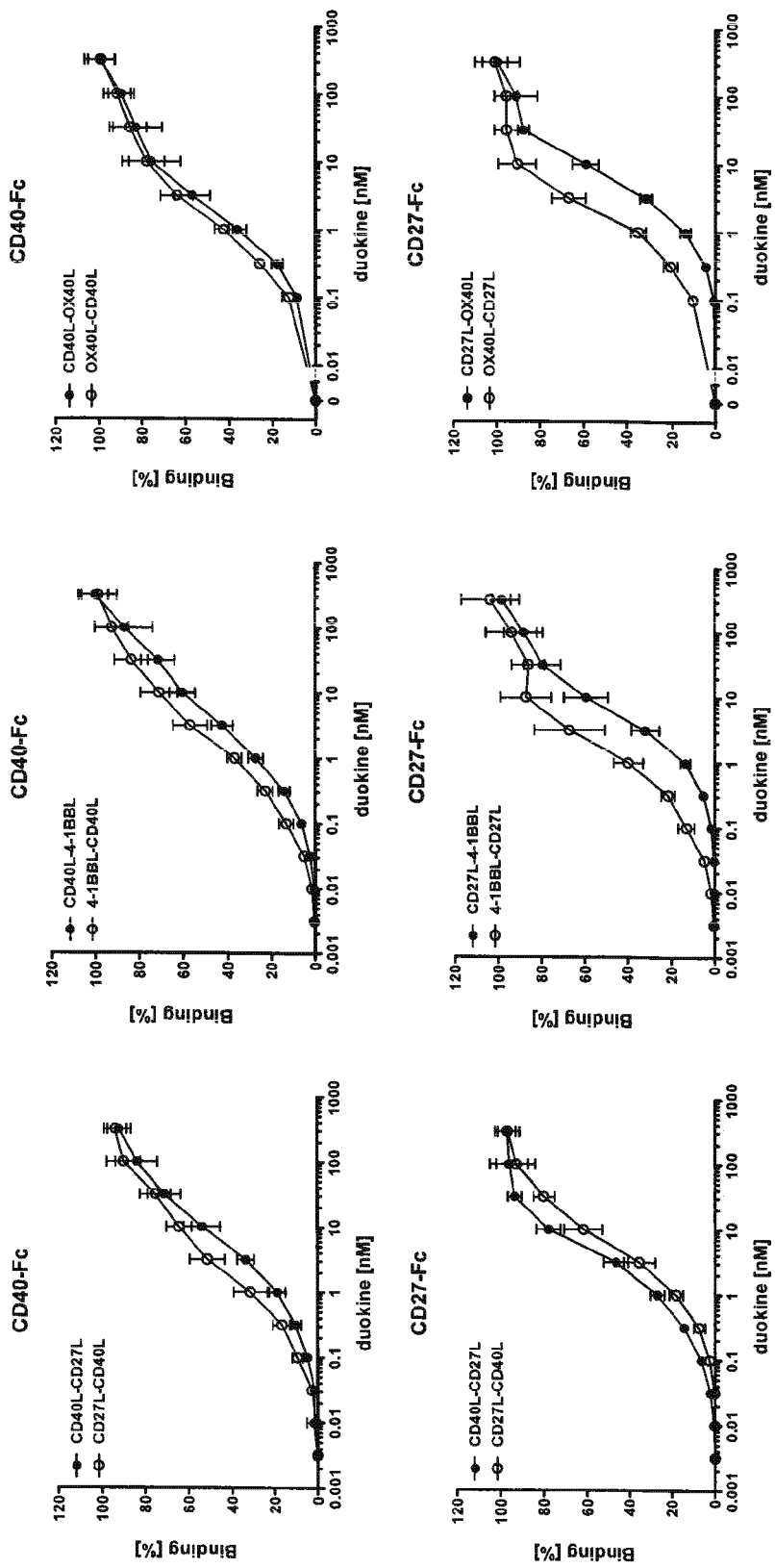
FIGS. 5 A and B. Binding of Duokines to immobilized CD40-, CD27-, 4-1BB- and OX40-Fc fusion proteins in ELISA (n=3±SD). Duokines were titrated in duplicates starting at a concentration of 316 nM. All Duokines bound to the respective receptor-Fc fusion proteins in a dose-dependent manner with $EC_{50}$ values in the low nanomolar range. Protein concentrations according to trimeric molecules.
Figure 5B:
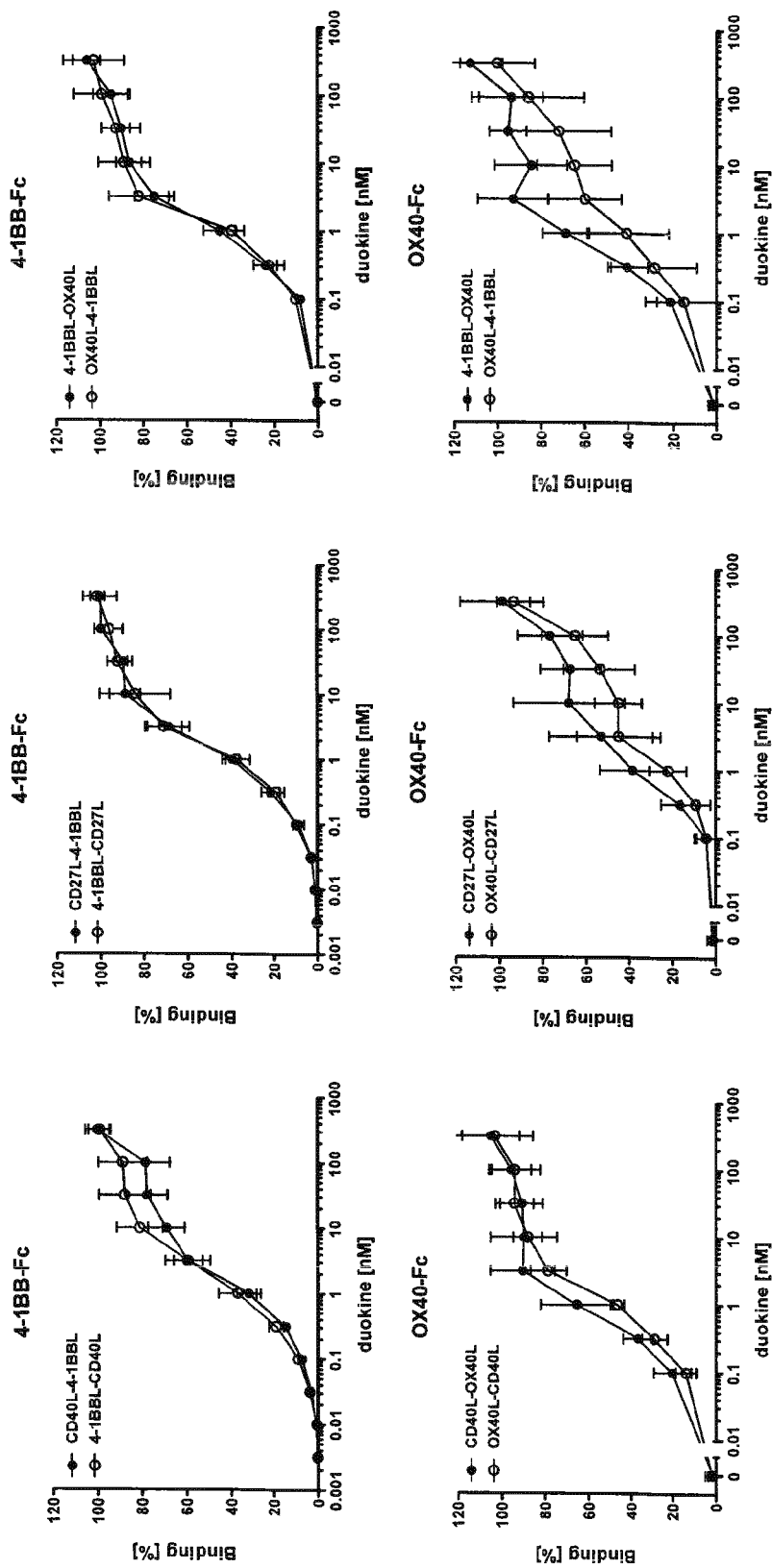

Receptor binding of the Duokines was analyzed by ELISA using fusion proteins of the extracellular region of CD40, CD27, 4-1BB and OX40, respectively, with the human Fcγ1 region including the hinge region for covalent assembly (CD40-Fc, CD27-Fc, 4-1BB-Fc, OX40-Fc). Receptor-Fc fusion proteins (200 ng/well) were coated overnight at 4° C. and remaining binding sites were blocked with PBS, 2% skimmed milk powder (2% MPBS). Duokines were titrated in duplicates starting at a concentration of 316 nM and bound Duokines were detected with HRP-conjugated mouse anti-FLAG antibody. All Duokines showed specific binding to their respective receptors and no cross-reactivity with other receptor-Fc fusion proteins was observed (FIG. 4). Duokine-receptor interactions were dose-dependent with $EC_{50}$ values in the low nanomolar ranges (FIG. 5 AB, Tab. 1).

Furthermore, the Duokines were analyzed by flow cytometry for binding to the fibrosarcoma cell line HT1080 engineered to express the CD40, CD27, 4-1BB or OX40 receptor, respectively (HT1080-CD40, HT1080-CD27, HT1080-4-1BB, HT1080-OX40). Here, 1.5×10$^5$ cells were incubated with 100 nM Duokines and binding was detected using a PE-labeled mouse anti-FLAG antibody. Cells were analyzed using a MACSQuant® 10 analyzer (Miltenyi Biotec, Bergisch Gladbach, Germany) and data was analyzed using FLOWJO® (Tree Star, Ashland, USA). Flow cytometry revealed that all Duokines bound the cell lines expressing their respective receptors (FIG. 6 AB).

Example 3: Bispecific Receptor Binding Properties of Duokines

Bispecificity of the Duokines was assessed by flow cytometry. 1.5×10$^5$ HT1080 cells expressing either the CD40, CD27, 4-1BB or OX40 receptor (HT1080-CD40, HT1080-CD27, HT1080-4-1BB, HT1080-OX40) were incubated with 100 nM Duokines followed by incubation with the corresponding receptor-Fc fusion protein (10 nM) to detect the second binding site. The cell-bound Duokine-receptor-complexes were detected using a PE-labeled mouse anti-human Fc antibody, thus only Duokines recognizing both receptors, one on the cell and the other provided as soluble Fc fusion protein, are able to produce a fluorescent signal. Cells were analyzed using a MACSQuant® 10 analyzer (Miltenyi Biotec) and data was analyzed using FLOWJO® (Tree Star, Ashland, USA). Here, it was shown that all Duokines were able to bind both receptors simultaneously, establishing dual binding capacity of the Duokines (FIG. 7 AB).

Example 4: Cloning, Production and Purification of Single-Chain Duokines (scDuokines)

DNA encoding single-chain derivatives of the extracellular part of human CD40L (aa 116-261), human CD27L (aa 52-193), human 4-1BBL (aa 71-254) and human OX40L (aa 51-183) was codon-optimized for expression in human cells and synthesized by Geneart (Life Technologies) adding appropriate cloning sites. In case of scCD40L, scCD27L and scOX40L the three single subunits of the cytokines were connected via a GGGSGGG (SEQ ID No: 24) linker, while a (GGGGS)$_3$ (SEQ ID No: 19) linker was used for sc4-1BBL. Single-chain Duokines (scDuokines) were generated by fusing two of these different single-chain cytokines via a 15 amino acid glycine-serine rich linker and cloning into the expression plasmid pIRESpuro3 (Clontech). N-terminally, the scDuokines were provided with a VH leader sequence for secretion and a FLAG tag for purification and detection. The following scDuokines were produced: scCD40L-scCD27L, scCD27L-scCD40L, scCD40L-sc4-1BBL, sc4-1BBL-scCD40L, scCD27L-sc4-1BBL, sc4-1BBL-scCD27L, scCD40L-scOX40L, scOX40L-scCD40L, scCD27L-scOX40L, scOX40L-scCD27L, sc4-1BBL-scOX40L and scOX40L-sc4-1BBL (Tab. 2). All scDuokines were produced from stably transfected HEK293 cells and purified from the cell culture supernatant by one-step FLAG affinity chromatography (Sigma-Aldrich) resulting in yields of 1.4 to 4.0 mg/L supernatant.

Figure 8:
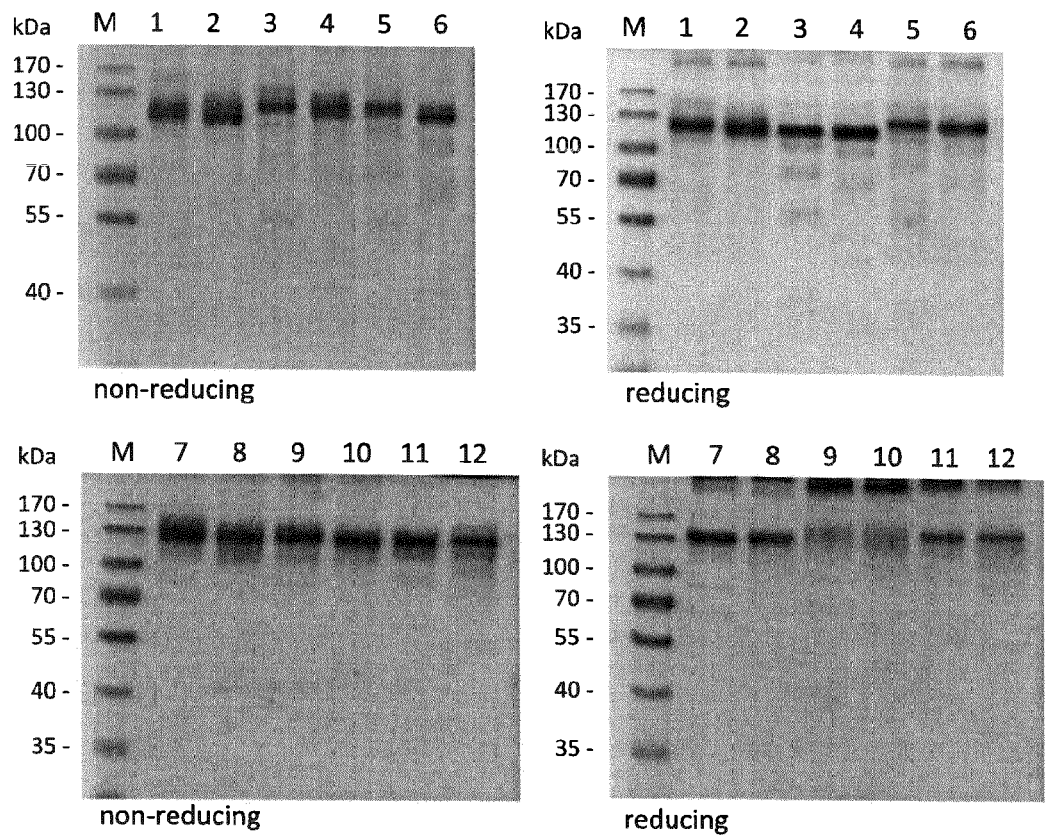
FIG. 8. SDS-PAGE analysis of the purified single-chain Duokines under reducing and non-reducing conditions using a 10% polyacrylamide gel (1, scCD40L-scCD27L; 2, scCD27L-scCD40L; 3, scCD40L-sc4-1BBL; 4, sc4-1BBL-scCD40L; 5, scCD27L-sc4-1BBL; 6, sc4-1BBL-scCD27L; 7, scCD40L-scOX40L; 8, scOX40L-scCD40L; 9, scCD27L-scOX40L; 10, scOX40L-scCD27L; 11, sc4-1BBL-scOX40L; 12, scOX40L-sc4-1BBL). Proteins were visualized by staining with Coomassie Brilliant Blue G250.

Single-chain Duokines were analyzed in SDS-PAGE under reducing and non-reducing conditions using a 10% polyacrylamide gel and visualized by staining with Coomassie Brilliant Blue G250. SDS-PAGE analysis under reducing and non-reducing conditions revealed the expected molecular masses of the trimeric polypeptide chains (approximately 97 kDa for Duokines lacking 4-1BBL and 111 kDa for Duokines containing 4-1BBL) taking into account the presence of potential N-glycosylation sites in CD40L (1 site; aa 240), CD27L (2 sites; aa 63 and 170) and OX40L (4 sites; aa 90, 114, 152 and 157) (FIG. 8, Tab. 2). Additionally, under reducing conditions all proteins showed a second band corresponding to higher molecular weight complexes. The appearance of higher molecular weight complexes was especially pronounced for scDuokines containing scOX40L. Size exclusion chromatography using high performance liquid chromatography on a Yarra SEC-2000 (Phenomenex) with a flow rate of 0.5 mL/min confirmed the preferential homotrimeric assembly of the scDuokines. ScCD40L-scCD27L and scCD27L-scCD40L eluted as a major peak with an apparent molecular mass of 125 kDa, therefore being slightly larger than the calculated molecular mass of 98 kDa. All scDuokines containing scOX40L showed a major peak corresponding to 140 and 160 kDa, with the longer retention time presumably due to the structure of scOX40L. The scDuokines composed of scCD40L, sc4-

Figure 9A:
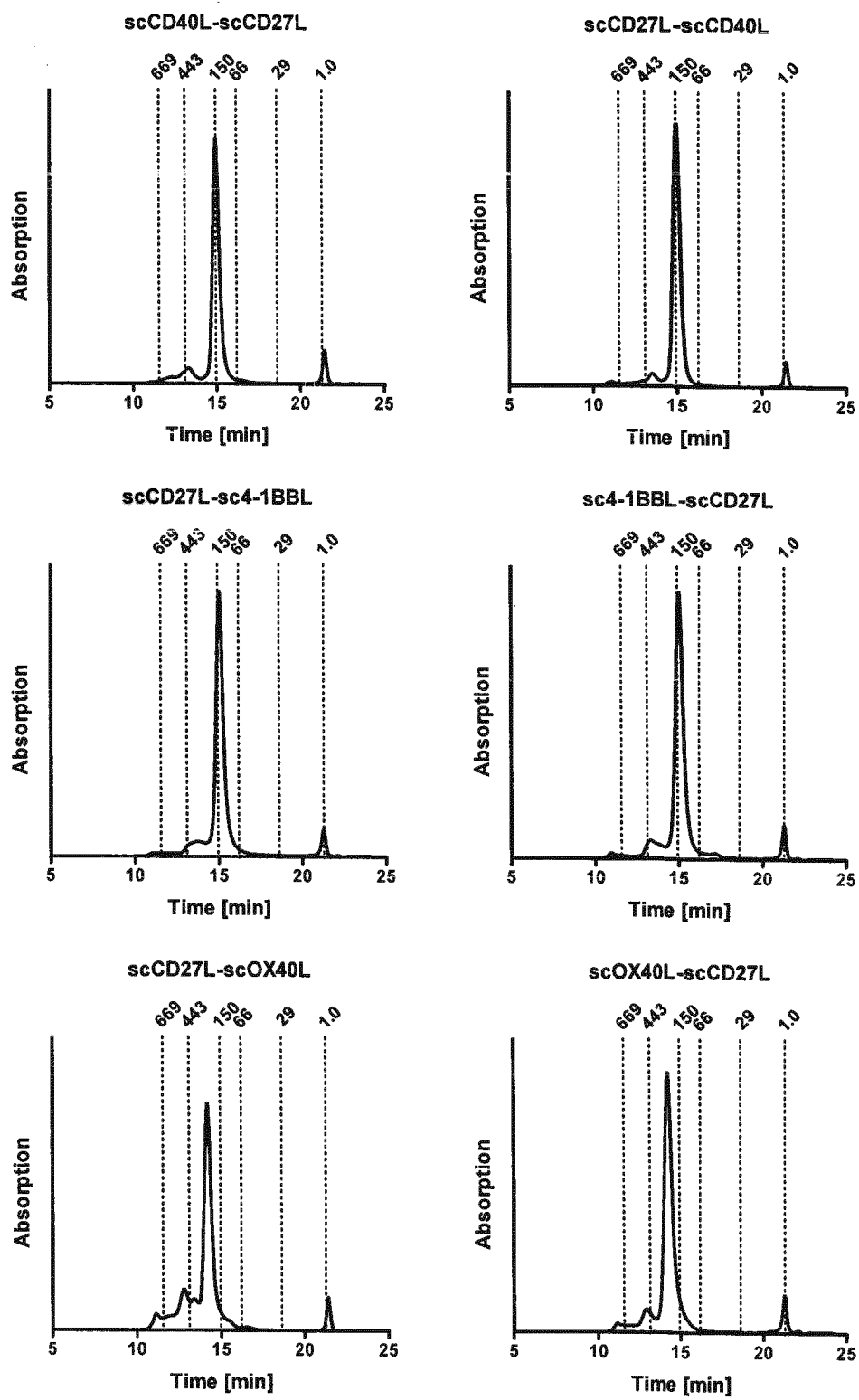
FIGS. 9 A and B. Size exclusion chromatography (SEC) analysis of the single-chain Duokines demonstrating the integrity of the fusion proteins. High-performance liquid chromatography (HPLC) was performed with a Yarra SEC-2000 (Phenomenex) at a flow rate of 0.5 mL/min. Thyroglobulin, alcohol dehydrogenase, bovine serum albumin, carbonic anhydrase and FLAG peptide were used as standard proteins.
Figure 9B:
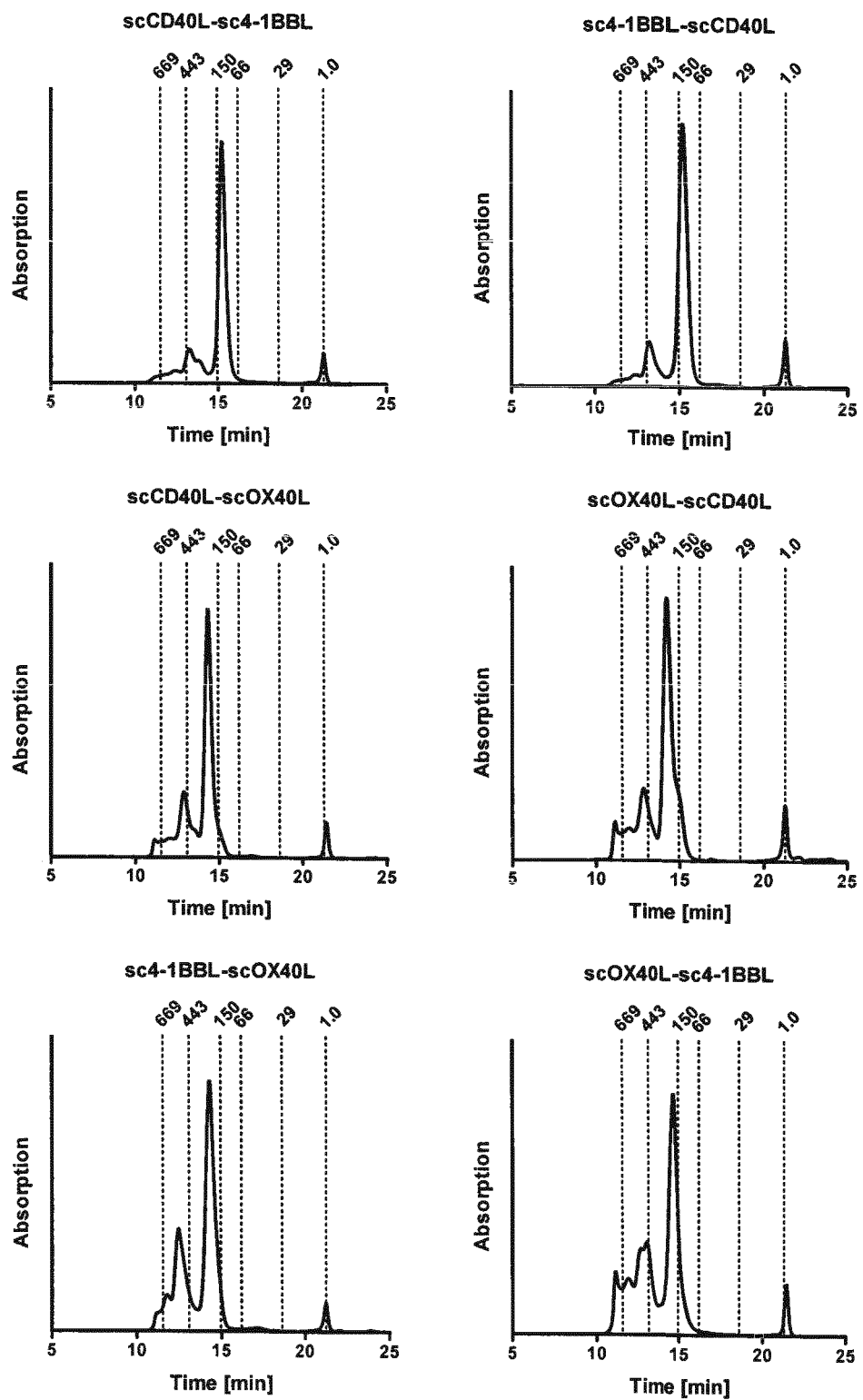

1BBL and scCD27L eluted as major peak corresponding to the calculated molecular mass of 110 kDa. Additionally, the scDuokines scCD40L-sc4-1BBL, sc4-1BBL-scCD40L, scCD40L-scOX40L, scOX40L-scCD40L, sc4-1BBL-scOX40L and scOX40L-sc4-1BBL showed minor peaks corresponding most likely to higher molecular weight complexes (FIG. 9 AB).

HT1080 engineered to express the CD40, CD27, 4-1BB or OX40 receptor, respectively (HT1080-CD40, HT1080-CD27, HT1080-4-1BB, HT1080-OX40). Here, $1.5 \times 10^5$ cells were incubated with 100 nM scDuokines and binding was detected using a PE-labeled mouse anti-FLAG antibody. Cells were analyzed using a MACSQuant® 10 analyzer (Miltenyi Biotec, Bergisch Gladbach, Germany) and

TABLE 2

Single-chain Duokines and their biochemical properties

| single-chain Duokine | N-terminal Cytokine | C-Terminal Cytokine | Linker | # N-glyc. sites per polypeptide chain | Binding ELISA ($EC_{50}$, nM) | Receptor activation ($EC_{50}$, nM) |
|---|---|---|---|---|---|---|
| scCD40L-scCD27L | scCD40L | scCD27L | GGGGSGGGGTGGGGS (SEQ ID NO: 20) | 9 | 4.26 (CD40-Fc)<br>3.42 (CD27-Fc) | 3.10 (CD40) |
| scCD27L-scCD40L | scCD27L | scCD40L | GGGGSGGGGTGGGGS (SEQ ID NO: 20) | 9 | 8.04 (CD40-Fc)<br>3.30 (CD27-Fc) | 3.70 (CD40) |
| scCD40L-sc4-1BBL | scCD40L | sc4-1BBL | GGGGSGGGGTGGGGS (SEQ ID NO: 20) | 3 | 7.02 (CD40-Fc)<br>3.17 (4-1BB-Fc) | 5.23 (CD40)<br>0.26 (4-1BB) |
| sc4-1BBL-scCD40L | sc4-1BBL | scCD40L | GGGGSGGGGTGGGGS (SEQ ID NO: 20) | 3 | 5.73 (CD40-Fc)<br>2.28 (4-1BB-Fc) | 2.85 (CD40)<br>0.18 (4-1BB) |
| scCD27L-sc4-1BBL | scCD27L | sc4-1BBL | GGGGSGGGGTGGGGS (SEQ ID NO: 20) | 6 | 9.23 (CD27-Fc)<br>4.57 (4-1BB-Fc) | 1.50 (4-1BB) |
| sc4-1BBL-scCD27L | sc4-1BBL | scCD27L | GGGGSGGGGTGGGGS (SEQ ID NO: 20) | 6 | 2.75 (CD27-Fc)<br>2.90 (4-1BB-Fc) | 1.37 (4-1BB) |
| scCD40L-scOX40L | scCD40L | scOX40L | GGGGSGGGGTGGGGS (SEQ ID NO: 20) | 15 | 40.2 (CD40-Fc)<br>1.33 (OX40-Fc) | 9.54 (CD40)<br>0.57 (OX40) |
| scOX40L-scCD40L | scOX40L | scCD40L | GGGGSGGGGTGGGGS (SEQ ID NO: 20) | 15 | 6.74 (CD40-Fc)<br>2.13 (OX40-Fc) | 3.22 (C040)<br>0.51 (OX40) |
| scCD27L-scOX40L | scCD27L | scOX40L | GGGGSGGGGTGGGGS (SEQ ID NO: 20) | 18 | 7.34 (CD27-Fc)<br>286 (OX40-Fc) | 1.49 (OX40) |
| scOX40L-scCD27L | scOX40L | scCD27L | GGGGSGGGGTGGGGS (SEQ ID NO: 20) | 18 | 4.62 (CD27-Fc)<br>n.d. (OX40-Fc) | 1.27 (OX40) |
| sc4-1BBL-scOX40L | sc4-1BBL | scOX40L | GGGGSGGGGTGGGGS (SEQ ID NO: 20) | 12 | 2.91 (4-1BB-Fc)<br>5.23 (OX40-Fc) | 13.22 (4-1BB)<br>0.45 (OX40) |
| scOX40L-sc4-1BBL | scOX40L | sc4-1BBL | GGGGSGGGGTGGGGS (SEQ ID NO: 20) | 12 | 4.61 (4-1BB-Fc)<br>347 (OX40-Fc) | 2.83 (4-1BB)<br>0.56 (OX40) |

Example 5: Receptor Binding Properties of Single-Chain Duokines

Figure 10:
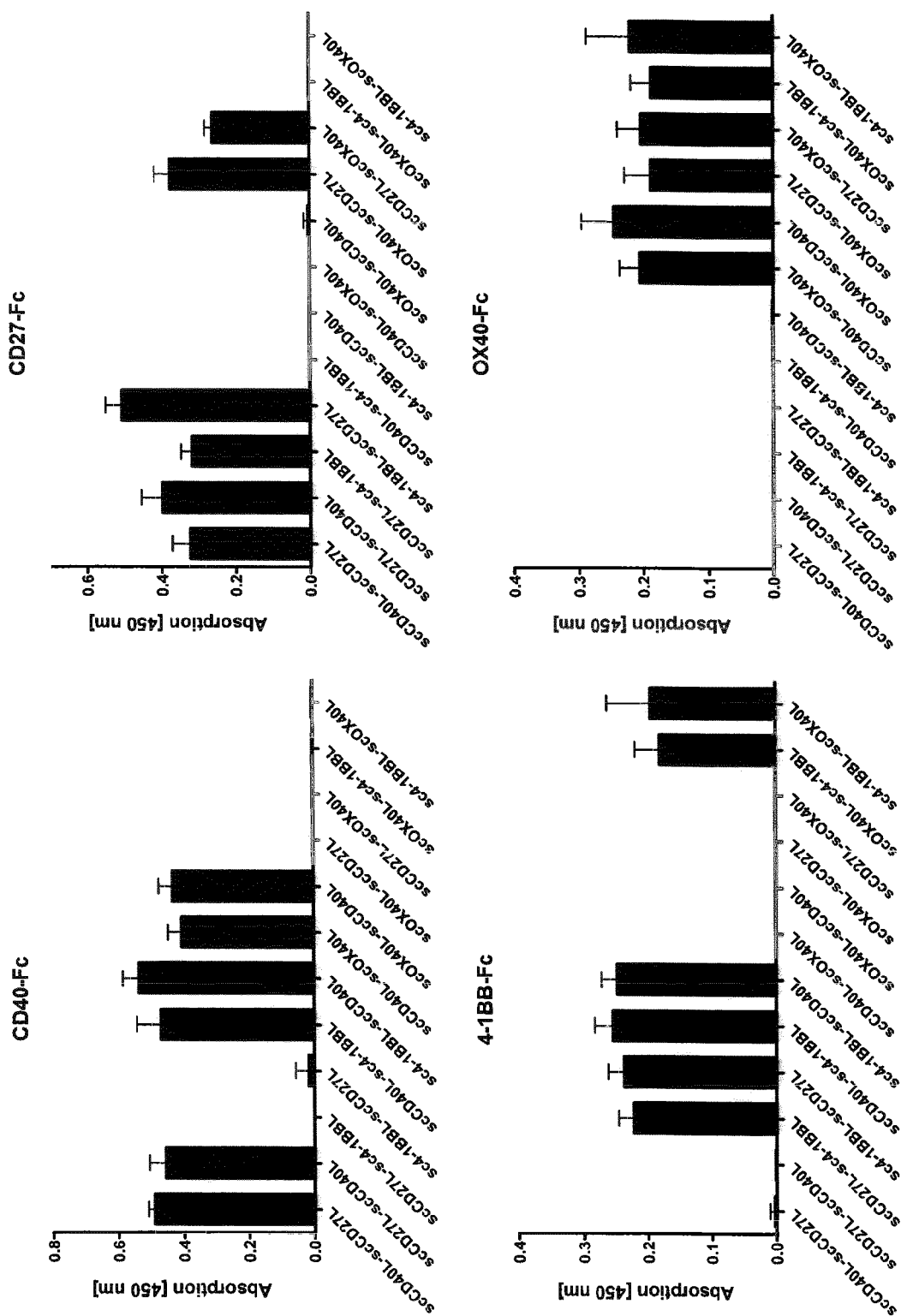
FIG. 10. Binding of single-chain Duokines (100 nM) to immobilized CD40-, CD27-, 4-1BB- and OX40-Fc fusion proteins in ELISA (n=3±SD). All single-chain Duokines bound to the respective receptor-Fc fusion proteins, and no cross-reactivity was detected.
Figure 11A:
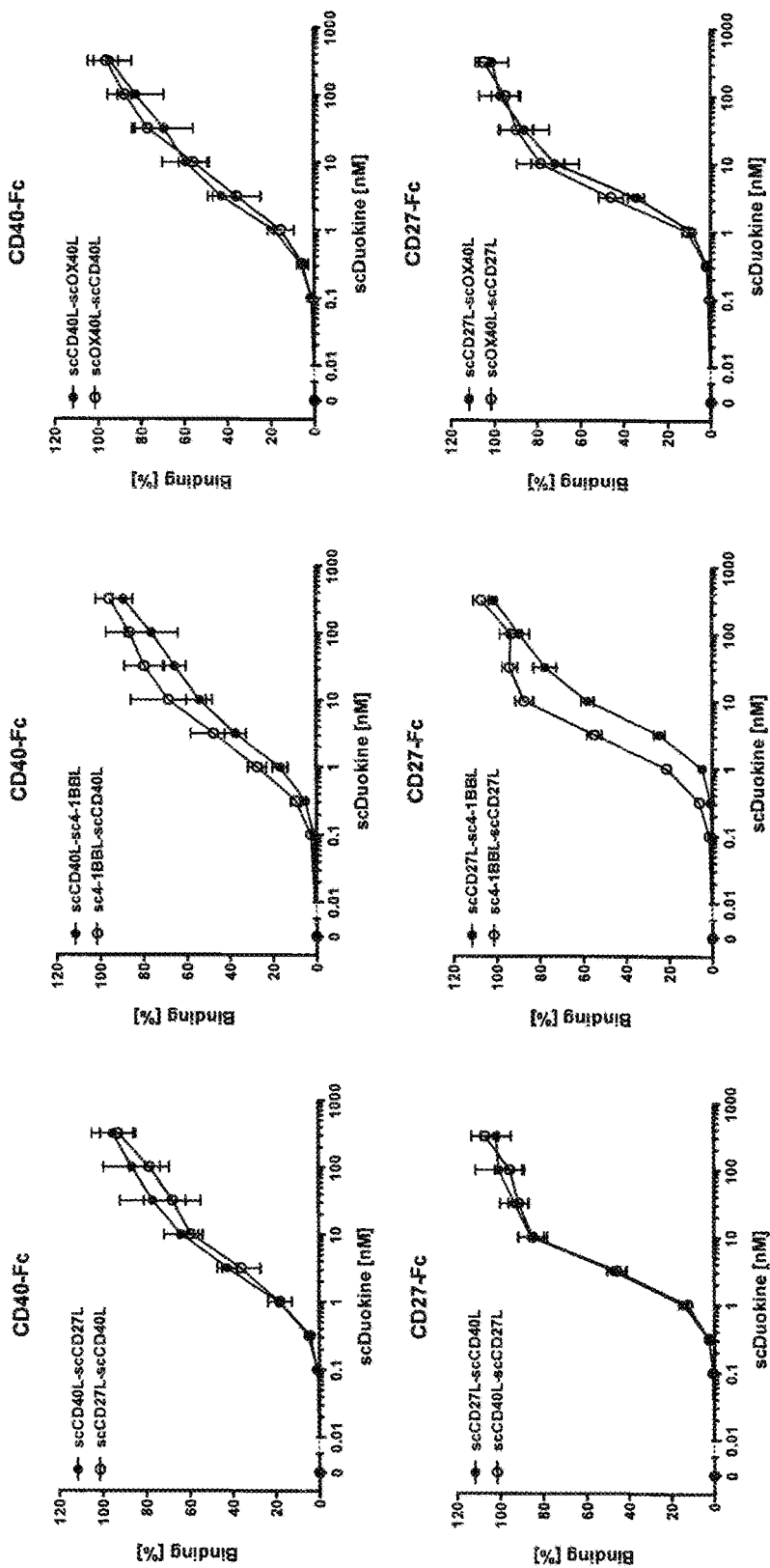
FIGS. 11 A and B. Binding of single-chain Duokines to immobilized CD40-, CD27-, 4-1BB- and OX40-Fc fusion proteins in ELISA (n=3±SD). Duokines were titrated in duplicates starting at a concentration of 316 nM. All single-chain Duokines bound to the respective receptor-Fc fusion proteins in a dose-dependent manner with $EC_{50}$ values in the low nanomolar range.
Figure 11B:
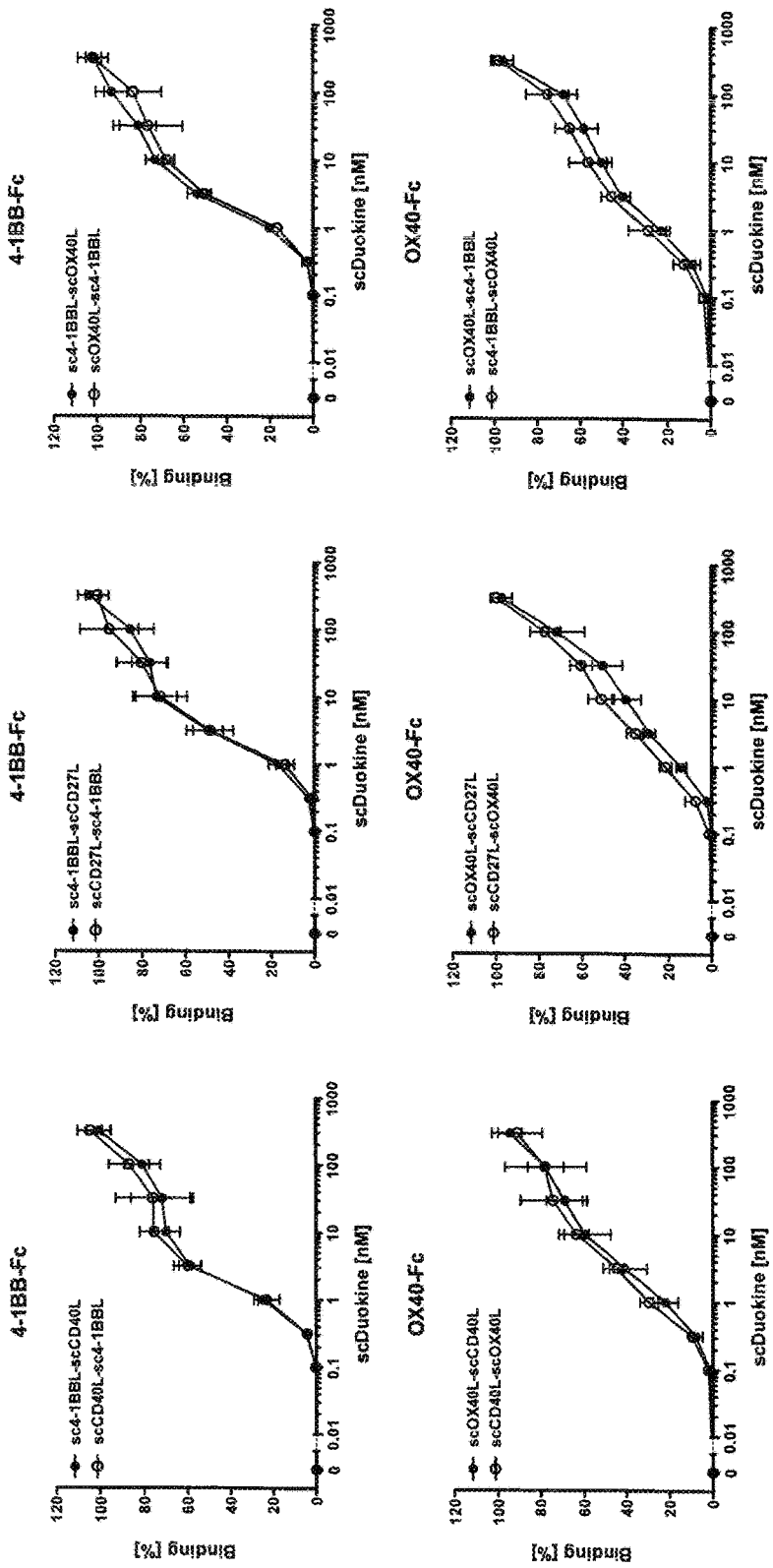

Receptor binding of the single-chain Duokines was analyzed by ELISA using fusion proteins of the extracellular region of CD40, CD27, 4-1BB and OX40, respectively, with the human Fcγ1 region including the hinge region for covalent assembly (CD40-Fc, CD27-Fc, 4-1BB-Fc, OX40-Fc). Receptor-Fc fusion proteins (200 ng/well) were coated overnight at 4° C. and remaining binding sites were blocked with PBS, 2% skimmed milk powder (2% MPBS). Single-chain Duokines were titrated in duplicates starting at a concentration of 316 nM and bound scDuokines were detected with HRP-conjugated mouse anti-FLAG antibody. All scDuokines showed specific binding to their respective receptors and no cross-reactivity with other receptor-Fc fusion proteins was observed (FIG. 10). The interactions between scDuokine and receptor were dose-dependent with $EC_{50}$ values in the low nanomolar ranges (FIG. 11 AB, Tab. 2).

Furthermore, the single-chain Duokines were analyzed by flow cytometry for binding to the fibrosarcoma cell line data was analyzed using FLOWJO® (Tree Star, Ashland, USA). Flow cytometry revealed that all scDuokines bound the cell line expressing their respective receptors (FIG. 12 AB).

Example 6: Bispecific Receptor Binding Properties of Single-Chain Duokines

Bispecificity of the single-chain Duokines was assessed by flow cytometry. $1.5 \times 10^5$ HT1080 cells expressing either the CD40, CD27, 4-1BB or OX40 receptor (HT1080-CD40, HT1080-CD27, HT1080-4-1BB, HT1080-OX40) were incubated with 100 nM scDuokines followed by incubation with the corresponding receptor-Fc fusion protein (10 nM) to detect the second binding site. The scDuokine-receptor-complex was detected using a PE-labeled mouse anti-human Fc antibody, thus only scDuokines recognizing both receptors, one on the cell and the other provided as soluble Fc fusion protein, are able to produce a fluorescent signal. Cells were analyzed using a MACSQuant® 10 analyzer (Miltenyi Biotec, Bergisch Gladbach, Germany) and data was analyzed using FLOWJO® (Tree Star, Ashland, USA). Here, it was shown that all scDuokines were able to bind both receptors simultaneously, establishing dual binding capacity of the single-chain Duokines (FIG. 13 AB).

Example 7: Cloning, Production and Purification of EHD2-Linked Single-Chain Duokines (EHD2-scDuokines)

EHD2-scDuokines were generated by fusing one single-chain cytokine N-terminally and a second single-chain cytokine C-terminally via GGSGG (SEQ ID No: 25) linkers to the IgE heavy-chain domain 2 (EHD2) and cloning into the expression plasmid pSecTagA (Life Technologies, Carlsbad, USA). N-terminally, the EHD2-scDuokines were provided with an Igκ leader sequence for secretion and a FLAG tag for purification and detection. The following EHD2-scDuokines were produced: sc4-1BBL-EHD2-scCD40L, sc4-1BBL-EHD2-scCD27L and scCD40L-EHD2-scCD27L (Tab. 3). All EHD2-scDuokines were produced from stably transfected HEK293 cells and purified from the cell culture supernatant by one-step FLAG affinity chromatography (Sigma-Aldrich) resulting in yields of 3.7 to 8.0 mg/L supernatant.

Figure 14:
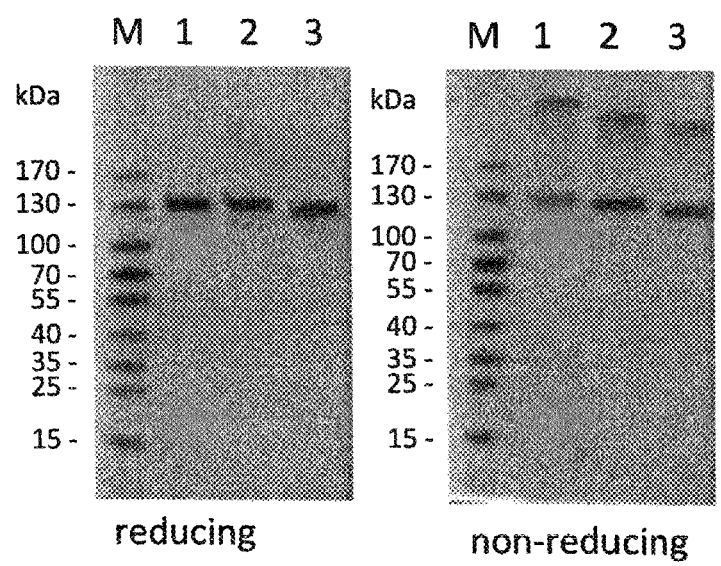
FIG. 14. SDS-PAGE analysis of the purified single-chain Duokines under reducing and non-reducing conditions using a 4-15% polyacrylamide gel (1, sc4-1BBL-EHD2-scCD40L; 2, sc4-1BBL-EHD2-scCD27L; 3, scCD40L-scCD27L). Proteins were visualized by staining with Coomassie Brilliant Blue G250.
Figure 15:
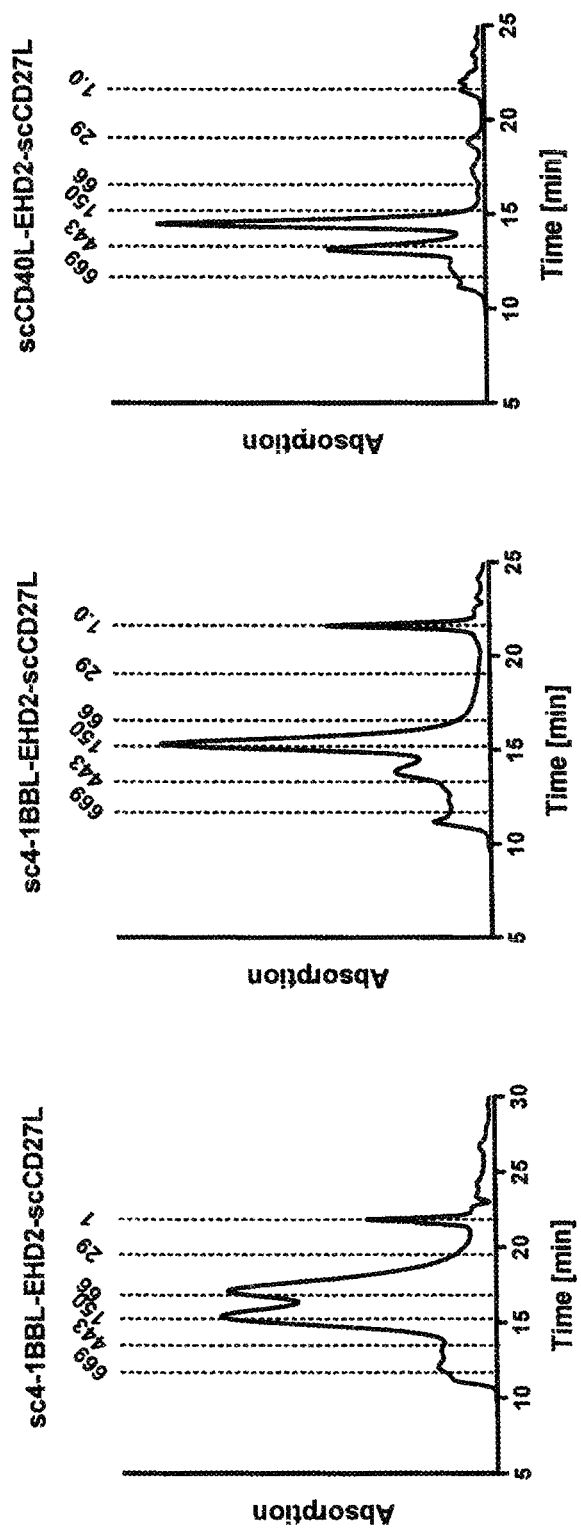
FIG. 15. Size exclusion chromatography (SEC) analysis of the EHD2-scDuokines demonstrating the integrity of the fusion proteins. High-performance liquid chromatography (HPLC) was performed with a Yarra SEC-2000 (Phenomenex) at a flow rate of 0.5 mL/min. Thyroglobulin, alcohol dehydrogenase, bovine serum albumin, carbonic anhydrase and FLAG peptide were used as standard proteins.

EHD2-scDuokines were analyzed in SDS-PAGE under reducing and non-reducing conditions using a 4-15% polyacrylamide gel and visualized by staining with Coomassie Brilliant Blue G250. SDS-PAGE analysis under reducing conditions revealed the expected molecular masses of the hexavalent polypeptide chains (approximately 120 kDa) taking into account the presence of potential N-glycosylation sites in CD40L (1 site; aa 240) and CD27L (2 sites; aa 63 and 170) (FIG. 14, Tab. 3). Additionally, under non-reducing conditions all proteins showed a second band corresponding to dimers formed by disulfide bonds between the EHD2 domains. Approximately 50% of the EHD2-scDuokines showed covalent linkage. Size exclusion chromatography using high performance liquid chromatography on a Yarra SEC-2000 (Phenomenex) with a flow rate of 0.5 mL/min confirmed the homodimeric assembly of the EHD2-scDuokines. Sc4-1BBL-EHD2-scCD27L eluted as a major peak with an apparent molecular mass of 120 kDa corresponding to the hexavalent monomer (calculated molecular mass 122 kDa) and a minor peak with an apparent molecular mass of 200 kDa most likely corresponding to the disulfide-linked dimer (calculated molecular mass 245 kDa). Likewise, scCD40L-EHD2-scCD27L eluted as major peak with an apparent molecular mass of 150 kDa corresponding to the monomer and a second minor peak with an apparent molecular mass of 270 kDa corresponding to the dimer, however, the molecular masses determined via SEC were slightly higher than the calculated ones (110 kDa and 220 kDa, respectively). For sc4-1BBL-EHD2-scCD40L the distribution between monomer and a smaller fragment was equal with two major peaks eluting at apparent molecular masses of 123 kDa and 74 kDa. Additionally, all EHD2-scDuokines showed minor peaks corresponding most likely to higher molecular weight complexes (FIG. 15).

TABLE 3

EHD2-scDuokines and their biochemical properties

| EHD2-scDuokine | N-terminal Cytokine | C-Terminal Cytokine | Linker | # N-glyc. sites per polypeptide chain | Binding ELISA ($EC_{50}$, nM) | Receptor activation ($EC_{50}$, nM) |
|---|---|---|---|---|---|---|
| sc4-1BBL-EHD2-scCD40L | sc4-1BBL | scCD40L | GGSGG-(EHD2)-GGSGG | 4 | 3.06 (CD40-Fc)<br>3.63 (4-1BB-Fc) | 0.75 (CD40)<br>0.27 (4-1BB) |
| sc4-1BBL-EHD2-scCD27L | sc4-1BBL | scCD27L | GGSGG-(EHD2)-GGSGG | 7 | 2.00 (CD27-Fc)<br>1.93 (4-IBB-Fc) | 1.64 (4-1BB) |
| scCD40L-EHD2-scCD27L | scCD40L | scCD27L | GGSGG-(EHD2)-GGSGG | 9 | 4.05 (CD40-Fc)<br>2.03 (CD27-Fc) | 2.00 (CD40) |

Example 8: Receptor Binding Properties of EHD2-Linked Single-Chain Duokines (EHD2-scduokines)

Figure 16:
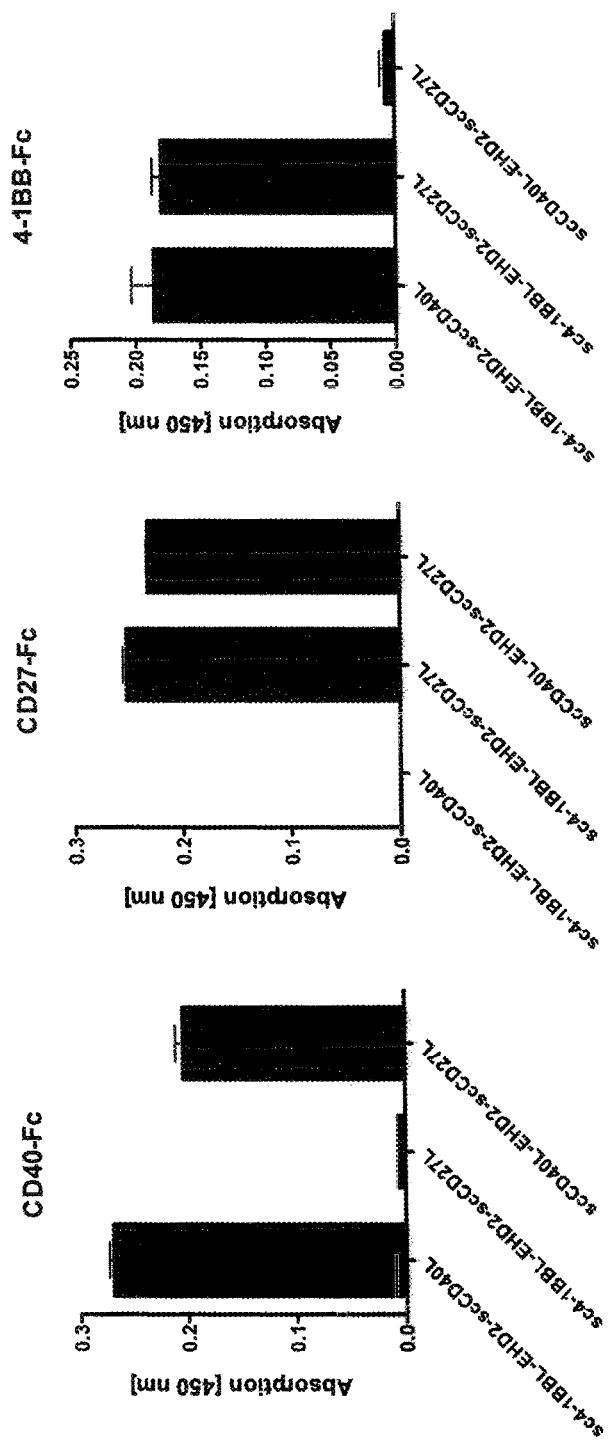
FIG. 16. Binding of EHD2-scDuokines (100 nM) to immobilized CD40-, CD27-, 4-1BB- and OX40-Fc fusion proteins in ELISA. All EHD2-scDuokines bound to the respective receptor-Fc fusion proteins, and no cross-reactivity was detected.
Figure 17:
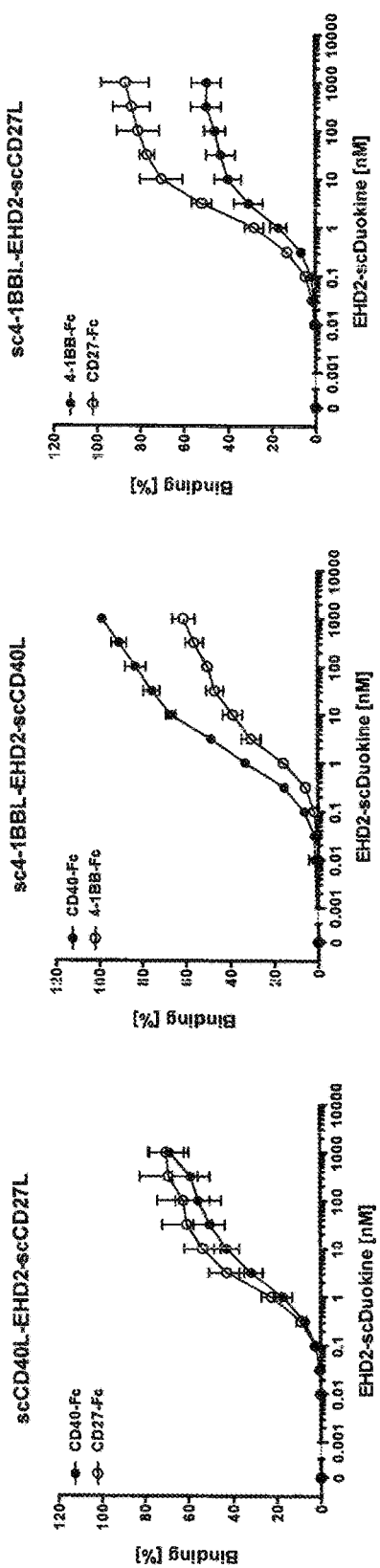
FIG. 17. Binding of EHD2-linked single-chain Duokines to immobilized CD40-, CD27-, 4-1BB- and OX40-Fc fusion proteins in ELISA (n=3±SD). EHD2-scDuokines were titrated in duplicates starting at a concentration of 316 nM. All EHD2-scDuokines bound to the respective receptor-Fc fusion proteins in a dose-dependent manner with $EC_{50}$ values in the low nanomolar range.

Receptor binding of the EHD2-scDuokines was analyzed by ELISA using fusion proteins of the extracellular region of CD40, CD27 and 4-1BB, respectively, with the human Fcγ1 region including the hinge region for covalent assembly (CD40-Fc, CD27-Fc, 4-1BB-Fc). Receptor-Fc fusion proteins (200 ng/well) were coated overnight at 4° C. and remaining binding sites were blocked with PBS, 2% skimmed milk powder (2% MPBS). EHD2-scDuokines were titrated in duplicates starting at a concentration of 316 nM and bound EHD2-scDuokines were detected with HRP-conjugated mouse anti-FLAG antibody. All EHD2-scDuokines showed specific binding to their respective receptors and no cross-reactivity with other receptor-Fc fusion proteins was observed (FIG. 16). The interactions between EHD2-scDuokine and receptor were dose-dependent with $EC_{50}$ values in the low nanomolar ranges (FIG. 17, Tab. 3).

Figure 18:
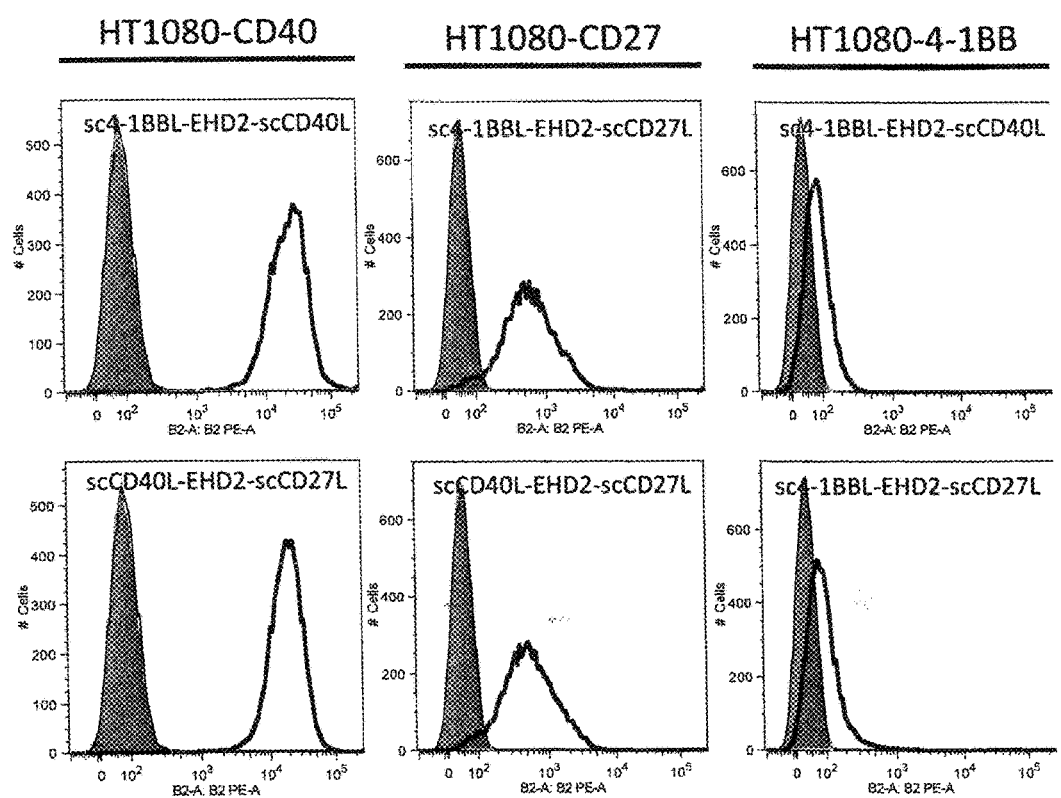
FIG. 18. Binding of EHD2-scDuokines (100 nM) to CD40-, CD27-, 4-1BB-expressing HT1080 cells analyzed by flow cytometry. Bound EHD2-scDuokines were detected with a PE-labeled anti-FLAG antibody (grey, cells alone; thin line cells incubated with PE-labeled anti-FLAG antibody; bold line, cells incubated with EHD2-scDuokines).

Furthermore, the EHD2-scDuokines were analyzed by flow cytometry for binding to the fibrosarcoma cell line HT1080 engineered to express the CD40, CD27 or 4-1BB receptor, respectively (HT1080-CD40, HT1080-CD27, HT1080-4-1BB). Here, $1.5 \times 10^5$ cells were incubated with 100 nM EHD2-scDuokines and binding was detected using a PE-labeled mouse anti-FLAG antibody. Cells were analyzed using a MACSQuant® 10 analyzer (Miltenyi Biotec, Bergisch Gladbach, Germany) and data was analyzed using FLOWJO® (Tree Star, Ashland, USA). Flow cytometry revealed that all EHD2-scDuokines bound the cell line expressing their respective receptors (FIG. 18).

Example 9: Bispecific Receptor Binding Properties of EHD2-Linked Single-Chain Duokines (EHD2-scDuokines)

Bispecificity of the EHD2-scDuokines was assessed by flow cytometry. $1.5 \times 10^5$ HT1080 cells expressing either the CD40, CD27 or 4-1BB receptor (HT1080-CD40, HT1080-

Figure 19:
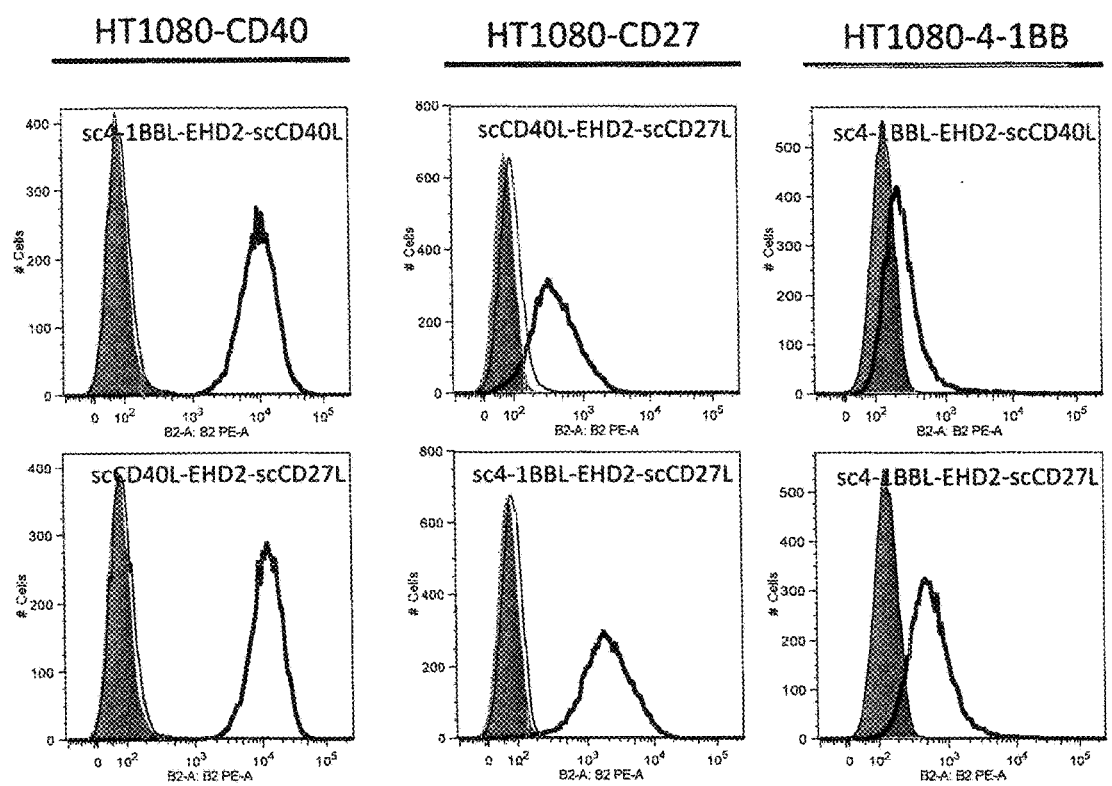
FIG. 19. Bispecificity of EHD2-scDuokines was analyzed by flow cytometry. After binding of EHD2-scDuokines (100 nM) to CD40-, CD27-, 4-1BB- and OX40-expressing HT1080 cells, the EHD2-scDuokines were detected using the corresponding receptor-Fc fusion proteins (10 nM) and a PE-labeled anti-human Fc antibody. TNFR1-Fc was included as negative control (grey, cells incubated with PE-labeled anti-human Fc antibody; thin line, cells incubated with EHD2-scDuokines and TNFR1-Fc; bold line, cells incubated with EHD2-scDuokines and CD40-, CD27-, 4-1BB- or OX40-Fc).

CD27, HT1080-4-1BB) were incubated with 100 nM EHD2-scDuokines followed by incubation with the corresponding receptor-Fc fusion protein (10 nM) to detect the second binding site. The EHD2-scDuokine-receptor-complex was detected using a PE-labeled mouse anti-human Fc antibody, thus only EHD2-scDuokines recognizing both receptors, one on the cell and the other provided as soluble Fc fusion protein, are able to produce a fluorescent signal. Cells were analyzed using a MACSQuant® 10 analyzer (Miltenyi Biotec, Bergisch Gladbach, Germany) and data was analyzed using FLOWJO® (Tree Star, Ashland, USA). Here, it was shown that all EHD2-scDuokines were able to bind both receptors simultaneously, establishing dual binding capacity of the EHD2-scDuokines (FIG. 19).

Example 10: Receptor Activation of EHD2-Linked Single-Chain Duokines (EHD2-scDuokines)

Figure 20:
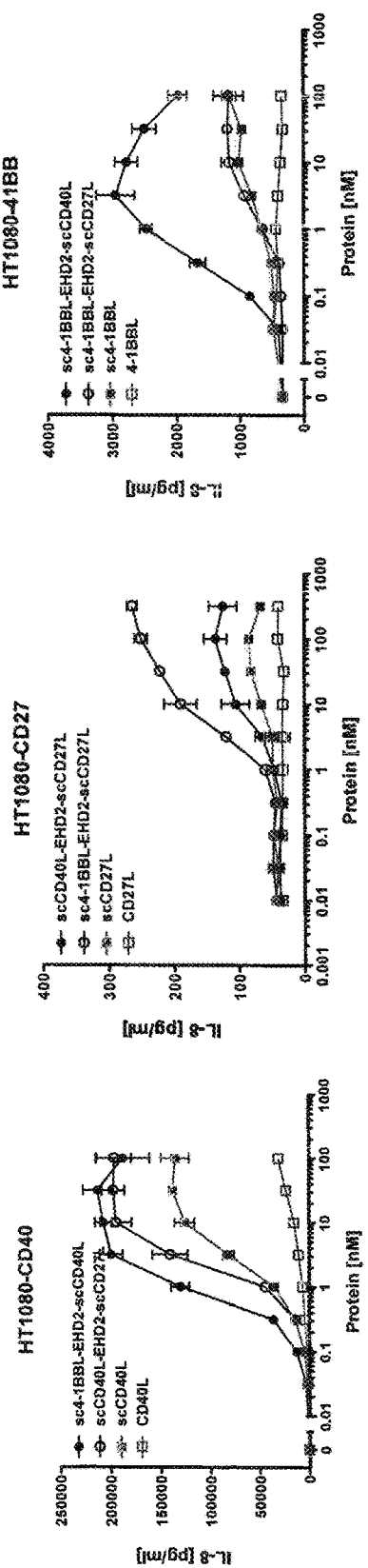
FIG. 20. Receptor activation of EHD2-scDuokines analyzed by IL-8 release from CD40- and 4-1BB-expressing HT1080 cells (n=3±SD) or from CD27-expressing HT1080 cells (n=1±SD). $2 \times 10^4$ HT1080 cells were incubated with serial dilutions of the EHD2-scDuokines and the amount of IL-8 in the supernatant was detected via ELISA after 18 hours incubation. Monomeric ligands and the single-chain derivatives thereof were included as controls.

In order to assess the bioactivity of EHD2-scDuokines, receptor activation was analyzed by EHD2-scDuokine-mediated secretion of IL-8 from HT1080 cells (FIG. 20, Tab. 3). Therefore, $2 \times 10^4$ HT1080 cells expressing either the CD40, CD27 or 4-1BB, respectively, were seeded overnight onto 96-well microtiter plates and the next day the supernatant was exchanged to remove constitutively produced IL-8. Afterwards the cells were incubated in duplicates with serial dilutions of EHD2-scDuokines starting at a concentration of 316 nM for 18 hours. The amount of IL-8 in the supernatant was determined using an IL-8 ELISA Kit (Immunotools, Freiburg, Germany) according to the manufacturer's instructions. For comparison the corresponding monospecific trimeric, soluble ligands (CD40L, CD27L) or their soluble single-chain derivatives (scCD40L, scCD27L, sc4-1BBL) were included. On HT1080-CD40 cells, the tested EHD2-scDuokines induced strong IL-8 secretion in a dose-dependent manner resulting in IL-8 concentrations up to 225 ng/mL. Both EHD2-scDuokines containing scCD40L (sc4-1BBL-EHD2-scCD40L and scCD40L-EHD2-scCD27L) led to stronger CD40 receptor activation than with monospecific, soluble scCD40L. IL-8 secretion induced by activation of 4-1BB was observable for both EHD2-scDuokines targeting 4-1BB, but sc4-1BBL-EHD2-scCD40L showed a considerably increased activity compared to sc4-1BBL-EHD2-scCD27L, which was as active as monospecific, soluble sc4-1BBL. Sc4-1BBL-EHD2-scCD27L and scCD40L-EHD2-scCD27L were both able to induce IL-8 secretion upon activating CD27, but the combination of sc4-1BBL and scCD27L within the EHD2-scDuokine showed stronger induction of IL-8 release (FIG. 20). These experiments established that the EHD2-scDuokines are capable in inducing receptor activation resulting in IL-8 release in this assay system.

Example 11: Effects of Duokines and Single-Chain Duokines on T Cell Proliferation In order to assess the proliferative capacities of Duokines and scDuokines, the proliferation of T cells in bulk PBMC populations was analyzed. To that end, human PBMCs were isolated from healthy donors, stored frozen at −80° C. and thawed one day prior to the experiment. PBMCs were stained at a concentration of $1 \times 10^6$ cells/mL with 625 nM carboxyfluorescein diacetate succinimidyl ester (CFSE) using the CellTrace® CFSE Cell Proliferation Kit (Life Technologies), following the manufacturer's instructions. For primary stimulation of T cells a cross-linked anti-human CD3 monoclonal antibody (UCHT-1, R&D systems, Minneapolis, USA) was used. Proliferation induced by the fusion proteins in solution was assessed by incubating $1.5 \times 10^5$ PBMC per well with serial dilutions of the different Duokines or scDuokines for 6 days, followed by flow cytometry analysis. Additional antibody-mediated staining was carried out to identify T cells (CD3-PE, Immunotools, Friesoythe, Germany).

Figure 21:
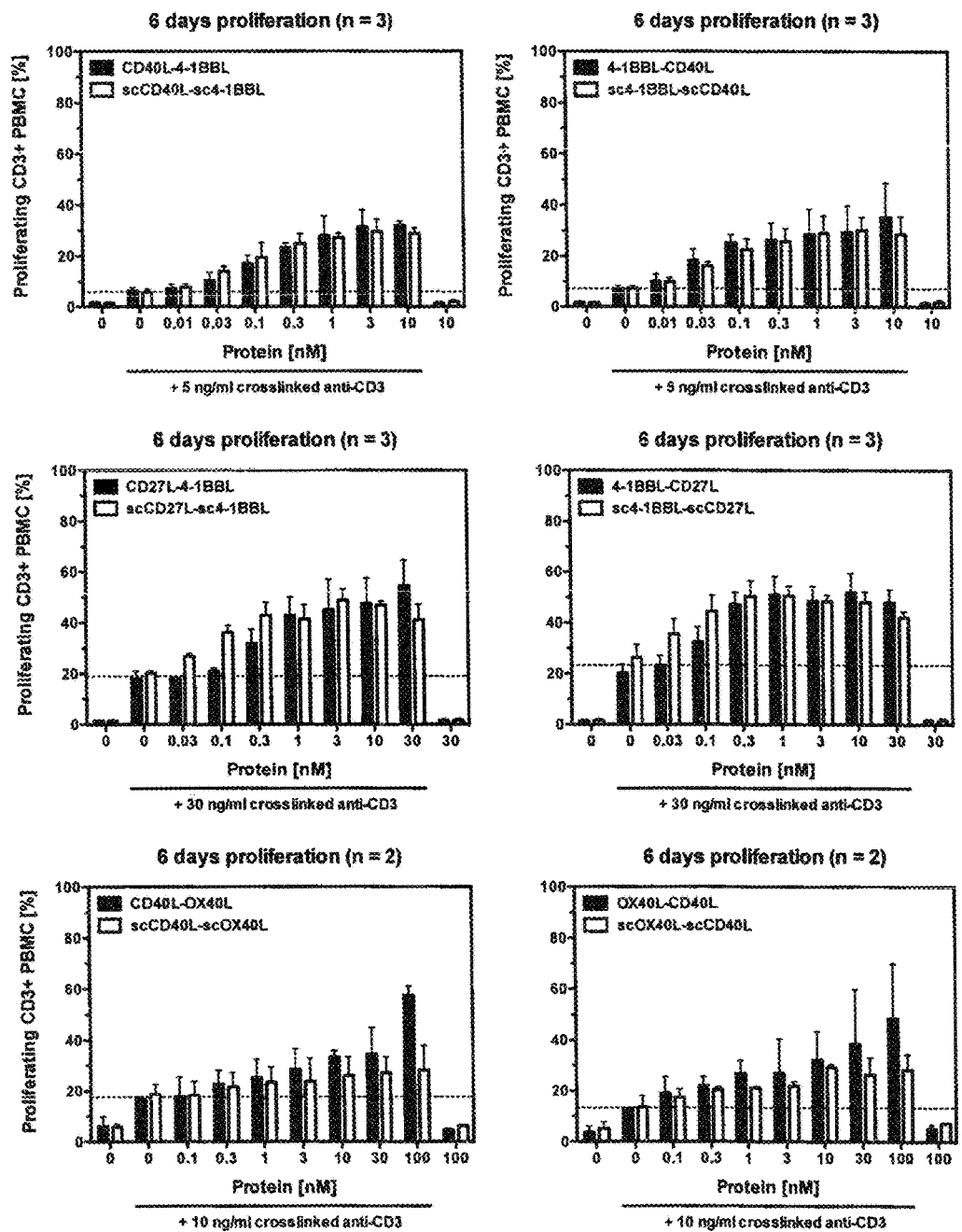
FIG. 21. Proliferation of T cells after stimulation with Duokines or single-chain Duokines. $1.5 \times 10^5$ CFSE-stained human PBMCs (bulk population) were incubated with serial dilutions of Duokines or single-chain Duokines in presence of cross-linked anti-human CD3 antibody as primary suboptimal stimulus. After 6 days, proliferation of T cells was assessed by flow cytometry.

All tested PBMC batches needed primary stimulation with cross-linked anti-human CD3 mAb to proliferate. Here, a suboptimal antibody concentration (5-30 ng/ml) was used to induce T cell proliferation in only up to 20 percent of T cells. All tested Duokines and scDuokines (combinations of CD40L and 4-1BBL, CD27L and 4-1BBL or CD40L and OX40L) were inactive when applied without primary stimulus, but induced T cell proliferation in a dose-dependent manner when applied in combination with cross-linked anti-human CD3 mAb. Here, proliferation was enhanced two- to threefold already at low nanomolar concentrations of the fusion proteins. In all cases no differences in proliferative effects were detectable between the different orientations of the cytokines within the Duokines or single-chain Duokines. Fusion proteins containing CD40L and 4-1BBL or CD27L and 4-1BBL showed the same proliferative capacities independent of the used format (FIG. 21).

Example 12: Vector Design, Cloning and Production of In Vitro Transcribed RNA (IVT-RNA) mRNA Encoded Duokines and scDuokines Plasmid constructs (pST1-hAg-Kozak-sec-2hBgUTR-A120), which were used as templates for in vitro transcription of RNAs encoding tumor necrosis factor receptor (TNFR) ligands and fusion proteins thereof, were based on pST1-2hBgUTR-A120 (Holtkamp S. et al. (2006), Blood, 108(13):4009-17). The plasmid backbone was derived from pCMV-Script (Stratagene, La Jolla/CA, USA) by introducing a T7 promotor, the 5'-human alpha-globulin UTR, the Kozak sequence, a 78-bp signal peptide derived from an MHC class I molecule (Sec; secretion signal), two copies of the human 3'beta-globulin UTR, the 120 bp poly(A)-tail and the kanamycin resistance gene. Inserts encoding for TNFR ligands or fusion proteins thereof (consistent with Duokines or scDuokines) were introduced by cold fusion reactions with PCR products (Cold fusion kit, Biocat). DNA sequences of the relevant protein encoding section are listed in Table 4 (Tab. 4).

Figure 22:
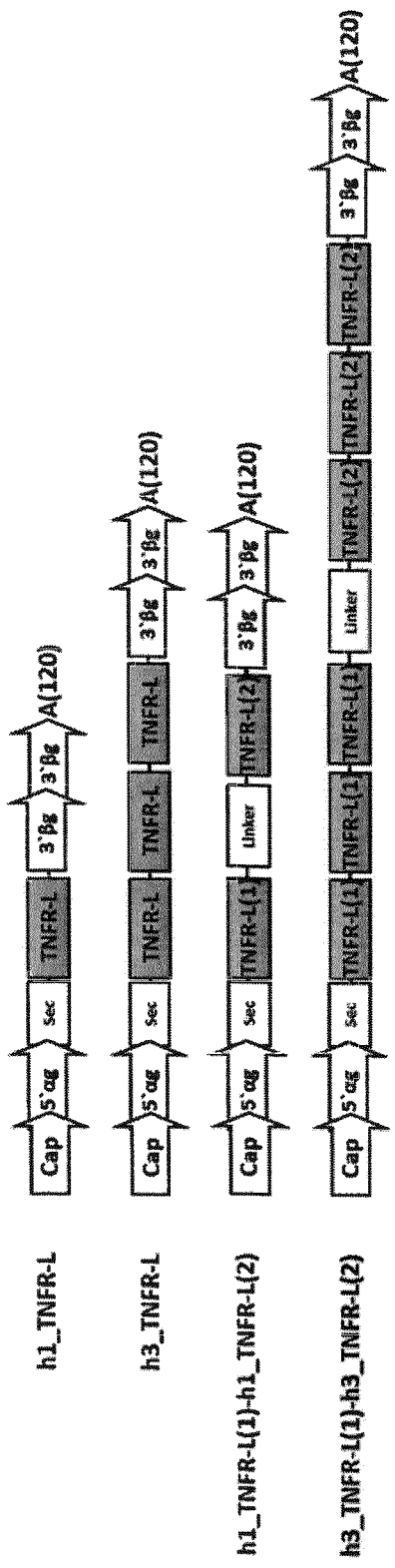
FIG. 22. Vector design for in vitro transcription of mRNAs encoding extracellular domains of TNFR ligands and fusion proteins thereof. The plasmid constructs pST1-hAg-Kozak-sec(opt)-INSERT-2hBgUTR-A120 were used as templates for in vitro transcription of RNAs encoding TNF-receptor (TNFR) ligands and fusion proteins thereof. The INSERTs encoded extracellular domains of TNFR ligands, which are functionally active as homotrimers. Two different kinds of coding sequences for those TNF-receptor ligands were generated: (i) inserts including one single extracellular domain of the TNF receptor, therefore coding for non-covalent bound trimers and (ii) single-chain constructs, in which the inserts included three copies of the extracellular domain separated by short linker domains (encoded amino acids: $G_3SG_3$) therefore coding for covalent bound trimers. To generate fusion proteins of two TNFR ligands they were connected by a linker. Nomenclature: Constructs encoding human protein sequences are shortened by an "h", murine protein sequences are shortened by an "m". The numbers "1" and "3" indicate the quantity of copies of the TNFR ligand extracellular domains encoded.

Coding sequences for trimeric human TNFR ligands (CD40L, CD27L, OX40L and 4-1BBL) were introduced by two different strategies as follows: (i) one copy of the extracellular sequence of the indicated human TNFR ligand, which is specified as h1_TNFR-ligand (h1_CD27L, h1_CD40L, h1_OX40L or h1_41BBL), and (ii) three copies of the extracellular sequence of the indicated human TNFR ligand connected in line and separated by a GS-linker, such a human insert is specified as h3_TNFR-ligand (h3_CD40L, h3_CD27L, h3_OX40L or h3_41BBL) and corresponds to the single-chain proteins described above. To get coding sequences for fusion proteins two h1_TNFR-ligand or h3_TNFR-ligand sequences were connected by a 15-amino acid linker ((G4S)$_3$-Linker), respectively (FIG. 22). RNA-transcripts h1_TNFR-L(1)-h1_TNFR-L(2) correspond to Duokines and transcripts h3_TNFR-L(1)-h3_TNFR-L(2) correspond to scDuokines. Protein sequences of the single h1_TNFR-ligands and h3_TNFR-ligands are listed in Table 5 (Tab. 5).

For generation of IVT-RNAs, plasmids were linearized downstream of the poly(A) tail using a class II restriction endonuclease. Linearized plasmids were purified by magnetic beads (DYNABEADS® MYONE™ Carboxylic Acid; Invitrogen), quantified spectrophotometrically, and subjected to in vitro transcription with T7 RNA polymerase (Thermo Scientific) according to the manufacturer's instructions. Additionally, the cap analog β-S-ARCA (D2) was incorporated and finally the RNA was purified using MEGA Kit (Ambion).

TABLE 4

DNA/amino acid sequences of particular sections of DST1-hAg-Kozak-sec-INSERT-2hBgUTR-A120 and other plasmids used in accordance with the present invention

| Backbone | DNA sequence (amino acid sequence) |
|---|---|
| hAg-Kozak | ATTCTTCTGGTCCCCACAGACTCAGAGAGAACCCGCCACC (SEQ ID NO.: 13) |
| Sec | ATGAGAGTGACCGCCCCCAGAACCCTGATCCTGCTGCTGTCTGGCGCCCTGGCCCTGACAGAGACATGGG CCGGAAGCGGATCC (SEQ ID NO.: 14)<br>(M R V T A P R T L I L L L S G A L A L T E T W A G S G S; SEQ ID NO.: 15) |
| 2hBgUTR | CTCGAGAGCTCGCTTTCTTGCTGTCCAATTTCTATTAAAGGTTCCTTTGTTCCCTAAGTCCAACTACTAAACT GGGGGATATTATGAAGGGCCTTGAGCATCTGGATTCTGCCTAATAAAAAACATTTATTTTCATTGCTGCGT CGAGAGCTCGCTTTCTTGCTGTCCAATTTCTATTAAAGGTTCCTTTGTTCCCTAAGTCCAACTACTAAACTG GGGGATATTATGAAGGGCCTTGAGCATCTGGATTCTGCCTAATAAAAAACATTTATTTTCATTGCTGCGTC (SEQ ID NO.: 16) |
| A120 | GAGACCTGGTCCAGAGTCGCTAGCAAAAAAAAAAAAAAAAAAAAAAAAAAAAAAAGCATATGACTAAAAA AAAAAAAAAAAAAAAAAAAAAAAAAAAAAAAAAAAAAAAAAAAAAAAAAAAAAAAAAAAAAAAAAAAAA (SEQ ID NO.: 17) |
| (G4S)3-Linker | GGAGGCGGTGGTAGTGGAGGTGGCGGGTCCGGTGGAGGTGGAAGC (SEQ ID NO.: 18)<br>(G G G G S G G G G S G G G G S; SEQ ID NO.: 19) |

TABLE 5

Amino acid sequences of the variable inserts of pST1-hAg-Kozak-sec-INSERT-2hBgUTR-A120 and plasmids encoding the extracellular domains of TNFR ligands (linker sequences are underlined)

| Insert | related protein | related amino acid of full length protein | Amino acid sequences |
|---|---|---|---|
| h1_CD40L | CD40L | aa 51-261 | D K I E D E R N L H E D F V F M K T I Q R C N T G E R S L S L L N C E E I K S Q F E G F V K D I M L N K E E T K K E N S F E M Q K G D Q N P Q I A A H V I S E A S S K T T S V L Q W A E K G Y Y T M S N N L V T L E N G K Q L T V K R Q G L Y Y I Y A Q V T F C S N R E A S S Q A P F I A S L C L K S P G R F E R I L L R A A N T H S S A K P C G Q Q S I H L G G V F E L Q P G A S V F V N V T D P S Q V S H G T G F T S F G L L K L (SEQ ID NO.: 5) |
| h3_CD40L | scCD40L | aa 116-261 | G D Q N P Q I A A H V I S E A S S K T T S V L Q W A E K G Y Y T M S N N L V T L E N G K Q L T V K R Q G L Y Y I Y A Q V T F C S N R E A S S Q A P F I A S L C L K S P G R F E R I L L R A A N T H S S A K P C G Q Q S I H L G G V F E L Q P G A S V F V N V T D P S Q V S H G T G F T S F G L L K L <u>G G G S G G G G</u> D Q N P Q I A A H V I S E A S S K T T S V L Q W A E K G Y Y T M S N N L V T L E N G K Q L T V K R Q G L Y Y I Y A Q V T F C S N R E A S S Q A P F I A S L C L K S P G R F E R I L L R A A N T H S S A K P C G Q Q S I H L G G V F E L Q P G A S V F V N V T D P S Q V S H G T G F T S F G L L K L <u>G G G S G G G G</u> D Q N P Q I A A H V I S E A S S K T T S V L Q W A E K G Y Y T M S N N L V T L E N G K C I L T V K R Q G L Y Y I Y A Q V T F C S N R E A S S Q A P F I A S L C L K S P G R F E R I L L R A A N T H S S A K P C G Q Q S I H L G G V F E L Q P G A S V F V N V T D P S Q V S H G T G F T S F G L L K L (SEQ ID NO.: 9) |
| h1_CD27L | CD27L | aa 52-193 | S L G W D V A E L Q L N H T G P Q Q D P R L Y W Q G G P A L G R S F L H G P E L D K G Q L R I H R D G I Y M V H I Q V T L A I C S S T T A S R H H P T T L A V G I C S P A S R S I S L L R L S F H Q G C T I A S Q R L T P L A R G D T L C T N L T G T L L P S R N T D E T F F G V Q W V R P (SEQ ID NO.: 6) |
| h3_CD27L | scCD27L | aa 52-193 | S L G W D V A E L Q L N H T G P Q Q D P R L Y W Q G G P A L G R S F L H G P E L D K G Q L R I H R D G I Y M V H I Q V T L A I C S S T T A S R H H P T T L A V G I C S P A S R S I S L L R L S F H Q G C T I A S Q R L T P L A R G D T L C T N L T G T L L P S R N T D E T F F G V Q W V R P <u>G G G S G G G S</u> L G W D V A E L Q L N H T G P Q Q D P R L Y W Q G G P A L G |

TABLE 5-continued

Amino acid sequences of the variable inserts of pST1-hAg-Kozak-sec-INSERT-2hBgUTR-A120 and plasmids encoding the extracellular domains of TNFR ligands (linker sequences are underlined)

| Insert | related protein | related amino acid of full length protein | Amino acid sequences |
|---|---|---|---|
|  |  |  | R S F L H G P E L D K G Q L R I H R D G I Y M V H I Q V T L A I C S S T T A S R H H P T T L A V G I C S P A S R S I S L L R L S F H Q G C T I A S Q R L T P L A R G D T L C T N L T G T L L P S R N T D E T F F G V Q W V R <u>P G G G S G G G</u> S L G W D V A E L Q L N H T G P Q Q D P R L Y W Q G G P A L G R S F L H G P E L D K G Q L R I H R D G I Y M V H I Q V T L A I C S S T T A S R H H P T T L A V G I C S P A S R S I S L L R L S F H Q G C T I A S Q R L T P L A R G D T L C T N L T G T L L P S R N T D E T F F G V Q W V R P (SEQ ID NO.: 10) |
| h1_4-1BBL | 4-1BBL | aa 71-254 | R E G P E L S P D D P A G L L D L R Q G M F A Q L V A Q N V L L I D G P L S W Y S D P G L A G V S L T G G I S Y K E D T K E L V V A K A G V Y Y V F F Q L E L R R V V A G E G S G S V S L A L H L Q P L R S A A G A A A L A L T V D L P P A S S E A R N S A F G F Q G R L L H L S A G Q R L G V H L H T E A R A R H A W Q L T Q G A T V L G L F R V T P E I P A G L P S P R S E (SEQ ID NO.: 7) |
| h3_4-1BBL | sc4-1BBL | aa 71-254 | R E G P E L S P D D P A G L L D L R Q G M F A Q L V A Q N V L L I D G P L S W Y S D P G L A G V S L T G G L S Y K E D T K E L V V A K A G V Y Y V F F Q L E L R R V V A G E G S G S V S L A L H L Q P L R S A A G A A A L A L T V D L P P A S S E A R N S A F G F Q G R L L H L S A G Q R L G V H L H T E A R A R H A W Q L T Q G A T V L G L F R V T P E I P A G L P S P R S E <u>G G G G S G G G G S G G G G S G G G G S G G G G S</u> R E G P E L S P D D P A G L L D L R Q G M F A Q L V A Q N V L L I D G P L S W Y S D P G L A G V S L T G G L S Y K E D I K E L V V A K A G V Y Y V F F Q L E L R R V V A G E G S G S V S L A L H L Q P L R S A A G A A A L A L T V D L P P A S S E A R N S A F G F Q G R L L H L S A G Q R L G V H L H T E A R A R H A W Q L T Q G A T V L G L F R V T P E I P A G L P S P R S E <u>G G G G S G G G G S G G G G S G G G G S</u> R E G P E L S P D D P A G L L D L R Q G M F A C I L V A C I N V L L I D G P L S W Y S D P G L A G V S L T G G L S Y K E D T K E L V V A K A G V Y Y V F F Q L E L R R V V A G E G S G S V S L A L H L Q P L R S A A G A A A L A L T V D L P P A S S E A R N S A F G F Q G R L L H L S A G Q R L G V H L H T E A R A R H A W Q L T Q G A T V L G L F R V T P E I P A G L P S P R S E (SEQ ID NO.: 11) |
| h1-OX40L | OX40L | aa 51-183 | Q V S H R Y P R I Q S I K V Q F T E Y K K E K G F I L T S Q K E D E I M K V Q N N S V I I N C D G F Y L I S L K G Y F S Q E V N I S L H Y Q K D E E P L F Q L K K V R S V N S L M V A S L T Y K D K V Y L N V T T D N T S L D D F H V N G G E L I L I H Q N P G E F C V L (SEQ ID NO.: 8) |
| h3_OX40L | scOX40L | aa 51-183 | Q V S H R Y P R I Q S I K V Q F T E Y K K E K G F I L T S Q K E D E I M K V Q N N S V I I N C D G F Y L I S L K G Y F S Q E V N I S L H Y Q K D E E P L F Q L K K V R S V N S L M V A S L T Y K D K V Y L N V T I D N T S L D D F H V N G G E L I L I H Q N P G E F C V L <u>G G G S G G G</u> Q V S H R Y P R I Q S I K V Q F T E Y K K E K G F I L T <u>S</u> Q K E D E I M K V Q N N S V I I N C D G F Y L I S L K G Y F S Q E V N I S L H Y Q K D E E P L F Q L K K V R S V N S L M V A S L T Y K D K V Y L N V T T D N T S L D D F H V N G G E L I L I H Q N P G E F C V L <u>G G G S G G G</u> Q V S H R Y P R I Q S I K V Q F T E Y K K E K G F I L T S Q K E D E I M K V Q N N S V I I N C D G F Y L I S L K G Y F S Q E V N I S L H Y Q K D E E P L F Q L K K V R S V N S L M V A S L T Y K D K V Y L N V T T D N T S L D D F H V N G G E L I L I H Q N P G E F C V L (SEQ ID NO.: 12) |

Example 13: Intracellular Expression of TNF-Receptor Ligands after IVT-RNA Electroporation K562, a human cell line derived from chronic myeloid leukemia (obtained from ATCC, Manassas, Va., USA) was cultivated in RPMI 1640 GlutaMAX® supplemented with 5% FCS (both Gibco), 100 IU/mL penicillin, and 100 µg/mL streptomycin (Gibco). For electroporation of K562 in a 96-well plate-system, cells were washed once in X-Vivo15 medium (Lonza) and re-suspended to 500.000 cells/150 µl in X-Vivo15 again. 150 µl of cell suspension were pipetted into the 96-well plate already containing the required IVT-RNAs for multi-well-electroporation (Biorad). After mixing, electroporation was performed in the Gene Pulser MXcell electroporation system from Biorad (250 V, 1×30 ms pulse), which is a 96-well electroporation device. Immediately after electroporation, cells were transferred into a new culture plate by adding 100 µl of fresh medium and rested for about 6 hours in the incubator. For intracellular staining of K562, cells were then incubated with GOLGIPLUG® and GOLGISTOP® (BD Biosciences, San Jose, Calif.) for 16 hours (overnight) according to the manufacturer's protocol. On the next day, cells were washed with PBS and fixed for 20 min in BD Cytofix Buffer (BD Biosciences) at room temperature. After that, cells were washed again in PBS and permeabilized by washing and transferring the cells into 1× Perm/Wash Buffer (BD Biosciences). After 10 min of incubation cells were stained with anti-TNFR-ligand antibodies diluted in 1× Perm/Wash Buffer for 30 min at room temperature in the dark followed by 3 washing steps with 1× Perm/Wash Buffer. Cells were then directly analyzed by flow cytometry using a FACS Canto II flow cytometer (BD Biosciences). Analysis was performed using the FLOWJO® software (Tree Star, Ashland, Oreg., USA).

Figure 23:
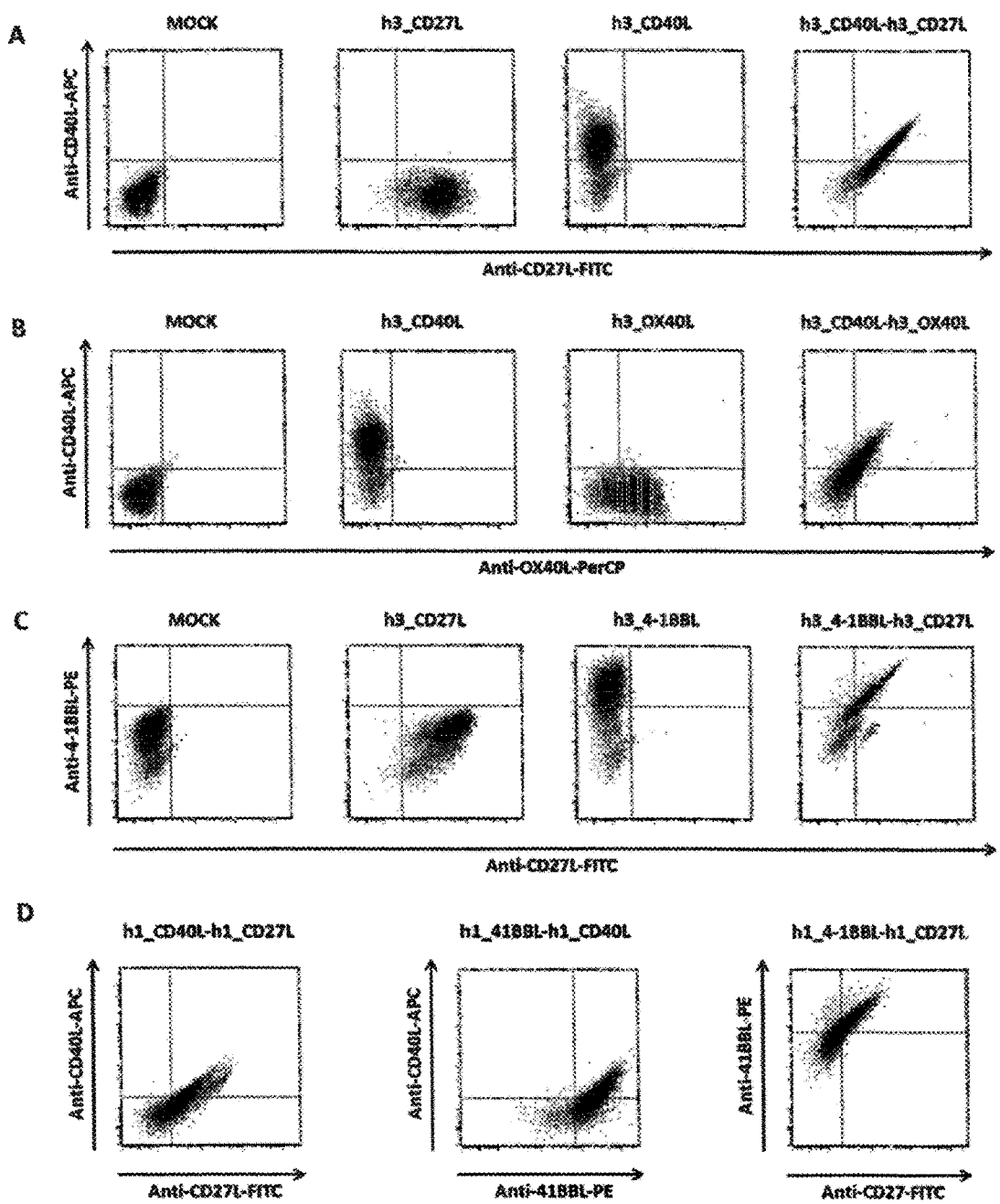
FIGS. 23 A-D. Intracellular expression of fusion proteins after IVT-RNA electroporation. K562 cells were electroporated with IVT-RNA encoding extracellular domains of TNFR ligands or fusion proteins thereof. 6 hours after electroporation, protein export was blocked with GOLGI-PLUG® and GolgiSTOP and after 12 hours of incubation, cells were stained intracellularly for CD27L, CD40L, OX40L or 4-1BBL, respectively. As negative control, K562 cells were electroporated without RNA (MOCK) and stained accordingly. (A) Intracellular staining of TNFR ligands upon electroporation of h3_CD40L-h3_CD27L construct in comparison to h3_CD27L- and h3_CD40L-single constructs. (B) Intracellular staining of TNFR ligands upon electroporation of h3_CD40L-h3_OX40L construct in comparison to h3_OX40L- and h3_CD40L-single constructs. (C) Intracellular staining of TNFR ligands upon electroporation of h3_4-1BBL-h3_CD27L construct in comparison to h3_CD27L- and h3_4-1BBL-single constructs. (D) Intracellular staining of TNFR ligands upon electroporation of h1_CD40L-h1_CD27L, h1_4-1BBL-h1_CD40L and h1_4-1BBL-h1_CD27L constructs.

Electroporation of mRNA encoded TNFR ligands, Duokines and scDuokines resulted in intracellular protein expression, which was detectable by intracellular antibody staining. Upon electroporation of single TNFR ligand constructs, CD27L, CD40L, OX40L and 4-1BBL were detected by the corresponding antibodies (FIG. 23 A-C). scDuokines, encoded by h3_CD40L-h3_CD27L, h3_CD40L-h3_OX40L and h3_4-1BBL-h3_CD27L, were detected accordingly with each of the two corresponding anti-TNFR-ligand antibodies (FIG. 23 A-C). Duokines, encoded by h1_CD40L-h1_CD27L, h1_41BBL-h1_CD40L and h1_4-1BBL-h1_CD27L, were detected accordingly with each of the two corresponding anti-TNFR-ligand antibodies (FIG. 23 D).

Example 14: Receptor Activation Properties of Proteins Expressed Upon Electroporation of IVT-RNA Encoding TNFL(1)-TNFL(2) Fusion Constructs (Corresponding Duokines and scDuokines, Respectively)

Figure 24:
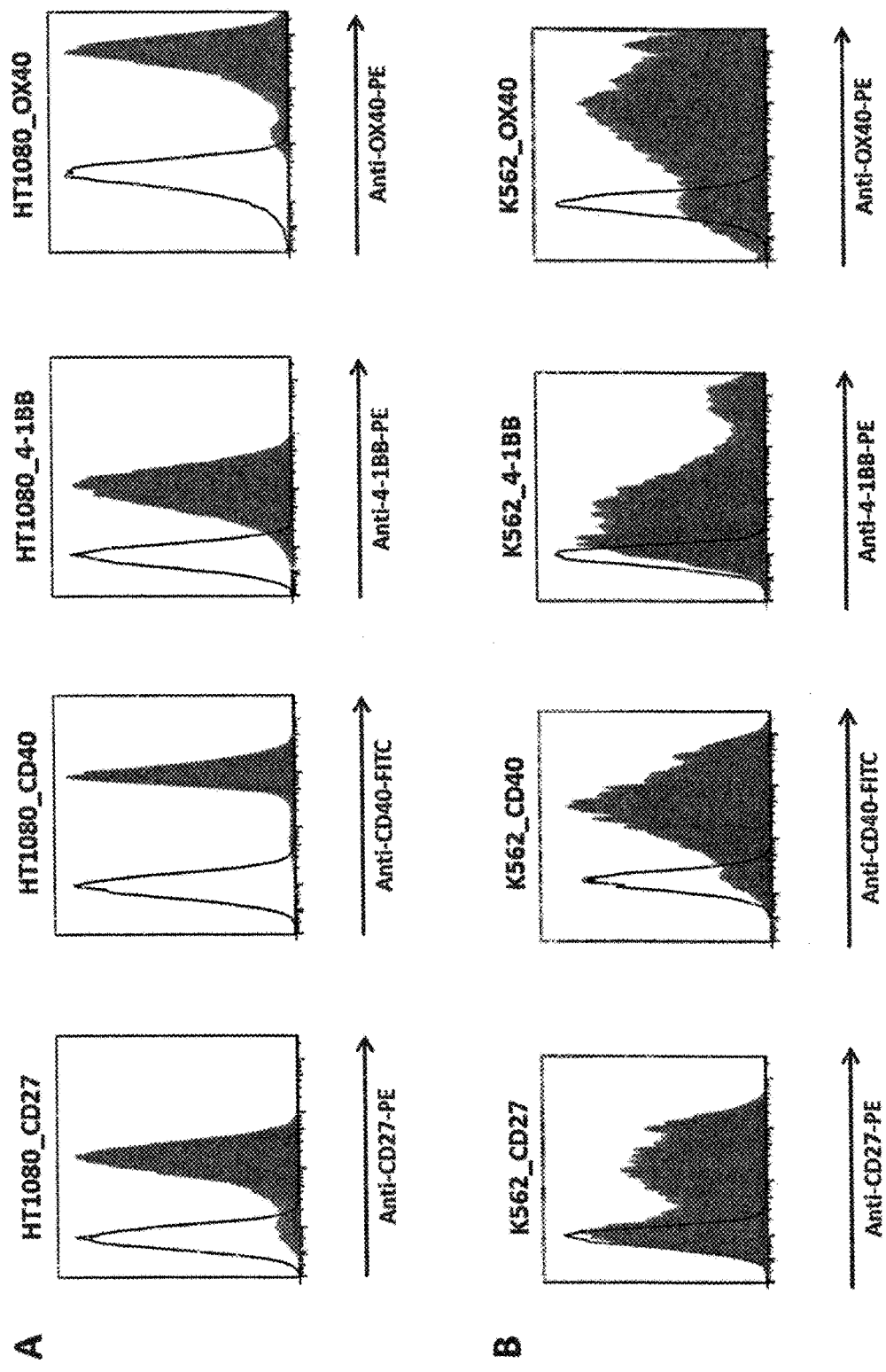
FIGS. 24 A and B. Cell surface expression of TNF receptors on stable transfectants of HT1080 and K562 after transient transfection. (A) Stable TNF-receptor transfectants of HT1080 were stained with anti-CD27-PE, anti-CD40-FITC, anti-4-1BB-PE and anti-OX40-PE. (B) K562 cells were electroporated with plasmids encoding full length coding sequence of human CD27, CD40, 4-1BB and OX40. One day after electroporation, cells were stained with anti-CD27-PE, anti-CD40-FITC, anti-4-1BB-PE and anti-OX40-PE, respectively.

Preparation of TNF receptor (TNFR) expressing cell lines/cells: a HT1080 cell line and stable TNFR transfectants thereof were cultivated in RPMI 1640 GlutaMAX® supplemented with 5% FCS, 100 IU/mL penicillin, and 100 µg/mL streptomycin. Cell surface expressions of TNF receptors on HT1080-transfectants were analyzed by FACS. To that end, cells were stained using antibodies against CD40-FITC (Biolegend), CD27-PE (BD), OX40-PE (BD) and 41BB-PE (BD) (FIG. 24 A).

In order to generate K562 transiently expressing TNF-receptors, K562 cells were washed once in X-Vivo15 medium (Lonza) and re-suspended to a final concentration of $8 \times 10^6$ cells/250 µl in X-Vivo15 again. $8 \times 10^6$ K562 cells were electroporated in 250 µl medium with 20-40 µg of plasmid DNA encoding the full length TNF receptor of human CD40, CD27, OX40 or 4-1BB. Electroporation was performed in 250 µl X-VIVO 15 in a 4 mm electroporation cuvette using the BTX ECM® 830 Electroporation System (BTX, Holliston, Mass., USA) device (200 V, 3×8 ms pulse). Immediately after electroporation, cells were transferred into a new culture plate containing fresh medium without antibiotics. On the next day, cell surface expressions of TNF receptors were checked by FACS analysis (FIG. 24 B).

Generation of supernatants containing TNFR-ligand fusion proteins: K562 multi-electroporation was performed as described above. Immediately after electroporation, cells were transferred into a new culture plate by adding 100 µl of fresh medium and rested for about 3 hours in the incubator. Then, cells were centrifuged and cell pellets were re-suspended in 250 µl RPMI 1640 GlutaMAX® with 0.5% FCS for overnight incubation (about 16 hours). On the next day, 100 µl of supernatants containing the secreted fusion proteins were transferred to confluent layers of HT1080-TNF-receptor transfectants.

NF-kappaB pathway activation upon TNF-receptor activation measured by IL-8 release of HT1080 cells: TNF-receptor transfectants of HT1080 cell line were used for reporter assays in order to measure TNF-receptor activation. Following stable transfectants expressing the human TNF receptors were used: HT1080_CD40, HT1080_CD27, HT1080_OX40 and HT1080_4-1BB; cell surface expression prior to reporter assay was checked by FACS analysis (FIG. 24 A). Cells were seeded ($2 \times 10^4$ cells/well) in 96-well tissue culture plates in RPMI 1640 medium with 5% FCS and grown overnight. Medium was extracted and 100 µl of cell culture supernatants from electroporated K562 were added. If desired, K562 expressing TNF receptors as indicated were additionally added in 100 µl RPMI 1640 GlutaMAX® medium with 0.5% FCS. After 6-8 hours of incubation, cell-free supernatants were collected and IL8-concentrations were measured by an IL-8 ELISA kit (Biolegend) according to the manufacturer's protocol.

Activation of CD40 receptor on HT1080_CD40 was detected upon electroporation of h3_CD40L and h3_CD27L-h3_CD40L. However, upon application of h3_CD27L-h3_CD40L, a strong increase of CD40 activation relating to the applied RNA amount was detected under trans-presentation settings, which was achieved by addition of K562-CD27 thus enabling a cell-cell-interaction mediated by the translated Duokine (FIG. 25 A). CD27-activation upon electroporation of IVT-RNAs encoding h3_CD27L or h3_CD27L-h3_CD40L without trans-presentation settings was not detected by measuring IL-8 secretion. Under trans-presentation settings mediated by K562_CD40, CD27-activation was detected upon K562-electroporation of the h3_CD27L-h3_CD40L fusion construct (FIG. 25 B).

h3_OX40L and h3_CD27L-h3_OX40L constructs mediated activation of the OX40 receptor. Again, upon application of h3_CD27L-h3_OX40L a clear increase of OX40 activation relating to the applied RNA amount was detected under trans-presentation settings mediated by K562_CD27 (FIG. 25 C). CD27 activation by h3_CD27L-h3_OX40L was only detectable under trans-presentation settings mediated by K562_OX40 (FIG. 25 D).

41BB- and CD27-activation upon application of h3_CD27L-h3_4-1BBL were both clearly detectable only under trans-presentation settings mediated by K562_CD27 and K562_4-1BB, respectively (FIG. 25 EF).

h3_4-1BBL-h3_CD40L and h1_4-1BBL-h1_CD40L constructs mediated activation of the CD40 receptor even without trans-presentation. However, a strong increase of CD40 activation relating to the applied RNA amount was detected under trans-presentation settings mediated by K5624-1BB (FIG. 25 G). Activation of 41BB upon application of h3_4-1BBL-h3_CD40L and of h1_4-1BBL-h1_CD40L was clearly detectable only under trans-presentation settings mediated by K562_CD40 (FIG. 25 H).

Example 15: Effects of Duokines and mRNA-Encoded scDuokines on Antigen-Specific CD8⁺ T Cell Proliferation HLA-A2' peripheral blood mononuclear cells (PBMCs) were obtained from blood donations from the Transfusionszentrale at the University Hospital in Mainz, Germany. Monocytes were isolated from PBMC by magnetic-activated cell sorting (MACS) technology using anti-CD14 MicroBeads (Miltenyi); the peripheral blood lymphocytes (PBLs, CD14⁻ fraction) were frozen for future T cell-isolation. For differentiation into immature DC (iDC), monocytes were cultured for 4-5 days in RPMI Gluta-MAX® containing 5% Human AB-Serum (Gibco), sodium pyruvate (Gibco), non-essential amino acids, 100 IU/mL penicillin, and 100 µg/mL streptomycin, 1000 IU/mL granulocyte-macrophage colony-stimulating factor and 1000

IU/mL IL-4 (both from Miltenyi). Half of the medium was replaced with fresh medium once during these 4-5 days. iDCs were harvested and washed once in X-Vivo15 medium prior to electroporation and resuspended to 300.000-500.000 cells/150 µl in X-Vivo15 again. 150 µl of cell suspension were pipetted into the 96-well plate for multi-well-electroporation, the plate already containing the required IVT-RNAs, namely RNA encoding the antigen claudin-6 plus RNAs encoding the TNFR-ligand-fusion protein as indicated or irrelevant RNA (encoding luciferase) for control, respectively. After mixing the cell suspension with RNA, electroporation was performed in the multi-well electroporation device (300 V, 1×12 ms pulse.) Immediately after electroporation, cells were transferred into a new culture plate by adding 100 µl of IMDM medium supplemented with 5% human AB serum and rested for about 1-3 hours in the incubator.

CD8$^+$ T cells were separated by MACS technology using anti-CD8 MicroBeads (Miltenyi) from remaining HLA-A2$^+$ peripheral blood lymphocytes, which were frozen after CD14$^+$-MACS-Isolation. CD8$^+$ T cells were washed once in X-vivo15 medium and resuspended to a final concentration of 10×10$^6$ cells/250 µl in X-Vivo15 again. 10×10$^6$ CD8$^+$ T cells were electroporated in 250 µl medium with 10 µg of IVT-RNA encoding the alpha-chain plus 10 µg of IVT-RNA encoding the beta-chain of a claudin-6-TCR (restricted to HLA-A2). As control, RNAs encoding a TPTE-TCR (restricted to HLA-A2$^+$) were used. Electroporation was performed in 250 µl X-Vivo15 in a 4 mm electroporation cuvette using the BTX ECM® 830 Electroporation System device (500 V, 1×3 ms pulse). Immediately after electroporation, cells were transferred into fresh IMDM medium supplemented with 5% human AB serum and rested for at least 1 hour in the incubator. Then, T cells were stained with carboxyfluorescein succinimidyl ester (CFSE) according to the manufacturer's protocol (Invitrogen).

In order to analyze effects mediated by TNFR-ligand constructs (IVT-RNA) a CFSE-proliferation assay was performed. To that end, a total of 5.000 electroporated DCs were added into a well of a 96-well plate already containing 50.000 T cells, which had been electroporated with RNA encoding CLD6-TCR or TPTE-TCR, respectively. Incubation was carried out in RPMI 1640 GlutaMAX® supplemented with 5% human AB serum 100 IU/mL penicillin, and 100 mg/mL streptomycin. PBMC proliferation was measured after 5 days of incubation by flow cytometry and analyzed by the FLOWJO® software.

Figure 26A:
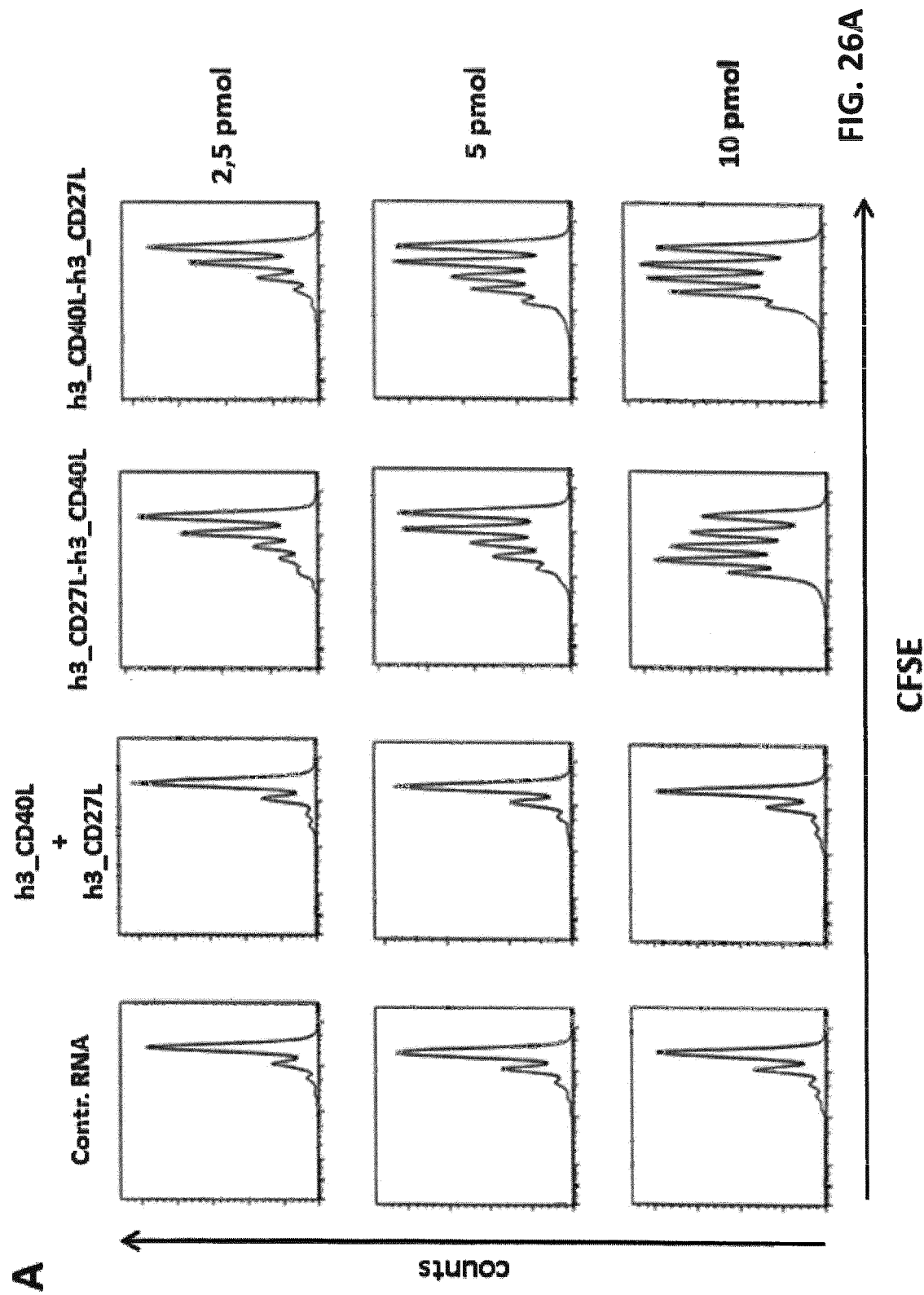
FIGS. 26 A-C. Effects of h3_CD27L-h3_CD40L and h3_CD40L-h3_CD27L fusion constructs on CD8$^+$ T cell proliferation. iDCs were electroporated with claudin-6 IVT-RNA+IVT-RNA encoding h3_CD27L-h3_CD40L, h3_CD40L-h3_CD27L and single constructs h3_CD27L+ h3_CD40L, or control RNA, respectively. CD8+ T cells (HLA-A2$^+$ donor) were electroporated with IVT-RNA encoding for a claudin-6-specific CD8$^+$ T cell receptor or encoding for a TPTE-specific CD8$^+$ T cell receptor and afterwards stained with CFSE. Electroporated iDCs and CD8$^+$ T cells were co-cultured in a ratio of 1:10 for 5 days before proliferation of CD8$^+$ T cells was analyzed by FACS. Representative histogram plots of CFSE-analysis for claudin-6-TCR$^+$ CD8$^+$ T cells are shown in (A) and for TPTE-TCR CD8$^+$ T cells are shown in (B). Detailed analysis of proliferation based on peaks indicating cell divisions was made by the FLOWJO® software. By this means percentages of T cells that went into division, indicated by "% Divided cells", and average number of divisions of cells, which went into division, indicated by "proliferation index", was calculated, both shown in (C). Application of both h3_CD27L-h3_CD40L and h3_CD40L-h3_CD27L fusion constructs resulted in increased proliferation of CD8$^+$ T cells in an antigen-specific manner, while application of two RNAs coding for the two corresponding TNFR ligands had no effect on proliferation.
Figure 26B:
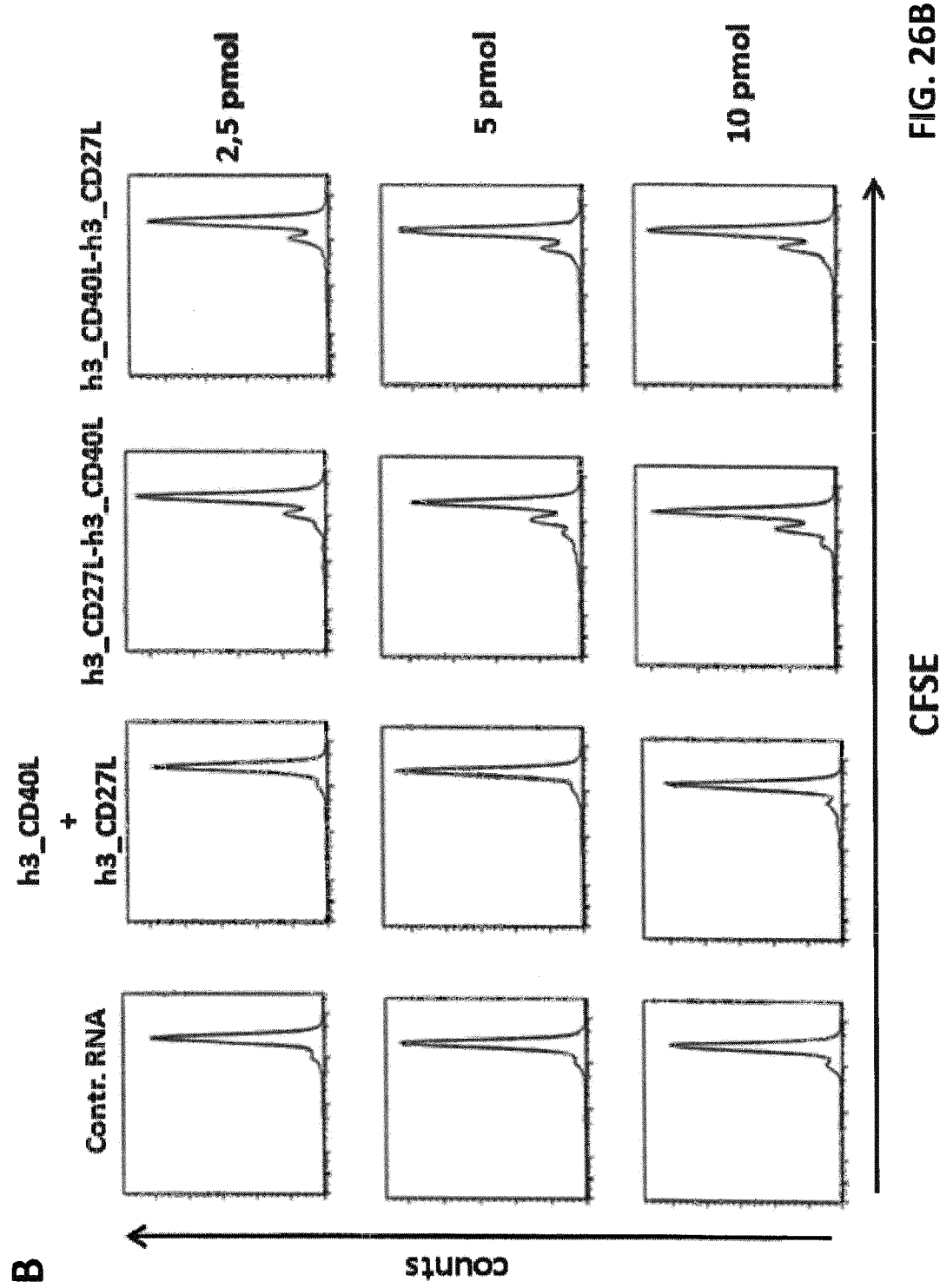
Figure 26C:
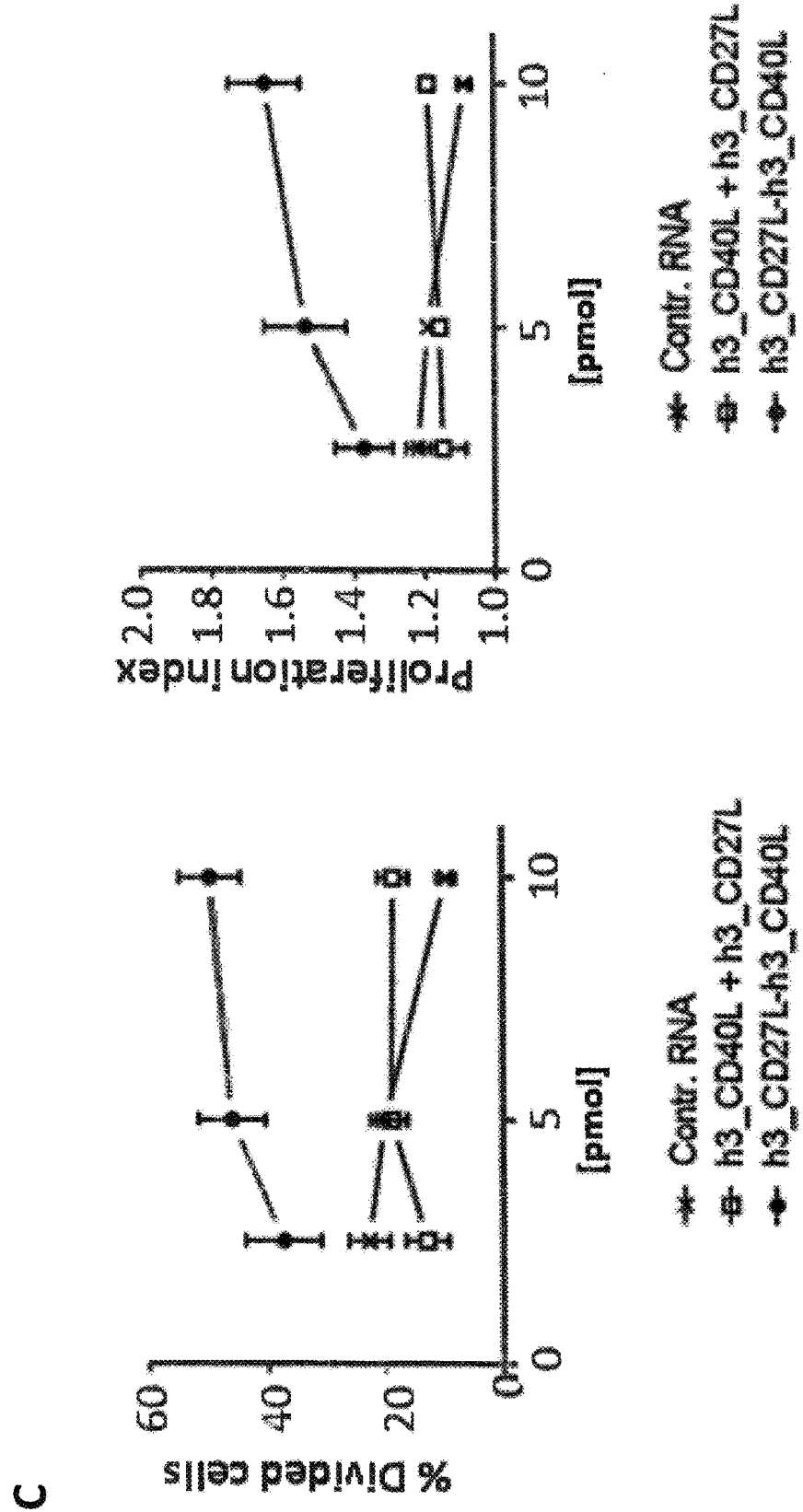

DC co-electroporation with claudin-6 antigen-RNA and h3_CD27L-h3_CD40L RNA or h3_CD40L-h3_CD27L RNA resulted in increased proliferation of CD8$^+$-T cells, more particularly, more T cells went into division (increased "% of divided cells") and then also divided more often (increased "proliferation index") (FIG. 26 A-C). By contrast, co-electroporation with claudin-6 antigen-RNA and single constructs encoding the two separate proteins h3_CD40L and h3_CD27L did not result in an increased T cell proliferation (FIG. 26 A). Additionally, h3_CD27L-h3_CD40L did not induce a considerable proliferation of control T cells, TPTE-TCR$^+$ CD8$^+$ T cells, showing that the constructs do not activate T cell proliferation in an antigen-unspecific manner (FIG. 26 B). h3_CD27L-h3_CD40L and h3_CD40L-h3_CD27L mediated comparable effects (FIG. 26 A). h3_CD27L-h3_CD40L is an example for a fusion protein, which on the one side is able to bind to and activate CD40 expressed on DCs and on the other side is able to bind to and activate CD27 constitutively expressed on T cells, thereby cross-linking these cells in trans.

Figure 27A:
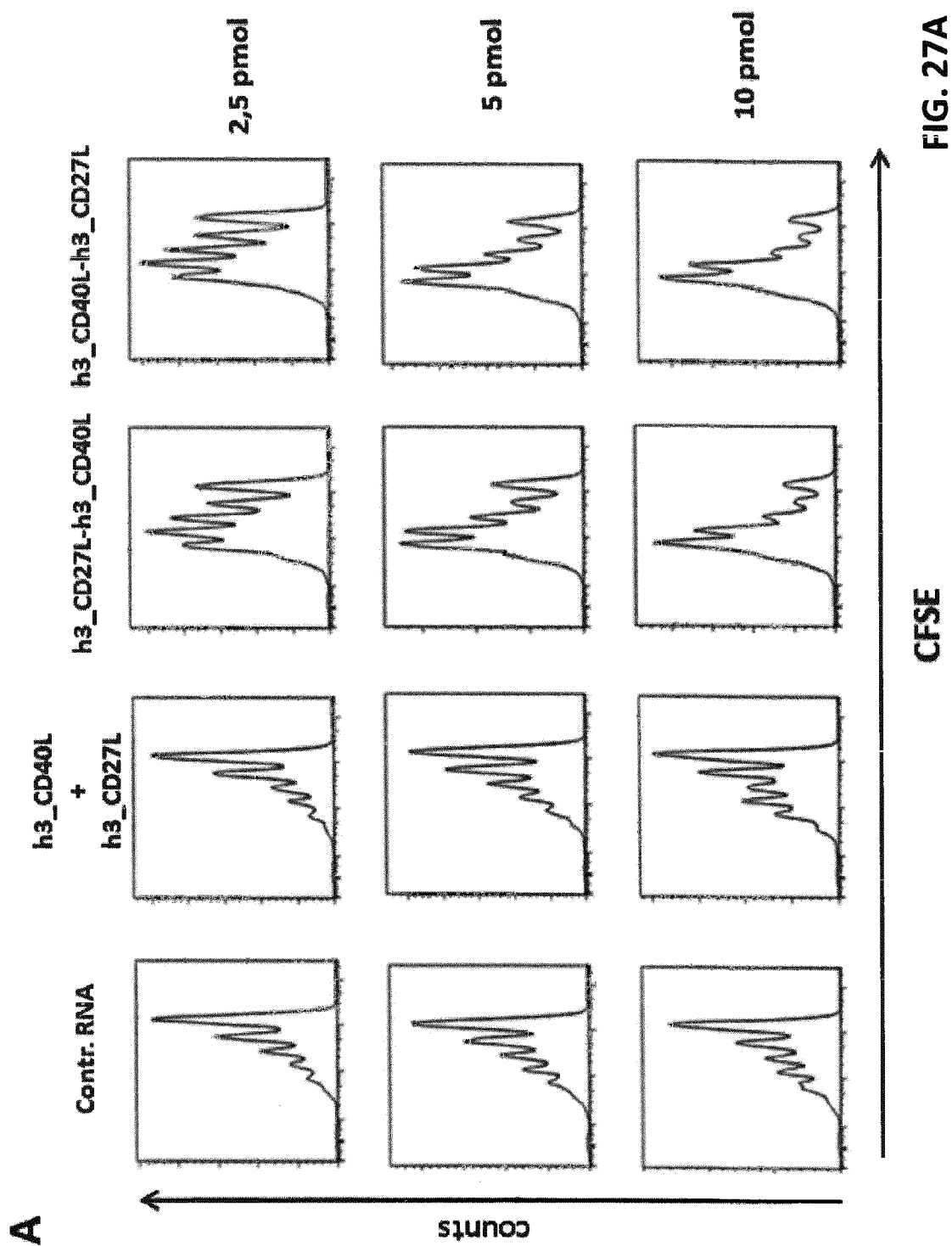
FIGS. 27 A, B, and C. Effects of h3_4-1BBL-h3_CD27L and h1_4-1BBL-h1_CD27L fusion constructs on CD8$^+$ T cell proliferation. iDCs were electroporated with claudin-6 IVT-RNA+IVT-RNA encoding h3_4-1BBL-h3_CD27L, h1_4-1BBL-h1_CD27L and single constructs h3_CD27L+ h3_4-1BBL, or control RNA, respectively. CD8+ T cells (HLA-A2$^+$ donor) were electroporated with IVT-RNA encoding for a claudin-6-specific CD8$^+$ T cell receptor or encoding for a TPTE-specific CD8$^+$ T cell receptor and afterwards stained with CFSE. Electroporated iDCs and CD8$^+$ T cells were co-cultured in a ratio of 1:10 for 5 days before proliferation of CD8$^+$ T cells was analyzed by FACS. Representative histogram plots of CFSE-analysis for claudin-6-TCR$^+$ CD8$^+$ T cells are shown in (A) and for TPTE-TCR$^+$ CD8$^+$ T cells are shown in (B). Detailed analysis of proliferation based on peaks indicating cell divisions was made by the FlowJo software. By this means percentages of T cells that went into division, indicated by "% Divided cells", and average number of divisions of cells, which went into division, indicated by "proliferation index", was calculated, both shown in (C). Application of both h3_4-1BBL-h3_CD27L and h1_4-1BBL-h1_CD27L fusion constructs resulted in increased proliferation of CD8$^+$ T cells in an antigen-specific manner, while application of two RNAs coding for the two corresponding TNFR ligands had no effect on proliferation.
Figure 27B:
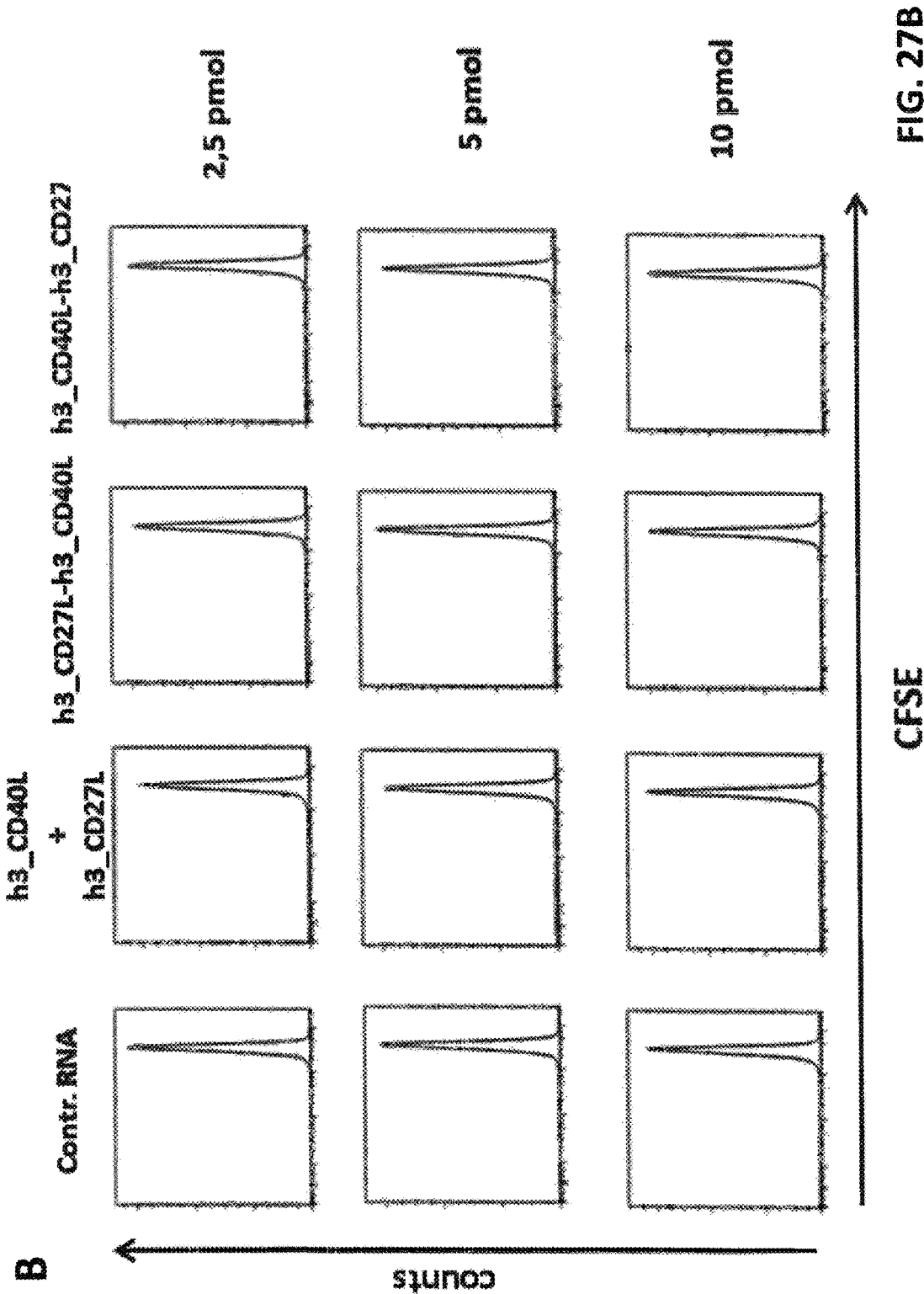
Figure 27C:
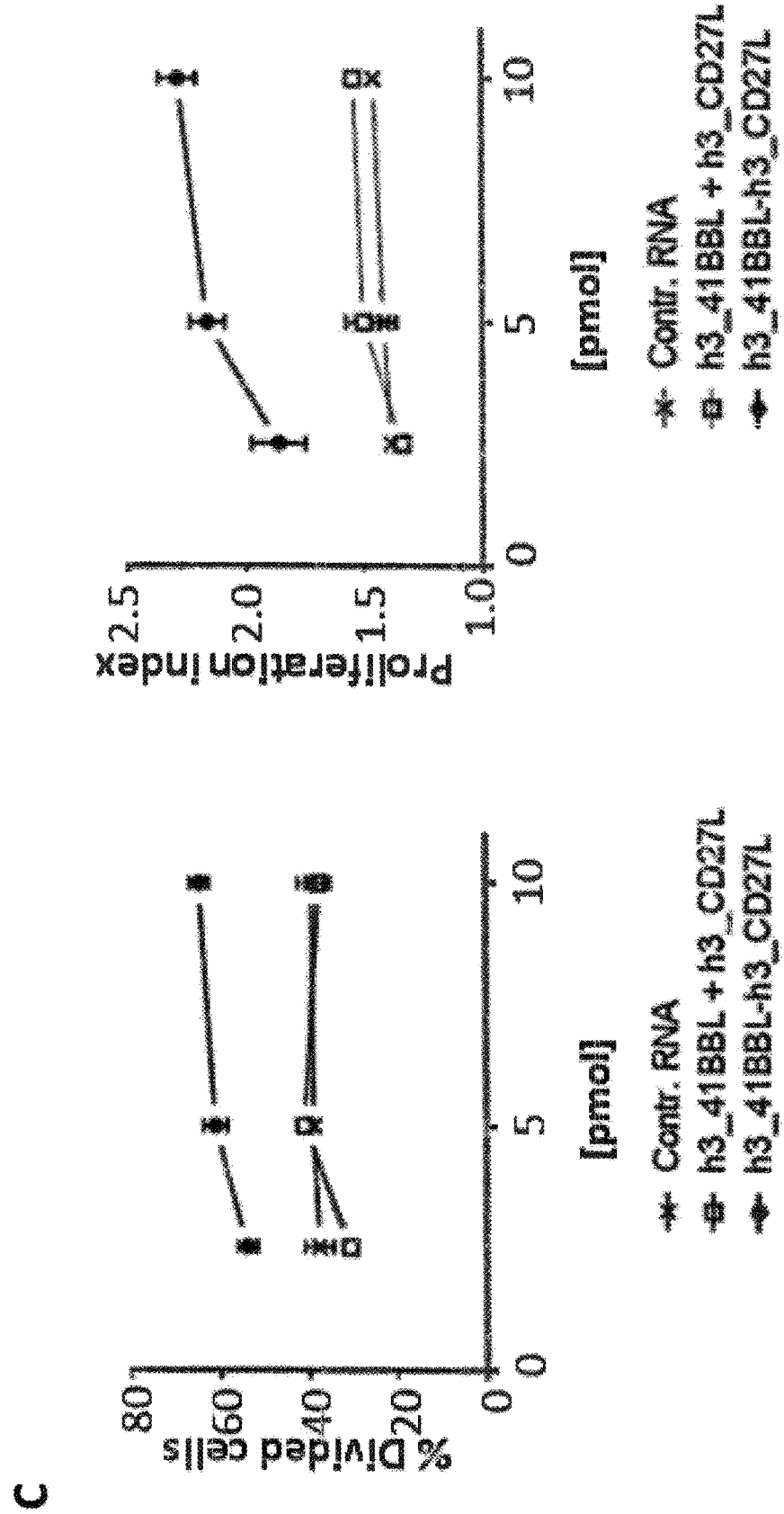

In the same way, DC co-electroporation with antigen-RNA and h3_4-1BBL-h3_CD27L RNA resulted in increased proliferation of CD8$^+$-T cells, while co-electroporation with antigen-RNA and single constructs encoding the two separate proteins h3_4-1BBL and h3_CD27L did not result in an increased T cell proliferation (FIG. 27 A). Additionally, h3_4-1BBL-h3_CD27L did not induce a proliferation of control T cells, TPTE-TCR$^+$ CD8$^+$ T cells showing that the constructs do not activate T cell proliferation in an antigen-unspecific manner (FIG. 27 B).

h3_4-1BBL-h3_CD27L (corresponding scDuokine) and h1_4-1BBL-h1_CD27L (corresponding Duokine) mediated comparable effects (FIG. 27 A). h3_4-1BBL-h3_CD27L is an example for a fusion protein, which is able to bind to and activate CD27 constitutively expressed on T cells and bind to and activate 4-1BB expressed on T cells upon activation, thereby possibly cross-linking the receptors in cis.

In order to analyze effects of recombinant Duokines, co-culture of iDCs and T cells was started one day after electroporation with the cell counts and ratios as described above. At the same time, recombinant proteins were added as indicated. PBMC proliferation was then measured after 4 days of incubation.

Figure 28:
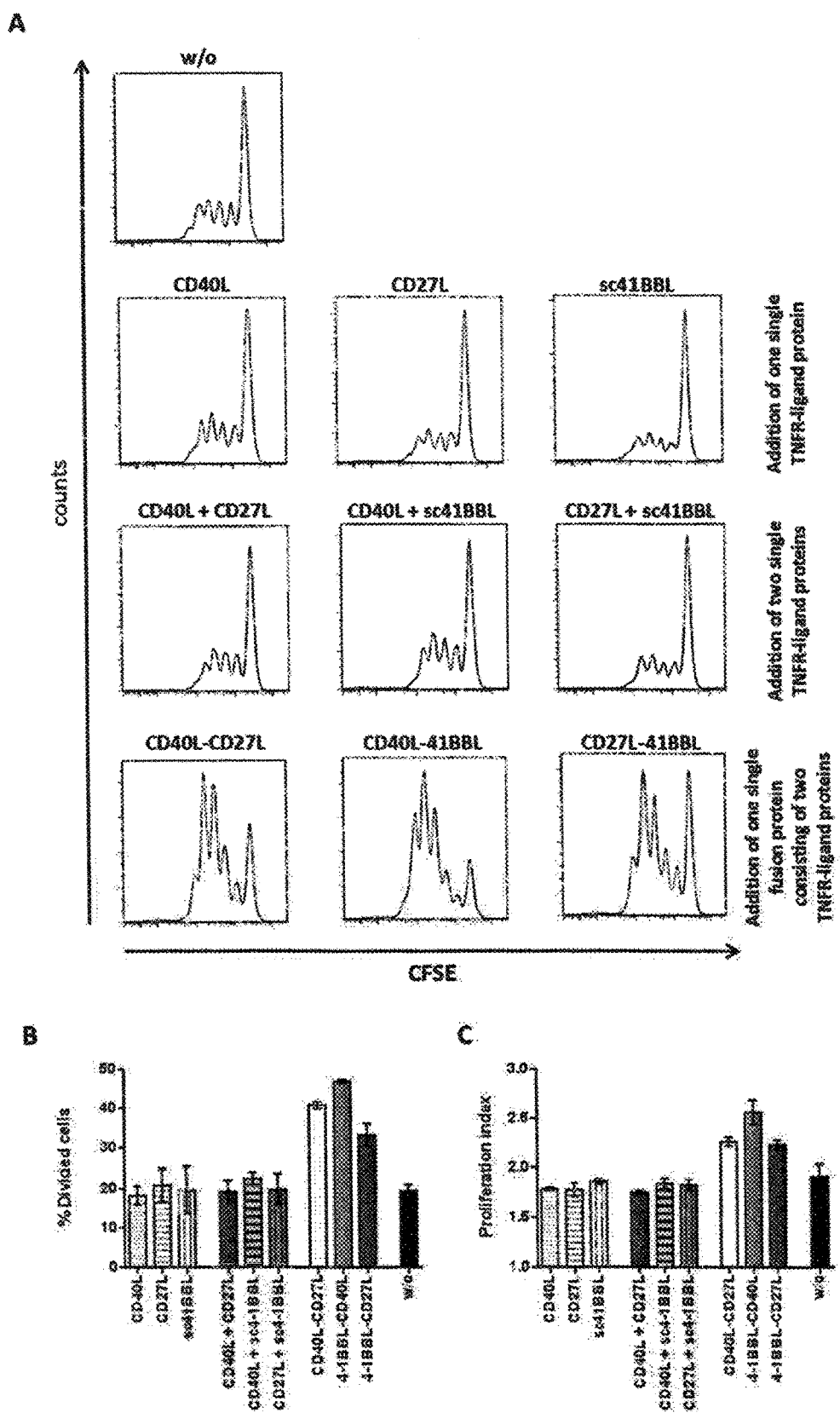
FIG. 28. Effects of recombinant Duokines on CD8$^+$ T cell proliferation. iDCs were electroporated with claudin-6 IVT-RNA. CD8$^+$ T cells (HLA-A2$^+$ donor) were electroporated with IVT-RNA encoding for a claudin-6-specific CD8$^+$ T cell receptor and afterwards stained with CFSE. One day after electroporation, iDCs and CD8$^+$ T cells were co-cultured in a ratio of 1:10 for 4 days; 10 nM of the indicated recombinant proteins each were added to the co-cultures. CD8$^+$ T cell proliferation was analyzed by FACS. Representative histogram plots of CFSE-analysis for claudin-6-TCR$^+$ CD8$^+$ T cells are shown in (A). Detailed analysis of proliferation based on peaks indicating cell divisions was made by the FLOWJO® software. By this means percentages of T cells that went into division, indicated by "% Divided cells", and average number of divisions of cells, which went into division, indicated by "proliferation index", was calculated, both shown in (B) and (C), respectively. Addition of all three Duokines resulted in increased proliferation of CD8$^+$ T cells in an antigen-specific manner, while addition of the two corresponding single TNFR ligands had no effects on proliferation.
Figure 29A:
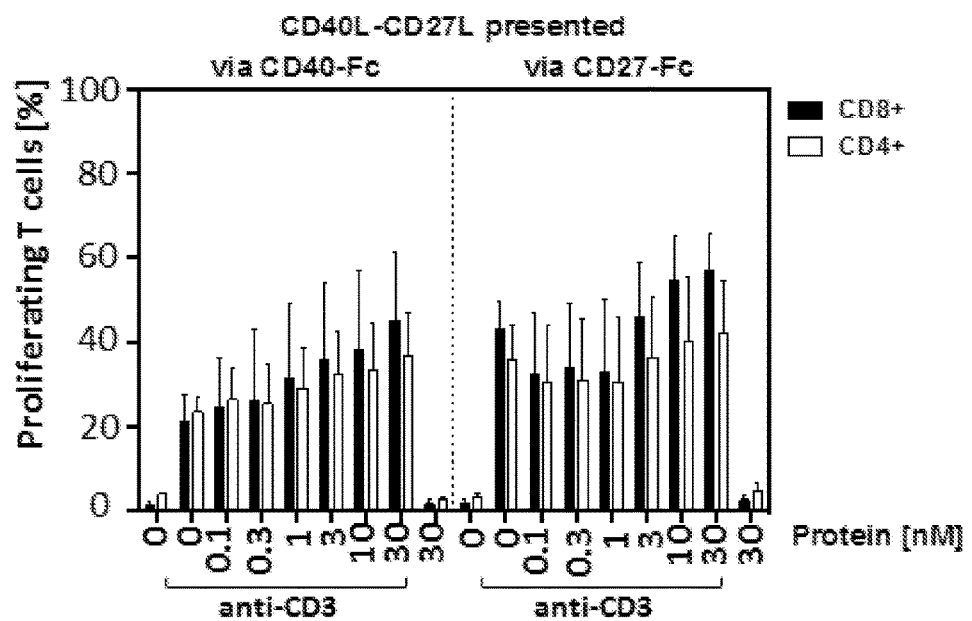
FIGS. 29A-E. Simultaneous binding of duokines to immobilized receptor and PBMCs leading to activation and proliferation of T cells. 200 ng/well receptor-Fc were immobilized on microtiter plates overnight at 4° C. Residual binding sites were blocked with RPMI 1640+10% FCS for 1 h. Serial dilutions of duokines were incubated with the immobilized receptors for 1 h, and subsequently unbound proteins were washed away. 1.5×10$^5$ CFSE-stained human PBMCs (bulk population) were added to the microtiter plate in presence (or absence) of cross-linked anti-human CD3 antibody as primary suboptimal stimulus. After 6 days, proliferation of CD4$^+$ and CD8$^+$ T cells was assessed in flow cytometry by CFSE-dilution.
Figure 29B:
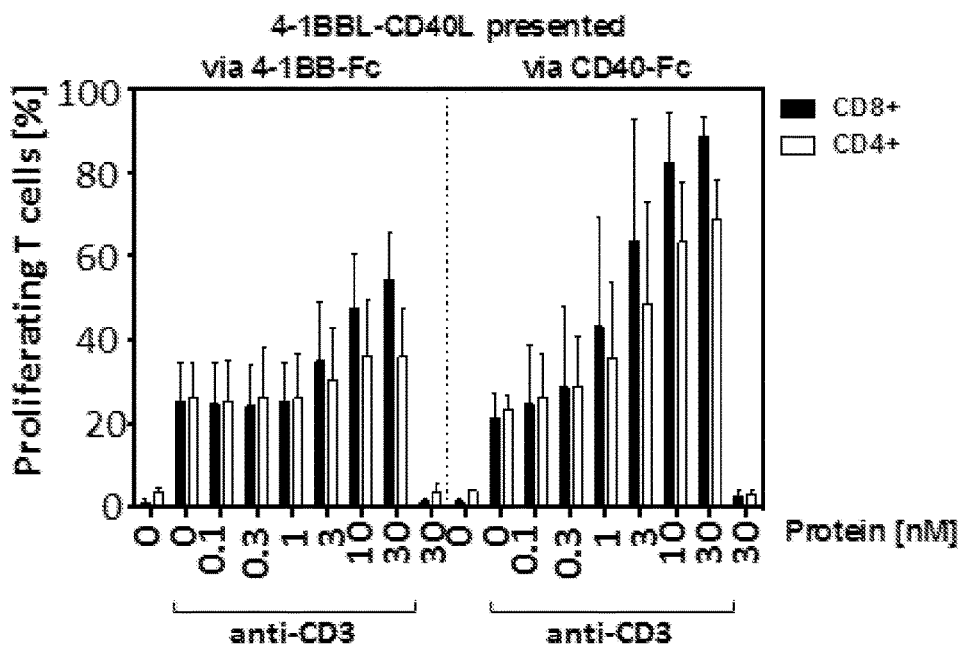
Figure 29C:
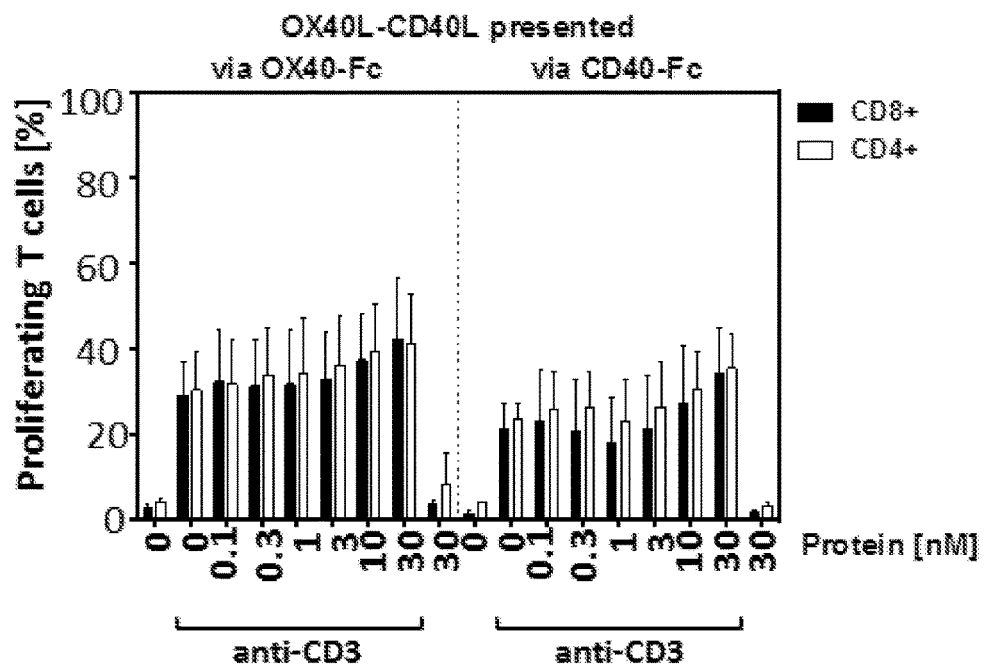
Figure 29D:
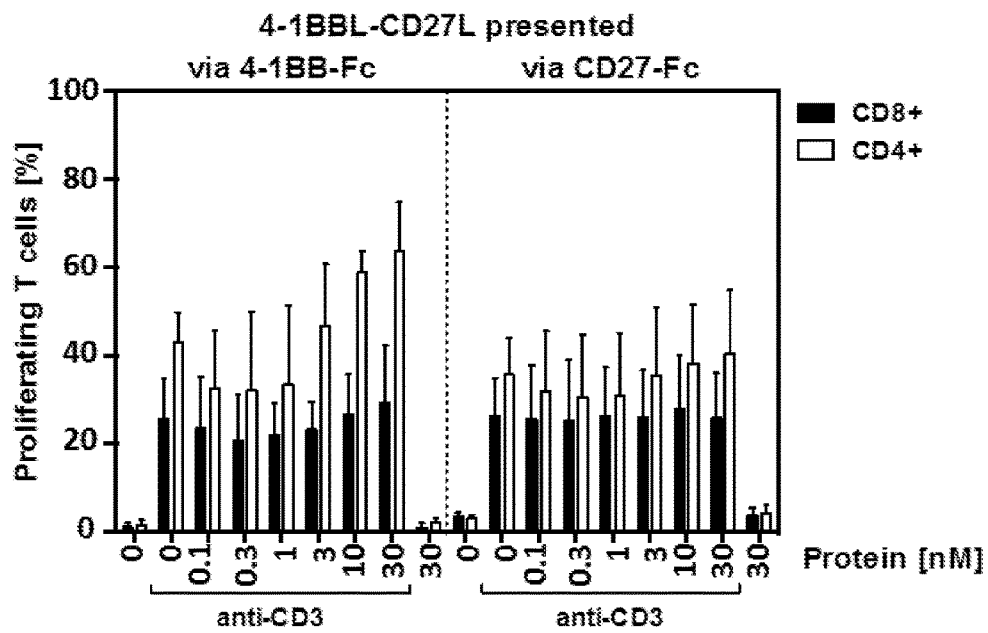
Figure 29E:
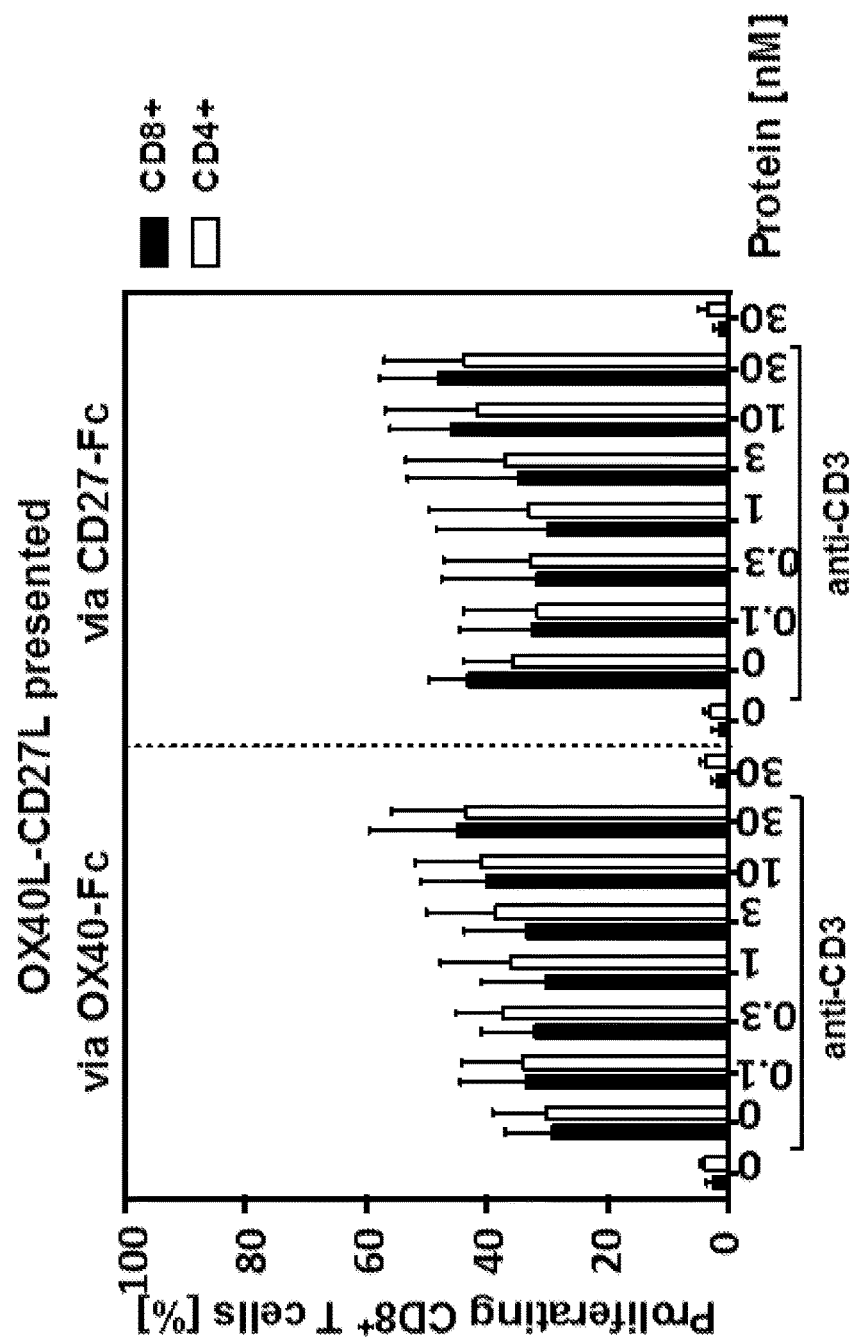

Addition of recombinant fusion proteins CD40L-CD27L, 41BBL-CD40L and 4-1BBL-CD27L to the T cell:DC co-cultures resulted in increased proliferation of CD8$^+$-T cells (FIG. 28 A). More T cells went into division (increased "% of divided cells") and then also divided more often (increased "proliferation index") (FIG. 28 B). By contrast, addition of two TNFR ligand proteins separately did not result in an increased T cell proliferation.

Example 16: Simultaneous Binding of Duokines to Immobilized Receptor and PBMCs Leading to Activation and Proliferation of T Cells It has been shown that duokines composed of 4-1BBL/CD40L, 4-1BBL/CD27L and CD40L/CD27L in solution are able to activate T cells. In a further experiment, it was analyzed if those duokines also activate T cells when they are presented through binding to a receptor immobilized on a plastic surface, restricting activation to the second receptor-binding specificity. Therefor, 200 ng/well receptor-Fc (CD40-Fc, CD27-Fc, 4-1BB-Fc, OX40-Fc) were immobilized on microtiter plates overnight at 4° C. Residual binding sites were blocked with RPMI 1640+10% FCS for 1 h. Serial dilutions of duokines (CD40L-CD27L, 4-1BBL-CD40L, 4-1BBL-CD27L, OX40L-CD40L and OX40L-CD27L) were incubated with the immobilized receptors for 1 h, and subsequently unbound proteins were washed away. Meanwhile, human PBMCs were stained at a concentration of 1×10$^6$ cells/mL with 625 nM carboxyfluorescein diacetate succinimidyl ester (CFSE) using the CellTrace® CFSE Cell Proliferation Kit (Life Technologies), following the manufacturer's instructions. For primary stimulation of T cells, anti-human CD3 monoclonal antibody (UCHT-1, R&D systems, Minneapolis, USA) was cross-linked with anti-mouse IgG at a molar ratio of 1:3. PBMCs (1.5×10$^5$ cells per well) were added together with the primary stimulus to the assay plate containing the duokines bound to the immobilized receptors. After 6 days, proliferation of T cells was determined by flow cytometry. T cells were identified by antibody staining with CD3-PE, CD4-VioBlue and CD8-PE-Vio770. For all duokines an increased proliferation of CD4$^+$ and CD8$^+$ T cells was observed, further demonstrating that both binding sites of the duokines are functional and that they are capable of inducing costimulation of T cells together with a primary stimulus provided through CD3 (FIG. 29). No proliferation was observed in the absence of CD3 stimulus supporting the dependence of T cell activation by duokines on the primary activation.

Figure 30E:
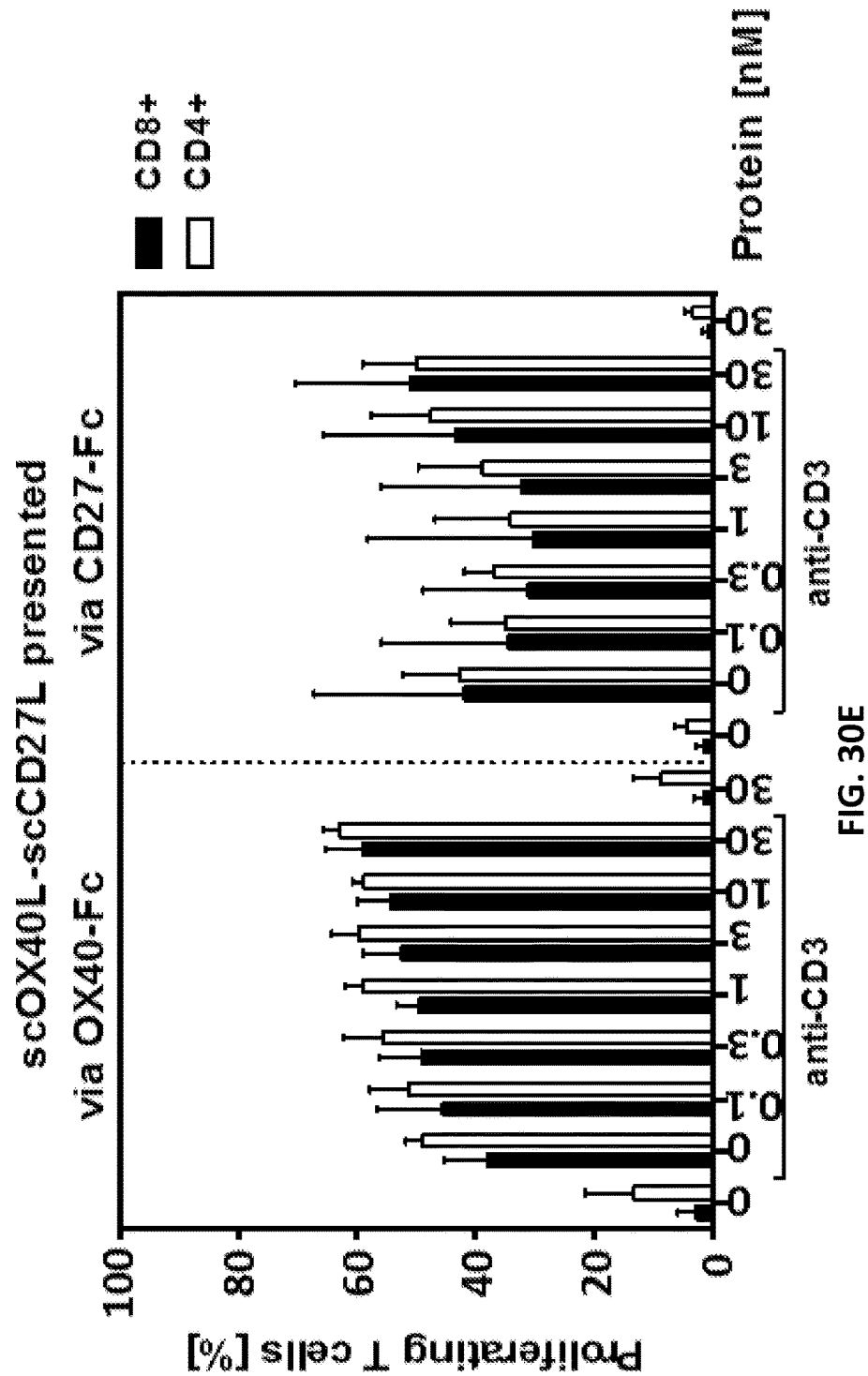

Example 17: Simultaneous Binding of Single-Chain Duokines to Immobilized Receptor and PBMCs Leading to Activation and Proliferation of T Cells It has been shown that single-chain duokines composed of 4-1BBL/CD40L, 4-1BBL/CD27L and CD40L/CD27L in solution are able to activate T cells. In a further experiment, it was analyzed if those single-chain duokines also activate T cells when they are presented through binding to a receptor immobilized on a plastic surface, restricting activation to the second receptor-binding specificity. Therefor, 200 ng/well receptor-Fc (CD40-Fc, CD27-Fc, 4-1BB-Fc, OX40-Fc) were immobilized on microtiter plates overnight at 4° C. Residual binding sites were blocked with RPMI 1640+10% FCS for 1 h. Serial dilutions of single-chain duokines (scCD40L-scCD27L, sc4-1BBL-scCD40L, sc4-1BBL-scCD27L, scOX40L-scCD40L and scOX40L-scCD27L) were incubated with the immobilized receptors for 1 h, and subsequently unbound proteins were washed away. Meanwhile, human PBMCs were stained at a concentration of $1 \times 10^6$ cells/mL with 625 nM carboxyfluorescein diacetate succinimidyl ester (CFSE) using the CellTrace® CFSE Cell Proliferation Kit (Life Technologies), following the manufacturer's instructions. For primary stimulation of T cells anti-human CD3 monoclonal antibody (UCHT-1, R&D systems, Minneapolis, USA) was crosslinked with anti-mouse IgG at a molar ratio of 1:3. $1.5 \times 10^5$ PBMC per well were added together with the primary stimulus to the assay plate containing the single-chain duokines bound to the immobilized receptors. After 6 days, proliferation of T cells was determined by flow cytometry. T cells were identified by antibody staining with CD3-PE, CD4-VioBlue and CD8-PE-Vio770. For all single-chain duokines an increased proliferation of CD4 and $CD8^+$ T cells was observed, further demonstrating that both binding sites of the single-chain duokines are functional and that they are capable of inducing costimulation of T cells together with a primary stimulus provided through CD3 (FIG. 30). No proliferation was observed in the absence of CD3 stimulus supporting the dependence of T cell activation by single-chain duokines on the primary activation.

Figure 31:
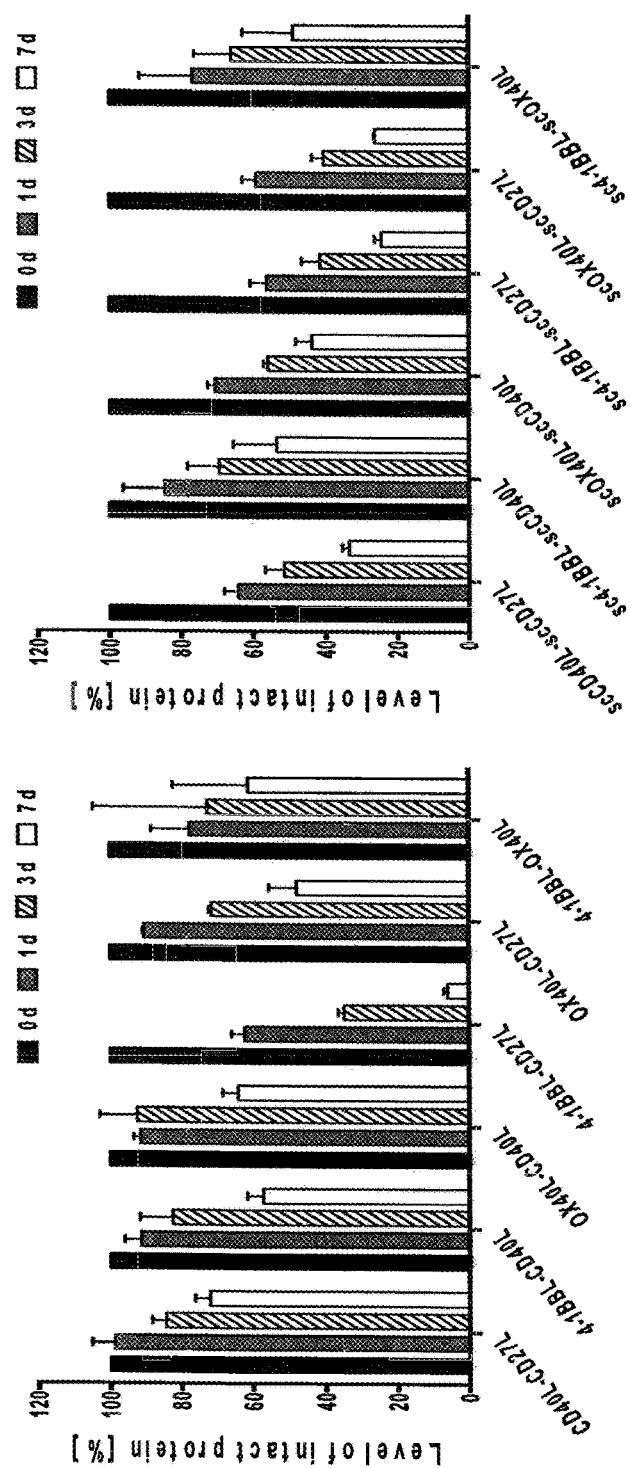
FIG. 31. Stability of selected duokines and single-chain duokines in human plasma. 200 nM (functional TNF ligand units) of the purified duokines and single-chain duokines were prepared in 50% human plasma. Samples were frozen at −20° C. immediately after preparation (0 d) or after incubating at 37° C. for 1 d, 3 d and 7 d. The level of intact protein was determined in ELISA via binding of C-terminal homotrimeric ligand units to immobilized receptor (150 ng/well) and detection of the N-terminal FLAG-tag. Protein concentrations in the diluted plasma samples were interpolated from a standard curve of purified protein. The amount of detected fusion protein on day 0 was set to 100%.

Example 18: Stability of Selected Duokines and Single-Chain Duokines in Human Plasma The stability of duokines and single-chain duokines was tested in vitro using human plasma. 200 nM of the purified duokines and single-chain duokines were prepared in 50% human plasma from healthy donors. Samples were frozen at −20° C. immediately after preparation (0 d) or after incubating at 37° C. for 1 d, 3 d and 7 d. The level of intact protein was determined using ELISA via binding of C-terminal homotrimeric ligand units to immobilized receptor (150 ng/well) and detection of the N-terminal FLAG-tag. Protein concentrations in the diluted plasma samples were interpolated from a standard curve of purified protein. The amount of detected fusion protein on day 0 was set to 100%. Six duokines and six single-chain duokines were tested, covering all possible ligand combinations, and all constructs showed a time-dependent decrease in intact protein level, as revealed by receptor binding assay. After 7 days, between 50 and 70% intact duokines were detectable in the plasma samples for most ligand combinations (FIG. 31, left side). Only in case of 4-1BBL-CD27L the amount of intact protein decreased to less than 10% after 7 days with a reduction of 40% in the first day. In general, single-chain duokines showed reduced stability with 20-50% intact protein remaining after 7 days (FIG. 31, right side).

Figure 32:
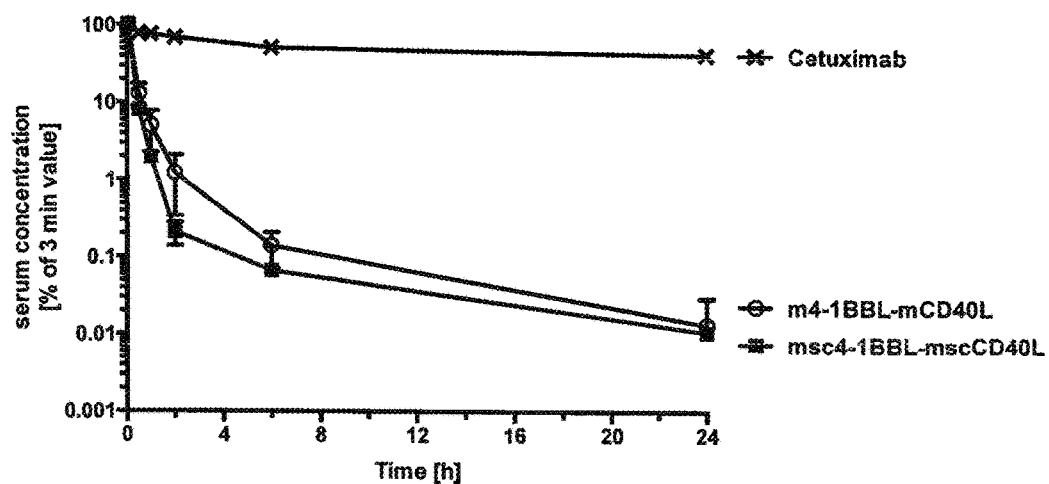
FIG. 32. Pharmacokinetic properties of a selected murine duokine and single-chain duokine in CD1 mice. 25 μg of purified protein were injected into the tail vein of female CD1 mice (12-16 weeks, 30-35 g, 3 mice per construct) in a total volume of 150 μl. Blood samples were taken 3 min, 30 min, 1 h, 2 h, 6 h, 1 d, and 3 d after injection, incubated on ice for 30 min, and centrifuged at 13,000 g for 30 min at 4° C. Serum samples were stored at −20° C. Serum levels of fusion proteins were determined in ELISA via binding to immobilized receptor (150 ng/well) corresponding to the C-terminal ligand and detecting via the N-terminal FLAG-tag. Serum concentrations of all proteins were obtained by interpolation from a standard curve of the purified protein. For comparison, the concentration at 3 min was set to 100%. Initial and terminal half-lives ($t_{1/2}\alpha_{3-6}$ mm, $t_{1/2}\beta_{1-24h}$) and AUC were calculated with Excel.

Example 19: Pharmacokinetic Properties of a Selected Murine Duokine and Murine Single-Chain Duokine in CD1 Mice In vivo bioavailability of a selected mouse-specific duokine and its corresponding single-chain duokine was studied by determining serum concentrations after a single i.v. injection. Female CD1 mice (12-16 weeks, 30-35 g, 3 mice per duokine) received one intravenous injection of 25 µg m4-1BBL-mCD40L and msc4-1BBL-mscCD40L, respectively, in a total volume of 150 µl each. Blood samples were taken from the tail vein 3 min, 30 min, 1 h, 2 h, 6 h, 1 d, and 3 d after injection, incubated on ice for 30 min, and centrifuged at 13,000 g for 30 min at 4° C. Serum was separated from cellular components and samples were stored at −20° C. Serum levels of fusion proteins were determined in ELISA via binding to immobilized receptor (150 ng/well) corresponding to the C-terminal ligand and detecting via the N-terminal FLAG-tag. Serum concentrations of all proteins were obtained by interpolation from a standard curve of the purified protein. For comparison, the concentration at 3 min was set to 100%. Initial and terminal half-lives ($t_{1/2}\alpha_{3-60min}$, $t_{1/2}\beta_{1-24h}$) were calculated with Excel. Both m4-1BBL-mCD40L and msc4-1BBL-mscCD40L showed clearance from the blood stream with terminal half-lives of 3.8 (single-chain duokine) and 5.6 h (duokine) and a short initial half-life of 10-13 min in both cases (FIG. 32). Compared to a full-length IgG (Cetuximab) utilizing FcRn-mediated recycling, both constructs were rapidly cleared. A comparison with a scFv-4-1BBL fusion protein with a terminal half-life of 6.6 h (data not shown) shows that the half-life of m4-1BBL-mCD40L and msc4-1BBL-mscCD40L is within the same range of those functionally related, immunostimulatory fusion proteins. The general rapid clearance of immunostimulatory fusion proteins including duokines points to target cell (i.e. immune cell) specific consumption.

Example 20: Receptor Expression on Human PBMC and Binding of Single-Chain Duokines to Immune Cell Subpopulations In order to determine the possible target cell populations within a PBMC population and the actual target cells of single-chain duokines, human PBMCs were characterized in detail. PBMCs from healthy donors were thawed and incubated on a cell culture dish overnight at 4° C. The next day, $2.5 \times 10^5$ human PBMC were incubated with 10 nM single-chain duokines in presence or absence of cross-linked anti-human CD3 antibody as primary stimulus at a response limiting, suboptimal concentration. After 3 days at 37° C., different subpopulations were identified in flow cytometry by CD marker staining (anti-CD3, anti-CD4, anti-CD8, anti-CD14, anti-CD20 and anti-CD56) and the binding of single-chain duokines to the different subpopulations was assessed by detecting their FLAG-tag. Furthermore, stimulated and unstimulated PBMC were also incubated without single-chain duokines, subpopulations were identified after 3 days of cultivation and the surface expression of CD40, CD27, 4-1BB and OX40 was determined by antibody staining. Unstimulated PBMC were composed of approx. 40%

Figure 33:
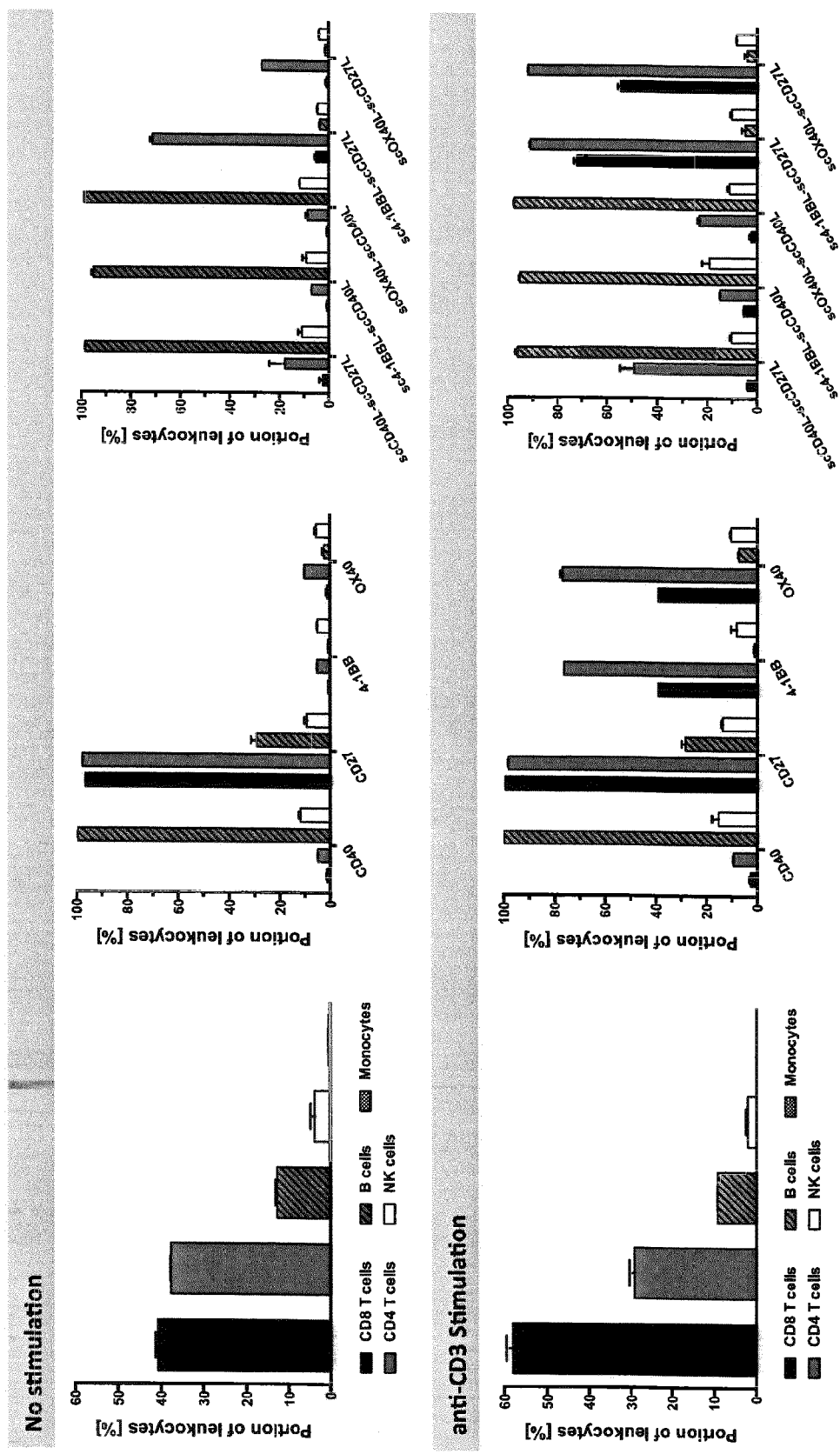
FIG. 33. Receptor expression on human PBMC and binding of single-chain duokines to immune cell subpopulations. $2.5 \times 10^5$ human PBMC (bulk population) were incubated with 10 nM single-chain duokines in presence or absence of cross-linked anti-human CD3 antibody as primary suboptimal stimulus. After 3 days at 37° C., different subpopulations were identified in flow cytometry by CD marker staining (anti-CD3, anti-CD4, anti-CD8, anti-CD14, anti-CD20 and anti-CD56) and the binding of single-chain duokines to the different subpopulations was assessed by detecting their FLAG-tag. Furthermore, stimulated and unstimulated PBMC were also incubated without single-chain duokines, subpopulations were identified after 3 days of cultivation and the surface expression of CD40, CD27, 4-1BB and OX40 was determined by antibody staining.

CD8+ T cells, 40% CD4+ T cells, 15% B cells and 5% NK cells (FIG. 33, upper left). Due to the treatment of the PBMCs, all monocytes adhered to plastic surfaces and were not present in the experiment. After 3 days stimulation with anti-CD3 mAb, the amount of CD8+ T cells increased to nearly 80% accompanied with a slight decrease in percentages of all other cell types (FIG. 33, lower left). The receptors CD40 and CD27 were constitutively expressed on B cells (CD40) and both types of T cells (CD27) independent of stimulation. While 4-1BB and OX40 were not present on any unstimulated PBMCs, around 80% stimulated CD4+ T cells and 40% stimulated CD8+ T cells expressed both receptors (FIG. 33, middle panel). Consistent with receptor expressions, the three tested trans-acting single-chain duokines (scCD40L-scCD27L, sc4-1BBL-scCD40L and scOX40L-scCD40L) bound nearly exclusively to stimulated and unstimulated B cells (FIG. 33, upper right). The cis-acting single-chain duokines (sc4-1BBL-scCD27L and scOX40L-scCD27L) bound only to a fraction of CD4+ T cells in the unstimulated setting and to a large portion of CD4+ and CD8+ T cells after stimulation (FIG. 33, lower right). In summary, these experiments show that trans-acting molecules target B cells independent from stimulation, while cis-acting constructs target activated CD8+ and CD4+ T cells.

Figure 34:
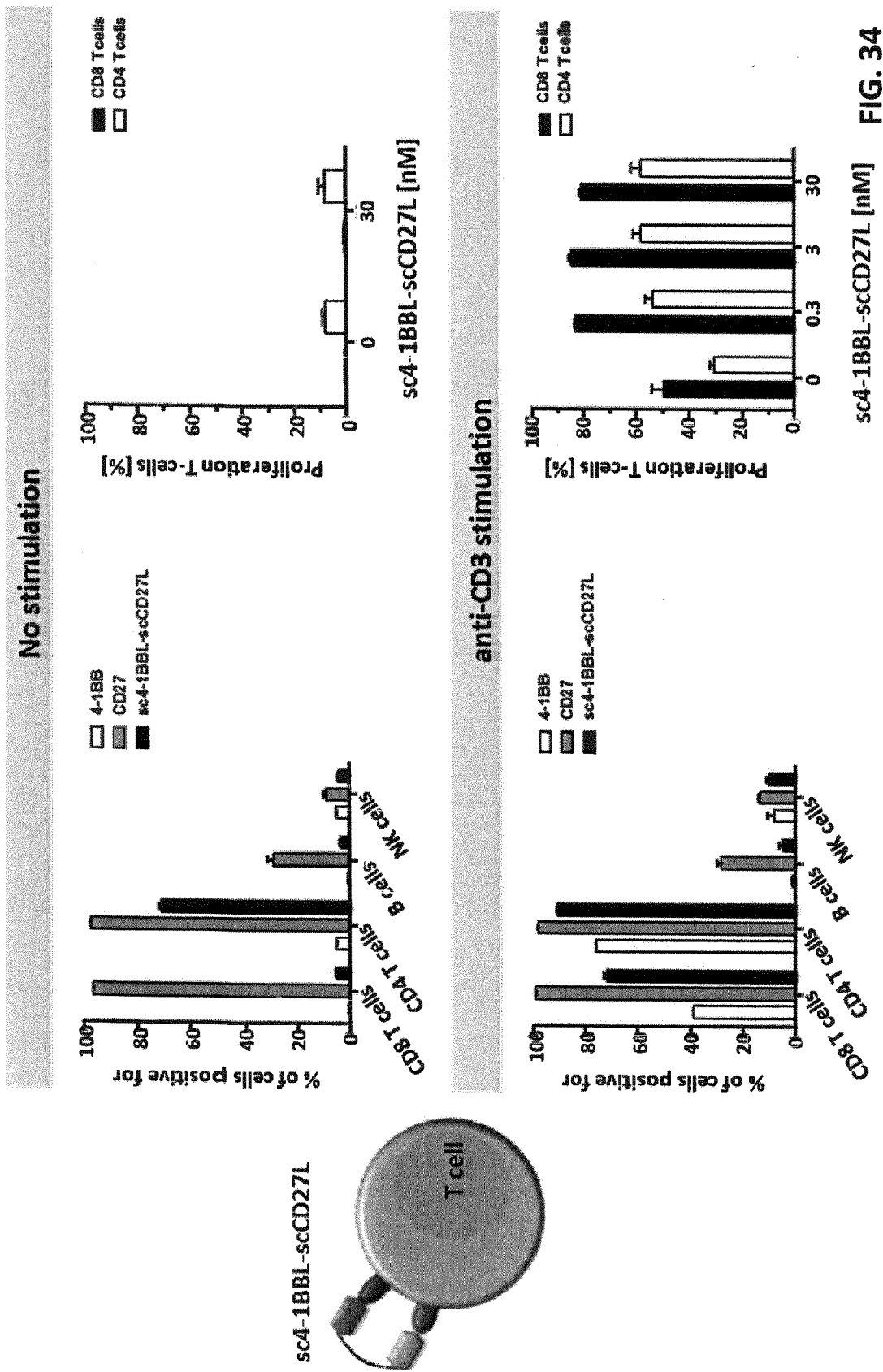
FIG. 34. Binding of a cis-acting single-chain duokine to human immune cells and induction of T cell proliferation. $2.5 \times 10^5$ human PBMC (bulk population) were incubated with 10 nM sc4-1BBL-scCD27L in presence or absence of cross-linked anti-human CD3 antibody as primary suboptimal stimulus. After 3 days at 37° C., different subpopulations were identified in flow cytometry by CD marker staining (anti-CD3, anti-CD4, anti-CD8, anti-CD20 and anti-CD56), the surface expression of CD27 and 4-1BB was determined by antibody staining, and the binding of the single-chain duokine was assessed by detecting its FLAG-tag. $1.5 \times 10^5$ CFSE-labeled PBMC (bulk population, different PBMC batch) were incubated with 30, 3, 0.3 or 0 nM sc4-1BBL-scCD27L in presence or absence of cross-linked anti-human CD3 antibody as primary suboptimal stimulus. After 6 days, proliferation of CD4 and CD8 T cells was determined in flow cytometry by CFSE-dilution.

Example 21: Binding of a Cis-Acting Single-Chain Duokine to Human Immune Cells and Induction of T Cell Proliferation The connection between binding to human immune cells and induction of T cell proliferation was examined for one selected cis-acting single-chain duokine. For this, 2.5×10$^5$ human PBMC (bulk population) were incubated with 10 nM sc4-1BBL-scCD27L in presence or absence of cross-linked anti-human CD3 antibody as primary suboptimal stimulus. After 3 days at 37° C., different subpopulations were identified in flow cytometry by CD marker staining (anti-CD3, anti-CD4, anti-CD8, anti-CD20 and anti-CD56). The surface expression of CD27 and 4-1BB was determined by antibody staining and the binding of the single-chain duokine was assessed by detecting its FLAG-tag. 1.5×10$^5$ CFSE-labeled PBMCs (bulk population, different PBMC batch) were incubated with 30, 3, 0.3 or 0 nM sc4-1BBL-scCD27L in presence or absence of cross-linked anti-human CD3 antibody as primary suboptimal stimulus. After 6 days, proliferation of CD4+ and CD8+ T cells was determined in flow cytometry by CFSE-dilution. When applied in combination with cross-linked anti-human CD3 antibody as primary stimulus, sc4-1BBL-scCD27L enhanced the initial CD3-mediated proliferation of CD4+ and CD8+ T cells by 30% already at low concentrations of 0.3 nM (FIG. 34, lower right). Generally, more CD8+ T cells (80%) than CD4+ T cells (60%) started to proliferate. This proliferation profile is in agreement with the finding that sc4-1BBL-scCD27L binds to both 4-1BB- and CD27-expressing CD4+ and CD8+ T cells in the stimulated setting (FIG. 34, lower left). Without anti-CD3 stimulation, proliferating CD8+ T cells were not observed at all and only marginal proliferation of ~10% CD4+ T cells was found (FIG. 34, upper right). This basal proliferation rate was not enhanced by sc4-1BBL-scCD27L, although binding to CD27-expressing CD4+ T cells was noted (FIG. 34, upper left), indicating that cis-acting duokines do not act on resting T cells.

Example 22: Binding of a Trans-Acting Single-Chain Duokine to Human Immune Cells and Induction of T Cell Proliferation The connection between binding to human immune cells and induction of T cell proliferation was examined for a selected trans-acting single-chain duokine. For this, 2.5×10$^5$ human PBMC (bulk population) were incubated with 10 nM sc4-1BBL-scCD40L in presence or absence of cross-linked anti-human CD3 antibody as primary suboptimal stimulus. After 3 days at 37° C., different subpopulations were identified in flow cytometry by CD marker staining (anti-CD3, anti-CD4, anti-CD8, anti-CD20 and anti-CD56). The surface expression of CD40 and 4-1BB was determined by antibody staining, and the binding of the single-chain duokine was assessed by detecting its FLAG-tag. 1.5×10$^5$ CFSE-labeled PBMC (bulk population, different PBMC batch) were incubated with 30, 3, 0.3 or 0 nM sc4-1BBL-scCD40L in presence or absence of cross-linked anti-human CD3 antibody as primary suboptimal stimulus. After 6 days, proliferation of CD4+ and CD8+ T cells was determined in flow cytometry by CFSE-dilution.

Figure 35:
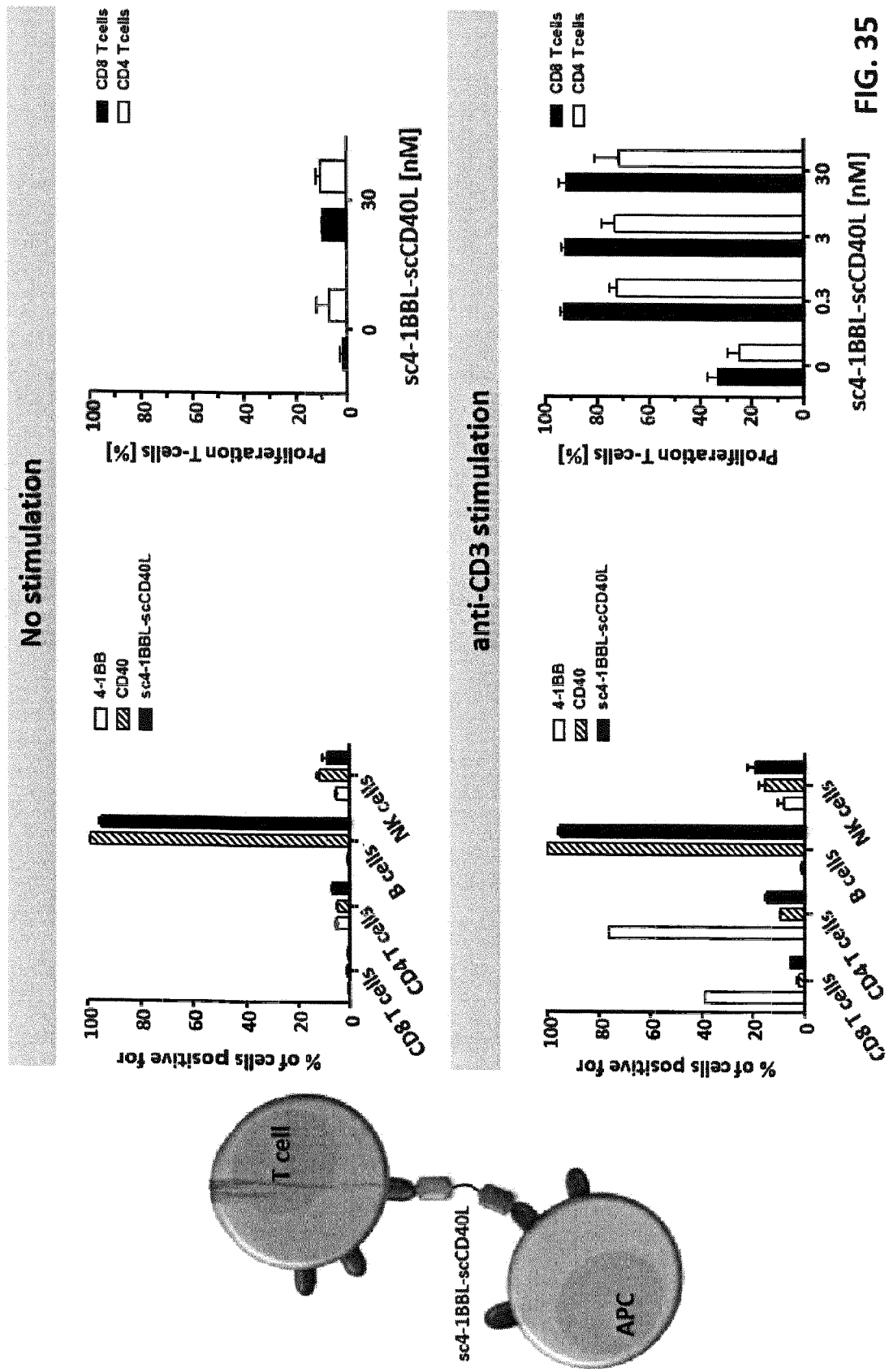
FIG. 35. Binding of a trans-acting single-chain duokine to human immune cells and induction of T cell proliferation. $2.5 \times 10^5$ human PBMC (bulk population) were incubated with 10 nM sc4-1BBL-scCD40L in presence or absence of cross-linked anti-human CD3 antibody as primary suboptimal stimulus. After 3 days at 37° C., different subpopulations were identified in flow cytometry by CD marker staining (anti-CD3, anti-CD4, anti-CD8, anti-CD20 and anti-CD56), the surface expression of CD40 and 4-1BB was determined by antibody staining and the binding of the single-chain duokine was assessed by detecting its FLAG-tag. $1.5 \times 10^5$ CFSE-labeled PBMC (bulk population, different PBMC batch) were incubated with 30, 3, 0.3 or 0 nM sc4-1BBL-scCD40L in presence or absence of cross-linked anti-human CD3 antibody as primary suboptimal stimulus. After 6 days, proliferation of CD4 and CD8 T cells was determined in flow cytometry by CFSE-dilution.

When applied in combination with cross-linked anti-human CD3 antibody as primary stimulus, sc4-1BBL-scCD40L strongly enhanced the initial CD3-mediated proliferation of CD4+ and CD8+ T cells by 50-60% already at low concentrations of 0.3 nM. Generally, nearly all CD8+ T cells (90%) and around 70% CD4+ T cells started to proliferate (FIG. 35, lower right). sc4-1BBL-scCD40L initially binds to B cells constitutively expressing CD40, enabling a trans-presentation of the 4-1BBL module of this single-chain duokine to primed 4-1BB-expressing T cells (FIG. 35, lower right). Without CD3 stimulation, only a marginal (3%) CD8+ T cell proliferation could be observed, and a slight increase to 9% proliferating cells was observed upon adding sc4-1BBL-scCD40L, indicating that a minor fraction of CD8+ T cells can respond to transactivation in the absence of intentional CD3 triggering (FIG. 35, upper panel), suggesting that these cells are in a preactivated state.

Figure 36:
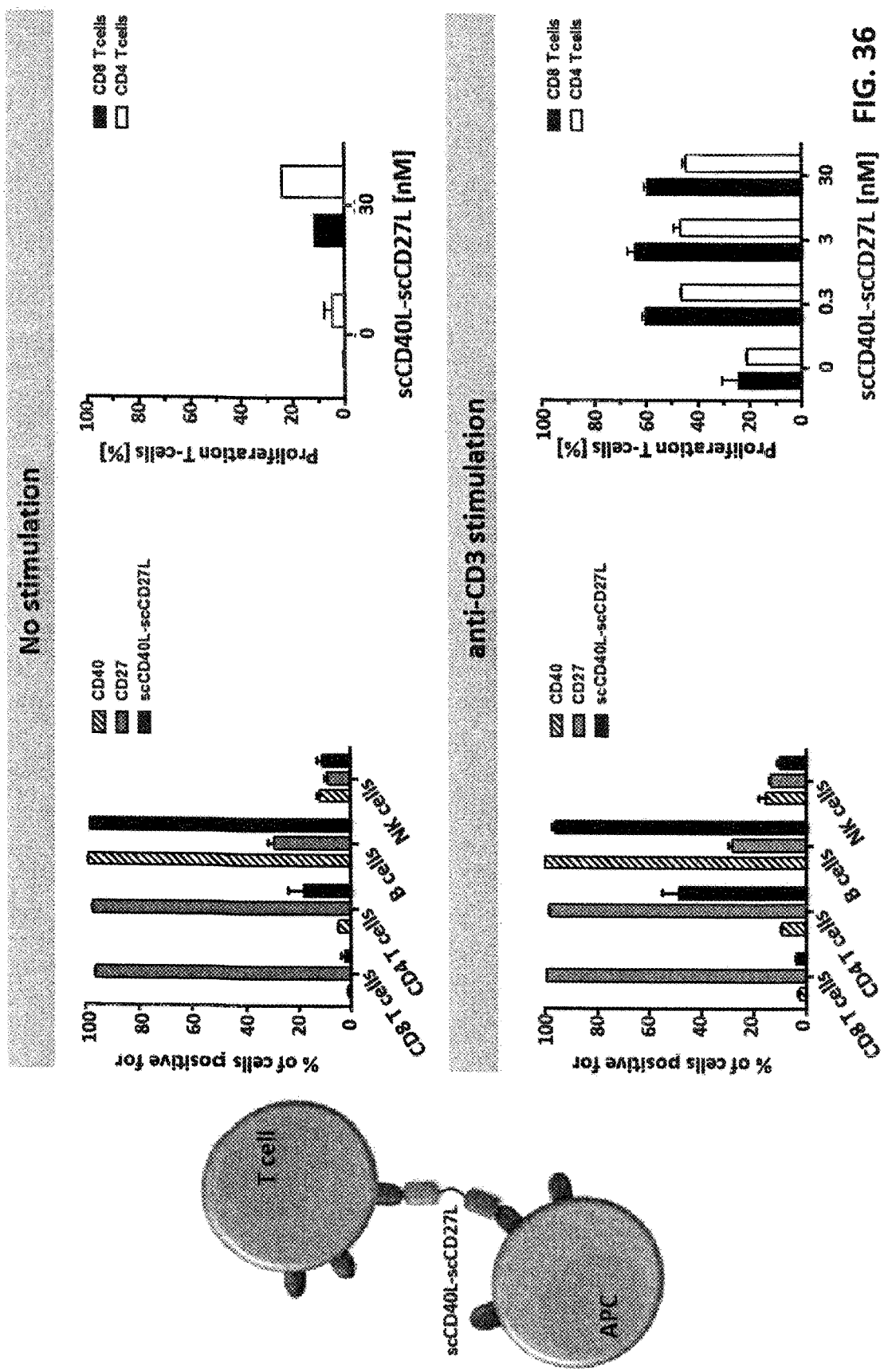
FIG. 36. Binding of a trans-acting single-chain duokine to human immune cells and induction of T cell proliferation. $2.5 \times 10^5$ human PBMC (bulk population) were incubated with 10 nM scCD40L-scCD27L in presence or absence of cross-linked anti-human CD3 antibody as primary suboptimal stimulus. After 3 days at 37° C., different subpopulations were identified in flow cytometry by CD marker staining (anti-CD3, anti-CD4, anti-CD8, anti-CD20 and anti-CD56), the surface expression of CD40 and CD27 was determined by antibody staining and the binding of the single-chain duokine was assessed by detecting its FLAG-tag. $1.5 \times 10^5$ CFSE-labeled PBMC (bulk population, different PBMC batch) were incubated with 30, 3, 0.3 or 0 nM scCD40L-scCD27L in presence or absence of cross-linked anti-human CD3 antibody as primary suboptimal stimulus. After 6 days, proliferation of CD4 and CD8 T cells was determined in flow cytometry by CFSE-dilution.

Example 23: Binding of a Trans-Acting Single-Chain Duokine to Human Immune Cells and Induction of T Cell Proliferation The connection between binding to human immune cells and induction of T cell proliferation was examined for a second selected trans-acting single-chain duokine. For this, 2.5×10$^5$ human PBMC (bulk population) were incubated with 10 nM scCD40L-scCD27L in presence or absence of cross-linked anti-human CD3 antibody as primary suboptimal stimulus. After 3 days at 37° C., different subpopulations were identified in flow cytometry by CD marker staining (anti-CD3, anti-CD4, anti-CD8, anti-CD20 and anti-CD56). The surface expression of CD40 and CD27 was determined by antibody staining and the binding of the single-chain duokine was assessed by detecting its FLAG-tag. 1.5×10$^5$ CFSE-labeled PBMC (bulk population, different PBMC batch) were incubated with 30, 3, 0.3 or 0 nM scCD40L-scCD27L in presence or absence of cross-linked anti-human CD3 antibody as primary suboptimal stimulus. After 6 days, proliferation of CD4+ and CD8+ T cells was determined in flow cytometry by CFSE-dilution. When applied in combination with cross-linked anti-human CD3 antibody as primary stimulus, scCD40L-scCD27L enhanced the initial CD3-mediated proliferation of CD4+ and CD8+ T cells by 20-35% already at low concentrations of 0.3 nM (FIG. 36, lower right). Generally, slightly more CD8+ T cells (60%) than CD4+ T cells (45%) started to proliferate. CD27 was constitutively expressed on all CD8+ and CD4+ T cells as revealed by antibody staining, binding of scCD40L-scCD27L duokine was detected on 50% of all CD4+ T cells but was below detection level on CD8+ T cells. scCD40L-scCD27L was also found to bind the complete population of B cells constitutively expressing CD40 (FIG. 36, lower left). Accordingly, a direct transactivation by scCD40L-scCD27L via CD27+ CD4 cell-CD40+ B cell interaction readily accounts for CD4+ T cell proliferation, whereas in the case of CD8+ T cells additional, so far non-specified mechanisms/cells appear necessary to enable strong transactivation by this single chain duokine. Without any CD3 stimulation, T cell proliferation in response to duokine scCD40L-scCD27L raises from 1 to ~10% and 5 to 25% for CD8+ and CD4+ T cells, respectively, (FIG. 36, upper right) showing that some T cells are able to respond to costimulatory signals without intentional CD3 activation, again suggesting existence of a subpopulation of preactivated cells.

In summary, the considerable T cell activation mediated by scCD40L-scCD27L can be attributed to the constitutive expression of CD27 on all T cells and CD40 on all B cells (FIG. 36, upper left) leading to extended crosstalk and activation of different immune cells.

The invention claimed is:

1. A cytokine fusion protein comprising
   (i) three extracellular domains or fragments or variants thereof of a first ligand of the tumor necrosis factor (TNF) superfamily forming a first homotrimer capable of binding to a receptor of the first ligand and
   (ii) three extracellular domains or fragments or variants thereof of a second ligand of the TNF superfamily forming a second homotrimer capable of binding to a receptor of the second ligand,
   wherein
   the first ligand is CD40L (CD40 ligand) and the second ligand is 4-1BBL (4-1BB ligand) wherein the extracellular domain of CD40L comprises amino acid residues 51 to 261 of SEQ ID NO: 1, and the extracellular domain of 4-1BBL comprises amino acid residues 71 to 254 of SEQ ID NO: 3,
   the first homotrimer and the second homotrimer are covalently linked, optionally via one or more peptide linkers, and
   the extracellular domain variants have 95% sequence identity to the corresponding extracellular domain.

2. The cytokine fusion protein according to claim 1, wherein the three extracellular domains or fragments or variants thereof of the first ligand and/or the three extracellular domains or fragments or variants thereof of the second ligand are covalently linked.

3. The cytokine fusion protein according to claim 1, comprising a molecule/structure having the general formula $$N'\text{-}A\text{-}L_A\text{-}A\text{-}L_A\text{-}A\text{-}L\text{-}B\text{-}L_B\text{-}B\text{-}L_B\text{-}B\text{-}C' \quad \text{(Formula I)},$$

wherein A comprises the extracellular domain or a fragment or a variant thereof of the first ligand, and B comprises the extracellular domain or a fragment or variant thereof of the second ligand, and
wherein L comprises a peptide linker, and
$L_A$ and $L_B$ are, at each occurrence, independently selected from a covalent bond and a peptide linker.

4. The cytokine fusion protein according to claim 3, wherein L further comprises a multimerization domain, allowing the multimerization of the cytokine fusion protein.

5. The cytokine fusion protein according to claim 4, wherein the dimerization domain is selected from the group consisting of an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an Fc domain, an uteroglobin dimerization domain and functional variants of any one of the foregoing.

6. The cytokine fusion protein according to claim 4, being present as a multimeric complex.

7. The cytokine fusion protein according to claim 1, comprising at least one subunit with the general formula:

N'-A-L-B-C'    (Formula II), wherein A comprises the extracellular domain or a fragment or variant thereof of the first ligand, and B comprises the extracellular domain or a fragment or variant thereof of the second ligand, wherein L comprises a peptide linker, and wherein, when there are three subunits of Formula II, the three subunits form the cytokine fusion protein.

8. The cytokine fusion protein according to claim 1, further comprising at least one label or tag allowing the detection and/or isolation of the cytokine fusion protein.

9. The cytokine fusion protein according to claim 7 comprising three subunits of Formula II.

10. The cytokine fusion protein according to claim 4 wherein the multimerization is dimerization.

11. The cytokine fusion protein according to claim 6, wherein the cytokine fusion protein is a dimeric complex.

12. The cytokine fusion protein according to claim 1 wherein the extracellular domain of CD40L comprises amino acid residues 116 to 261 of SEQ ID NO: 1.

13. A cytokine fusion protein comprising a first block comprising three extracellular domains or fragments or variants thereof of a first ligand of the tumor necrosis factor (TNF) superfamily which are covalently linked to each other and a second block comprising three extracellular domains or fragments or variants thereof of a second ligand of the TNF superfamily which are covalently linked to each other, wherein the first ligand and the second ligand are different, and wherein the first block and the second block are covalently linked to each other wherein the extracellular domain variants have at least 95% sequence identity to the corresponding extracellular domain.

14. The cytokine fusion protein according to claim 13, wherein the three extracellular domains or fragments or variants thereof of the first ligand form a first homotrimer capable of binding to a receptor of the first ligand, and the three extracellular domains or fragments or variants thereof of the second ligand form a second homotrimer capable of binding to a receptor of the second ligand.

15. The cytokine fusion protein according to claim 13, wherein the three extracellular domains of the first ligand and/or the three extracellular domains of the second ligand and/or the first block and the second block are covalently linked via peptide linkers.

16. The cytokine fusion protein according to claim 13, further comprising at least one label or tag allowing the detection and/or isolation of the cytokine fusion protein.

17. The cytokine fusion protein according to claim 13, comprising a molecule or structure having the general formula N'-A-$L_A$-A-$L_A$-A-L-B-$L_B$B-$L_B$-B-C'    (Formula I), wherein A comprises the extracellular domain or a fragment or variant thereof of the first ligand, and B comprises the extracellular domain or a fragment or variant thereof of the second ligand, and wherein L comprises a peptide linker, and $L_A$ and $L_B$ are, at each occurrence, independently selected from a covalent bond and a peptide linker.

18. The cytokine fusion protein according to claim 17, wherein L further comprises a multimerization domain allowing the multimerization of the cytokine fusion protein.

19. The cytokine fusion protein according to claim 18, wherein the multimerization domain is a dimerization domain is selected from the group consisting of an IgE heavy-chain domain 2 (EHD2), an IgM heavy-chain domain 2 (MHD2), an IgG heavy-chain domain 3 (GHD3), an IgA heavy-chain domain 3 (AHD2), an IgD heavy-chain domain 3 (DHD3), an IgE heavy-chain domain 4 (EHD4), an IgM heavy-chain domain 4 (MHD4), an Fc domain, an uteroglobin dimerization domain and functional variants of any one of the foregoing.

20. The cytokine fusion protein according to claim 18 wherein the multimerization domain is a dimerization domain allowing dimerization of the cytokine fusion protein.

21. The cytokine fusion protein according to claim 18, being present as a multimeric complex.

22. The cytokine fusion protein according to claim 21 present as a dimeric complex.

* * * * *

SEQUENCE LISTING

```
<160> NUMBER OF SEQ ID NOS: 25

<210> SEQ ID NO 1
<211> LENGTH: 261
<212> TYPE: PRT
<213> ORGANISM: Homo sapiens

<400> SEQUENCE: 1

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 2
```

```
<211> LENGTH: 193
<212> TYPE: PRT
<213> ORGANISM: Homo sapiens

<400> SEQUENCE: 2

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 3
<211> LENGTH: 254
<212> TYPE: PRT
<213> ORGANISM: Homo sapiens

<400> SEQUENCE: 3

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140
```

```
Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 4
<211> LENGTH: 183
<212> TYPE: PRT
<213> ORGANISM: Homo sapiens

<400> SEQUENCE: 4

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 5
<211> LENGTH: 211
<212> TYPE: PRT
<213> ORGANISM: Artificial Sequence
<220> FEATURE:
<223> OTHER INFORMATION: h1_CD40L

<400> SEQUENCE: 5

Asp Lys Ile Glu Asp Glu Arg Asn Leu His Glu Asp Phe Val Phe Met
1               5                   10                  15

Lys Thr Ile Gln Arg Cys Asn Thr Gly Glu Arg Ser Leu Ser Leu Leu
```

```
                    20                  25                  30
Asn Cys Glu Glu Ile Lys Ser Gln Phe Glu Gly Phe Val Lys Asp Ile
                35                  40                  45

Met Leu Asn Lys Glu Glu Thr Lys Lys Glu Asn Ser Phe Glu Met Gln
         50                  55                  60

Lys Gly Asp Gln Asn Pro Gln Ile Ala Ala His Val Ile Ser Glu Ala
 65                  70                  75                  80

Ser Ser Lys Thr Thr Ser Val Leu Gln Trp Ala Glu Lys Gly Tyr Tyr
                 85                  90                  95

Thr Met Ser Asn Asn Leu Val Thr Leu Glu Asn Gly Lys Gln Leu Thr
                100                 105                 110

Val Lys Arg Gln Gly Leu Tyr Tyr Ile Tyr Ala Gln Val Thr Phe Cys
            115                 120                 125

Ser Asn Arg Glu Ala Ser Ser Gln Ala Pro Phe Ile Ala Ser Leu Cys
        130                 135                 140

Leu Lys Ser Pro Gly Arg Phe Glu Arg Ile Leu Leu Arg Ala Ala Asn
145                 150                 155                 160

Thr His Ser Ser Ala Lys Pro Cys Gly Gln Gln Ser Ile His Leu Gly
                165                 170                 175

Gly Val Phe Glu Leu Gln Pro Gly Ala Ser Val Phe Val Asn Val Thr
            180                 185                 190

Asp Pro Ser Gln Val Ser His Gly Thr Gly Phe Thr Ser Phe Gly Leu
        195                 200                 205

Leu Lys Leu
    210

<210> SEQ ID NO 6
<211> LENGTH: 142
<212> TYPE: PRT
<213> ORGANISM: Artificial Sequence
<220> FEATURE:
<223> OTHER INFORMATION: h1_CD27L

<400> SEQUENCE: 6

Ser Leu Gly Trp Asp Val Ala Glu Leu Gln Leu Asn His Thr Gly Pro
1               5                   10                  15

Gln Gln Asp Pro Arg Leu Tyr Trp Gln Gly Gly Pro Ala Leu Gly Arg
            20                  25                  30

Ser Phe Leu His Gly Pro Glu Leu Asp Lys Gly Gln Leu Arg Ile His
        35                  40                  45

Arg Asp Gly Ile Tyr Met Val His Ile Gln Val Thr Leu Ala Ile Cys
    50                  55                  60

Ser Ser Thr Thr Ala Ser Arg His His Pro Thr Thr Leu Ala Val Gly
 65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
        115                 120                 125

Asn Thr Asp Glu Thr Phe Phe Gly Val Gln Trp Val Arg Pro
    130                 135                 140

<210> SEQ ID NO 7
<211> LENGTH: 184
<212> TYPE: PRT
```

<213> ORGANISM: Artificial Sequence
<220> FEATURE:
<223> OTHER INFORMATION: h1_4-1BBL

<400> SEQUENCE: 7

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 8
<211> LENGTH: 133
<212> TYPE: PRT
<213> ORGANISM: Artificial Sequence
<220> FEATURE:
<223> OTHER INFORMATION: h1_OX40L

<400> SEQUENCE: 8

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 9
<211> LENGTH: 452
<212> TYPE: PRT
<213> ORGANISM: Artificial Sequence
<220> FEATURE:
<223> OTHER INFORMATION: h3_CD40L

<400> SEQUENCE: 9

```
Gly Asp Gln Asn Pro Gln Ile Ala Ala His Val Ile Ser Glu Ala Ser
1               5                   10                  15

Ser Lys Thr Thr Ser Val Leu Gln Trp Ala Glu Lys Gly Tyr Tyr Thr
            20                  25                  30

Met Ser Asn Asn Leu Val Thr Leu Glu Asn Gly Lys Gln Leu Thr Val
        35                  40                  45

Lys Arg Gln Gly Leu Tyr Tyr Ile Tyr Ala Gln Val Thr Phe Cys Ser
50                  55                  60

Asn Arg Glu Ala Ser Ser Gln Ala Pro Phe Ile Ala Ser Leu Cys Leu
65                  70                  75                  80

Lys Ser Pro Gly Arg Phe Glu Arg Ile Leu Leu Arg Ala Ala Asn Thr
                85                  90                  95

His Ser Ser Ala Lys Pro Cys Gly Gln Gln Ser Ile His Leu Gly Gly
            100                 105                 110

Val Phe Glu Leu Gln Pro Gly Ala Ser Val Phe Val Asn Val Thr Asp
        115                 120                 125

Pro Ser Gln Val Ser His Gly Thr Gly Phe Thr Ser Phe Gly Leu Leu
130                 135                 140

Lys Leu Gly Gly Gly Ser Gly Gly Gly Gly Asp Gln Asn Pro Gln Ile
145                 150                 155                 160

Ala Ala His Val Ile Ser Glu Ala Ser Ser Lys Thr Thr Ser Val Leu
                165                 170                 175

Gln Trp Ala Glu Lys Gly Tyr Tyr Thr Met Ser Asn Asn Leu Val Thr
            180                 185                 190

Leu Glu Asn Gly Lys Gln Leu Thr Val Lys Arg Gln Gly Leu Tyr Tyr
        195                 200                 205

Ile Tyr Ala Gln Val Thr Phe Cys Ser Asn Arg Glu Ala Ser Ser Gln
210                 215                 220

Ala Pro Phe Ile Ala Ser Leu Cys Leu Lys Ser Pro Gly Arg Phe Glu
225                 230                 235                 240

Arg Ile Leu Leu Arg Ala Ala Asn Thr His Ser Ser Ala Lys Pro Cys
                245                 250                 255

Gly Gln Gln Ser Ile His Leu Gly Gly Val Phe Glu Leu Gln Pro Gly
            260                 265                 270

Ala Ser Val Phe Val Asn Val Thr Asp Pro Ser Gln Val Ser His Gly
        275                 280                 285

Thr Gly Phe Thr Ser Phe Gly Leu Leu Lys Leu Gly Gly Gly Ser Gly
290                 295                 300

Gly Gly Gly Asp Gln Asn Pro Gln Ile Ala Ala His Val Ile Ser Glu
305                 310                 315                 320

Ala Ser Ser Lys Thr Thr Ser Val Leu Gln Trp Ala Glu Lys Gly Tyr
                325                 330                 335

Tyr Thr Met Ser Asn Asn Leu Val Thr Leu Glu Asn Gly Lys Gln Leu
            340                 345                 350

Thr Val Lys Arg Gln Gly Leu Tyr Tyr Ile Tyr Ala Gln Val Thr Phe
        355                 360                 365
```

```
Cys Ser Asn Arg Glu Ala Ser Ser Gln Ala Pro Phe Ile Ala Ser Leu
    370                 375                 380

Cys Leu Lys Ser Pro Gly Arg Phe Glu Arg Ile Leu Leu Arg Ala Ala
385                 390                 395                 400

Asn Thr His Ser Ala Lys Pro Cys Gly Gln Gln Ser Ile His Leu
            405                 410                 415

Gly Gly Val Phe Glu Leu Gln Pro Gly Ala Ser Val Phe Val Asn Val
            420                 425                 430

Thr Asp Pro Ser Gln Val Ser His Gly Thr Gly Phe Thr Ser Phe Gly
            435                 440                 445

Leu Leu Lys Leu
    450

<210> SEQ ID NO 10
<211> LENGTH: 440
<212> TYPE: PRT
<213> ORGANISM: Artificial Sequence
<220> FEATURE:
<223> OTHER INFORMATION: h3_CD27L

<400> SEQUENCE: 10

Ser Leu Gly Trp Asp Val Ala Glu Leu Gln Leu Asn His Thr Gly Pro
1               5                   10                  15

Gln Gln Asp Pro Arg Leu Tyr Trp Gln Gly Gly Pro Ala Leu Gly Arg
            20                  25                  30

Ser Phe Leu His Gly Pro Glu Leu Asp Lys Gly Gln Leu Arg Ile His
        35                  40                  45

Arg Asp Gly Ile Tyr Met Val His Ile Gln Val Thr Leu Ala Ile Cys
50                  55                  60

Ser Ser Thr Thr Ala Ser Arg His His Pro Thr Thr Leu Ala Val Gly
65                  70                  75                  80

Ile Cys Ser Pro Ala Ser Arg Ser Ile Ser Leu Leu Arg Leu Ser Phe
                85                  90                  95

His Gln Gly Cys Thr Ile Ala Ser Gln Arg Leu Thr Pro Leu Ala Arg
            100                 105                 110

Gly Asp Thr Leu Cys Thr Asn Leu Thr Gly Thr Leu Leu Pro Ser Arg
        115                 120                 125

Asn Thr Asp Glu Thr Phe Phe Gly Val Gln Trp Val Arg Pro Gly Gly
130                 135                 140

Gly Ser Gly Gly Gly Ser Leu Gly Trp Asp Val Ala Glu Leu Gln Leu
145                 150                 155                 160

Asn His Thr Gly Pro Gln Gln Asp Pro Arg Leu Tyr Trp Gln Gly Gly
                165                 170                 175

Pro Ala Leu Gly Arg Ser Phe Leu His Gly Pro Glu Leu Asp Lys Gly
            180                 185                 190

Gln Leu Arg Ile His Arg Asp Gly Ile Tyr Met Val His Ile Gln Val
        195                 200                 205

Thr Leu Ala Ile Cys Ser Ser Thr Thr Ala Ser Arg His His Pro Thr
210                 215                 220

Thr Leu Ala Val Gly Ile Cys Ser Pro Ala Ser Arg Ser Ile Ser Leu
225                 230                 235                 240

Leu Arg Leu Ser Phe His Gln Gly Cys Thr Ile Ala Ser Gln Arg Leu
                245                 250                 255

Thr Pro Leu Ala Arg Gly Asp Thr Leu Cys Thr Asn Leu Thr Gly Thr
            260                 265                 270
```

```
Leu Leu Pro Ser Arg Asn Thr Asp Glu Thr Phe Phe Gly Val Gln Trp
            275                 280                 285

Val Arg Pro Gly Gly Gly Ser Gly Gly Gly Ser Leu Gly Trp Asp Val
        290                 295                 300

Ala Glu Leu Gln Leu Asn His Thr Gly Pro Gln Gln Asp Pro Arg Leu
305                 310                 315                 320

Tyr Trp Gln Gly Gly Pro Ala Leu Gly Arg Ser Phe Leu His Gly Pro
            325                 330                 335

Glu Leu Asp Lys Gly Gln Leu Arg Ile His Arg Asp Gly Ile Tyr Met
            340                 345                 350

Val His Ile Gln Val Thr Leu Ala Ile Cys Ser Ser Thr Thr Ala Ser
            355                 360                 365

Arg His His Pro Thr Thr Leu Ala Val Gly Ile Cys Ser Pro Ala Ser
        370                 375                 380

Arg Ser Ile Ser Leu Leu Arg Leu Ser Phe His Gln Gly Cys Thr Ile
385                 390                 395                 400

Ala Ser Gln Arg Leu Thr Pro Leu Ala Arg Gly Asp Thr Leu Cys Thr
            405                 410                 415

Asn Leu Thr Gly Thr Leu Leu Pro Ser Arg Asn Thr Asp Glu Thr Phe
        420                 425                 430

Phe Gly Val Gln Trp Val Arg Pro
            435                 440

<210> SEQ ID NO 11
<211> LENGTH: 592
<212> TYPE: PRT
<213> ORGANISM: Artificial Sequence
<220> FEATURE:
<223> OTHER INFORMATION: h3_4-1BBL

<400> SEQUENCE: 11

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
            85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
            165                 170                 175

Gly Leu Pro Ser Pro Arg Ser Glu Gly Gly Gly Ser Gly Gly Gly Gly
        180                 185                 190
```

```
Gly Ser Gly Gly Gly Ser Gly Gly Gly Ser Arg Glu Gly Pro
        195                 200                 205

Glu Leu Ser Pro Asp Pro Ala Gly Leu Leu Asp Leu Arg Gln Gly
    210                 215                 220

Met Phe Ala Gln Leu Val Ala Gln Asn Val Leu Leu Ile Asp Gly Pro
225                 230                 235                 240

Leu Ser Trp Tyr Ser Asp Pro Gly Leu Ala Gly Val Ser Leu Thr Gly
                245                 250                 255

Gly Leu Ser Tyr Lys Glu Asp Thr Lys Glu Leu Val Ala Lys Ala
            260                 265                 270

Gly Val Tyr Tyr Val Phe Phe Gln Leu Glu Leu Arg Arg Val Val Ala
        275                 280                 285

Gly Glu Gly Ser Gly Ser Val Ser Leu Ala Leu His Leu Gln Pro Leu
    290                 295                 300

Arg Ser Ala Ala Gly Ala Ala Ala Leu Ala Leu Thr Val Asp Leu Pro
305                 310                 315                 320

Pro Ala Ser Ser Glu Ala Arg Asn Ser Ala Phe Gly Phe Gln Gly Arg
                325                 330                 335

Leu Leu His Leu Ser Ala Gly Gln Arg Leu Gly Val His Leu His Thr
            340                 345                 350

Glu Ala Arg Ala Arg His Ala Trp Gln Leu Thr Gln Gly Ala Thr Val
        355                 360                 365

Leu Gly Leu Phe Arg Val Thr Pro Glu Ile Pro Ala Gly Leu Pro Ser
    370                 375                 380

Pro Arg Ser Glu Gly Gly Gly Ser Gly Gly Gly Ser Gly Gly
385                 390                 395                 400

Gly Gly Ser Gly Gly Gly Ser Arg Glu Gly Pro Glu Leu Ser Pro
                405                 410                 415

Asp Asp Pro Ala Gly Leu Leu Asp Leu Arg Gln Gly Met Phe Ala Gln
                420                 425                 430

Leu Val Ala Gln Asn Val Leu Leu Ile Asp Gly Pro Leu Ser Trp Tyr
            435                 440                 445

Ser Asp Pro Gly Leu Ala Gly Val Ser Leu Thr Gly Gly Leu Ser Tyr
        450                 455                 460

Lys Glu Asp Thr Lys Glu Leu Val Val Ala Lys Ala Gly Val Tyr Tyr
465                 470                 475                 480

Val Phe Phe Gln Leu Glu Leu Arg Arg Val Val Ala Gly Glu Gly Ser
                485                 490                 495

Gly Ser Val Ser Leu Ala Leu His Leu Gln Pro Leu Arg Ser Ala Ala
            500                 505                 510

Gly Ala Ala Ala Leu Ala Leu Thr Val Asp Leu Pro Pro Ala Ser Ser
        515                 520                 525

Glu Ala Arg Asn Ser Ala Phe Gly Phe Gln Gly Arg Leu Leu His Leu
    530                 535                 540

Ser Ala Gly Gln Arg Leu Gly Val His Leu His Thr Glu Ala Arg Ala
545                 550                 555                 560

Arg His Ala Trp Gln Leu Thr Gln Gly Ala Thr Val Leu Gly Leu Phe
                565                 570                 575

Arg Val Thr Pro Glu Ile Pro Ala Gly Leu Pro Ser Pro Arg Ser Glu
            580                 585                 590

<210> SEQ ID NO 12
<211> LENGTH: 413
<212> TYPE: PRT
```

<213> ORGANISM: Artificial Sequence
<220> FEATURE:
<223> OTHER INFORMATION: h3_OX40L

<400> SEQUENCE: 12

```
Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Gly Gly Gly Ser Gly Gly Gly Gln Val Ser His
130                 135                 140

Arg Tyr Pro Arg Ile Gln Ser Ile Lys Val Gln Phe Thr Glu Tyr Lys
145                 150                 155                 160

Lys Glu Lys Gly Phe Ile Leu Thr Ser Gln Lys Glu Asp Glu Ile Met
                165                 170                 175

Lys Val Gln Asn Asn Ser Val Ile Ile Asn Cys Asp Gly Phe Tyr Leu
            180                 185                 190

Ile Ser Leu Lys Gly Tyr Phe Ser Gln Glu Val Asn Ile Ser Leu His
        195                 200                 205

Tyr Gln Lys Asp Glu Glu Pro Leu Phe Gln Leu Lys Lys Val Arg Ser
210                 215                 220

Val Asn Ser Leu Met Val Ala Ser Leu Thr Tyr Lys Asp Lys Val Tyr
225                 230                 235                 240

Leu Asn Val Thr Thr Asp Asn Thr Ser Leu Asp Asp Phe His Val Asn
                245                 250                 255

Gly Gly Glu Leu Ile Leu Ile His Gln Asn Pro Gly Glu Phe Cys Val
            260                 265                 270

Leu Gly Gly Gly Ser Gly Gly Gly Gln Val Ser His Arg Tyr Pro Arg
        275                 280                 285

Ile Gln Ser Ile Lys Val Gln Phe Thr Glu Tyr Lys Lys Glu Lys Gly
290                 295                 300

Phe Ile Leu Thr Ser Gln Lys Glu Asp Glu Ile Met Lys Val Gln Asn
305                 310                 315                 320

Asn Ser Val Ile Ile Asn Cys Asp Gly Phe Tyr Leu Ile Ser Leu Lys
                325                 330                 335

Gly Tyr Phe Ser Gln Glu Val Asn Ile Ser Leu His Tyr Gln Lys Asp
            340                 345                 350

Glu Glu Pro Leu Phe Gln Leu Lys Lys Val Arg Ser Val Asn Ser Leu
        355                 360                 365

Met Val Ala Ser Leu Thr Tyr Lys Asp Lys Val Tyr Leu Asn Val Thr
370                 375                 380

Thr Asp Asn Thr Ser Leu Asp Asp Phe His Val Asn Gly Gly Glu Leu
```

Ile Leu Ile His Gln Asn Pro Gly Glu Phe Cys Val Leu
        405                 410

<210> SEQ ID NO 13
<211> LENGTH: 40
<212> TYPE: DNA
<213> ORGANISM: Artificial Sequence
<220> FEATURE:
<223> OTHER INFORMATION: hAg-Kozak

<400> SEQUENCE: 13
attcttctgg tccccacaga ctcagagaga acccgccacc                40

<210> SEQ ID NO 14
<211> LENGTH: 84
<212> TYPE: DNA
<213> ORGANISM: Artificial Sequence
<220> FEATURE:
<223> OTHER INFORMATION: Sec

<400> SEQUENCE: 14
atgagagtga ccgcccccag aaccctgatc ctgctgctgt ctggcgccct ggccctgaca    60
gagacatggg ccggaagcgg atcc                                          84

<210> SEQ ID NO 15
<211> LENGTH: 28
<212> TYPE: PRT
<213> ORGANISM: Artificial Sequence
<220> FEATURE:
<223> OTHER INFORMATION: Sec

<400> SEQUENCE: 15

Met Arg Val Thr Ala Pro Arg Thr Leu Ile Leu Leu Leu Ser Gly Ala
1               5                   10                  15

Leu Ala Leu Thr Glu Thr Trp Ala Gly Ser Gly Ser
            20                  25

<210> SEQ ID NO 16
<211> LENGTH: 287
<212> TYPE: DNA
<213> ORGANISM: Artificial Sequence
<220> FEATURE:
<223> OTHER INFORMATION: 2hBgUTR

<400> SEQUENCE: 16
ctcgagagct cgctttcttg ctgtccaatt tctattaaag gttcctttgt tccctaagtc    60
caactactaa actgggggat attatgaagg gccttgagca tctggattct gcctaataaa   120 aaacattat tttcattgct gcgtcgagag ctcgctttct tgctgtccaa tttctattaa   180
aggttccttt gttccctaag tccaactact aaactggggg atattatgaa gggccttgag   240
catctggatt ctgcctaata aaaaacattt attttcattg ctgcgtc                287

<210> SEQ ID NO 17
<211> LENGTH: 134
<212> TYPE: DNA
<213> ORGANISM: Artificial Sequence
<220> FEATURE:
<223> OTHER INFORMATION: A120

<400> SEQUENCE: 17
gagacctggt ccagagtcgc tagcaaaaaa aaaaaaaaaa aaaaaaaaaa aaaagcatat    60

```
gactaaaaaa aaaaaaaaaa aaaaaaaaaa aaaaaaaaaa aaaaaaaaaa aaaaaaaaaa    120
aaaaaaaaaa aaaa                                                      134
```

<210> SEQ ID NO 18
<211> LENGTH: 45
<212> TYPE: DNA
<213> ORGANISM: Artificial Sequence
<220> FEATURE:
<223> OTHER INFORMATION: Linker

<400> SEQUENCE: 18

```
ggaggcggtg gtagtggagg tggcgggtcc ggtggaggtg gaagc                     45
```

<210> SEQ ID NO 19
<211> LENGTH: 15
<212> TYPE: PRT
<213> ORGANISM: Artificial Sequence
<220> FEATURE:
<223> OTHER INFORMATION: Linker

<400> SEQUENCE: 19

```
Gly Gly Gly Gly Ser Gly Gly Gly Gly Ser Gly Gly Gly Gly Ser
1               5                   10                  15
```

<210> SEQ ID NO 20
<211> LENGTH: 14
<212> TYPE: PRT
<213> ORGANISM: Artificial Sequence
<220> FEATURE:
<223> OTHER INFORMATION: Linker

<400> SEQUENCE: 20

```
Gly Gly Gly Gly Ser Gly Gly Gly Thr Gly Gly Gly Gly Ser
1               5                   10
```

<210> SEQ ID NO 21
<211> LENGTH: 20
<212> TYPE: PRT
<213> ORGANISM: Artificial Sequence
<220> FEATURE:
<223> OTHER INFORMATION: Linker

<400> SEQUENCE: 21

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 22
<211> LENGTH: 19
<212> TYPE: PRT
<213> ORGANISM: Artificial Sequence
<220> FEATURE:
<223> OTHER INFORMATION: Sec

<400> SEQUENCE: 22

```
Met Asp Trp Thr Trp Arg Val Phe Cys Leu Leu Ala Val Ala Pro Gly
1               5                   10                  15

Ala His Ser
```

<210> SEQ ID NO 23
<211> LENGTH: 106
<212> TYPE: PRT
<213> ORGANISM: Artificial Sequence
<220> FEATURE:

```
<223> OTHER INFORMATION: hEHD2

<400> SEQUENCE: 23

Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
            20                  25                  30

Tyr Thr Pro Gly Thr Ile Asn Ile Thr Trp Leu Glu Asp Gly Gln Val
        35                  40                  45

Met Asp Val Asp Leu Ser Thr Ala Ser Thr Thr Gln Glu Gly Glu Leu
    50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn
            100                 105

<210> SEQ ID NO 24
<211> LENGTH: 7
<212> TYPE: PRT
<213> ORGANISM: Artificial Sequence
<220> FEATURE:
<223> OTHER INFORMATION: Linker

<400> SEQUENCE: 24

Gly Gly Gly Ser Gly Gly Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Linker

<400> SEQUENCE: 25

Gly Gly Ser Gly Gly
1               5
```